(12) United States Patent
Solomon et al.

(10) Patent No.: US 6,919,075 B1
(45) Date of Patent: *Jul. 19, 2005

(54) BACTERIOPHAGE DISPLAYING Aβ EPITOPES AND METHOD OF USE

(75) Inventors: Beka Solomon, Herzlia (IL); Dan Frenkel, Rehovot (IL); Eilat Hanan, Tel Aviv (IL)

(73) Assignee: Ramot at Tel Aviv University Ltd., Tel Aviv (IL)

(*) Notice: Subject to any disclaimer, the term of this patent is extended or adjusted under 35 U.S.C. 154(b) by 228 days.

This patent is subject to a terminal disclaimer.

(21) Appl. No.: 09/830,954
(22) PCT Filed: Aug. 31, 2000
(86) PCT No.: PCT/IL00/00518

§ 371 (c)(1),
(2), (4) Date: Aug. 7, 2001

(87) PCT Pub. No.: WO01/18169

PCT Pub. Date: Mar. 15, 2001

(51) Int. Cl.⁷ .................. A01N 61/00; C12N 15/00; C12N 15/86
(52) U.S. Cl. ................. 424/93.2; 424/93.6; 435/320.1
(58) Field of Search ................. 424/93.2, 93.6, 424/184.1, 193.1, 196.11, 199.1; 435/320.1, 235.1

(56) References Cited

U.S. PATENT DOCUMENTS

| | | | |
|---|---|---|---|
| 5,811,093 A | 9/1998 | Merril et al. | |
| 6,703,015 B1 * | 3/2004 | Solomon et al. | 424/93.2 |
| 2002/0052311 A1 * | 5/2002 | Solomon et al. | 514/2 |
| 2004/0013647 A1 * | 1/2004 | Solomon et al. | 424/93.2 |

FOREIGN PATENT DOCUMENTS

WO    WO 92/07077    4/1992

OTHER PUBLICATIONS

Skolnick & Fetrow (2000) "From genes to protein structure and function: novel applications of computational approaches in the genomic era." Trends in Biotech. 18(1): 34–39.*

Jobling & Holmes (1991) "Analysis of structure and function of the B Subunit of cholera toxin by the use of site–directed mutagenesis." Molecular Microbiology 5(7): 1755–67.*

Goldsby et al. (2002) Kuby Immunology Chapter 18 "Vaccines" (pp. 449–465).*

Tobin & Signer (Dec. 2000) "Huntington's disease: the challenge for cell biologists." Trends in Cell Biology 10(12): 531–536.*

Su et al. (Feb. 6, 1999) "Intravascular infusions of soluble b–amyloid compromise the blood–brain barrier, activate CNS glia cells and induce peripheral hemorrhage." Brain Research 818(1): 105–117.*

Goldfarb and Brown (1995) "The Transmissible Spongiform Encephalopathies." Annu. Rev. Med. 46: 57–66.*

(Continued)

Primary Examiner—Elizabeth C. Kemmerer
Assistant Examiner—Christopher James Nichols
(74) Attorney, Agent, or Firm—Browdy and Neimark, P.L.L.C.

(57) ABSTRACT

A method of immunizing against plaque forming diseases using display technology is provided. The method utilize novel agents, or pharmaceutical compositions for vaccination against plaque forming diseases which rely upon presentation of an antigen or epitope on a display vehicle. The method further includes agents, or pharmaceutical compositions for vaccination against plaque forming diseases, which rely upon presentation of an antibody, or an active portion thereof, on a display vehicle. Whether antigens or antibodies are employed, disaggregation of plaques results from the immunization.

19 Claims, 20 Drawing Sheets

OTHER PUBLICATIONS

Kovács et al. (2002) "Mutations of the Prion Protein Gene." J. Neurol. 249: 1567–1582.*

Elan Press Releases (Jan. 18, 2002 and Mar. 1, 2002).*

Singh (1997) "Neuroautoimmunity: Pathologic Implications for Alzheimer's Disease." Gerontology 43:79–94.*

Castillo et al. (1995) "Amylin/Islet Amyloid Polypeptide: Biochemistry, Physiology, Patho–Physiology." Diabete et Metbolisme 213–25.*

Frenkel et al. (1998) "N–terminal EFRH sequence of Alzheimer's b–amyloid peptide represents the epiptope of its anti–aggregating antibodies." Journal of Neuroimmunology 88: 85–90.*

Smith, "Surface presentation of protein epitopes using bacteriophage expression systems", *Current Opinion in Biotechnology*, 2:668–673 (1991).

Renauld–Mongenie et al., "Induction of mucosal immune responses against a heterologous antigen fused to filamentous hemagglutinin after intranasal immunization with recombinant *Bordetella pertussis*", *Proc. Natl. Acad. Sci. USA*, 93:7944–7949 (1996).

Cesareni et al., "Minireview Peptides display on filamentous phage capsids a new powerful tool to study protein ligand interaction", *FEBS Letters*, 307:66–70 (1992).

Huse et al., "Application of a filamentous phage pVIII fusion protein system suitable for efficient production screening, and mutagenesis of F(ab) antibody fragments", *The Journal of Immunology*, (1992).

Jones et al., "Display of antibody chains on filamentous bacteriophage", *Methods in Molecular Biology*, 80:449–459, (1998).

Chang et al., "Expression of antibody Fab domains on bacteriophage surfaces potential use for antibody selection", *Journal of Immunology*, 147:3610–3614 (1991).

Glaser et al., "Antibody engineering by codon–based mutagenesis in a filamentous phage vector system", *The Journal of Immunology*, 149:3903–3913 (1992).

Hoogenboom et al., "Building antibodies from their genes", *Immunological Reviews*, 130–41–68 (1992).

Barbas et al., "Semisynthetic combinatorial antibody libraries: a chemical solution to the diversity problem", *Natl. Acad. Sci. USA*, 4457:4461 (1992).

Marks et al., "Molecular evolution of proteins on filamentous phage", *The Journal of Biological Chemistry*, 267:16007–16010 (1992).

Hawkins et al., "Selection of phage antibodies by binding affinity mimicking affinity maturation", *J. Mol. Biol.*, 226:889–896 (1992).

Wetzel, "Commentary learning from the immune system laboratory methods for creating and refining molecular diversity in polypeptides", *Protein Engineering*, 4:371–374 (1991).

Lerner et al., "Antibodies without immunization", *Science*, 258:1313–1314 (1992).

Barbas et al., "Recombinant human Fab fragments neutralize human type 1 immunodeficiency virus in vitro", *Proc. Natl. Acad. Sci. USA*, 89:9339–9343 (1992).

Zebedee et al., "Human combinatorial antibody libraries to hepatitis B surface antigen", *Proc. Natl. Acad. Sci. USA*, 89:3175–3179 (1992).

Gram et al., "In vitro selection and affinity maturation of antibodies from a naïve combinatorial immunoglobulin library", *Proc. Natl. Acad. Sci. USA*, 89:3576–3580 (1992).

Kang et al., "Antibody redesign by chain shuffling from random combinatorial immunoglobulin libraries", *Proc. Natl. Acad. Sci. USA*, 88:11120–11123 (1991).

Garrard et al., "Assembly and enrichment in a monovalent phage display system", *Biotechnology*, 9:1373–1377 (1991).

Goessling et al., "Enhanced degradation of the ferritin repressor protein during induction of ferritin messenger RNA translation", *Science*, 256:670 (1992).

Marks et al., "By–passing immunization human antibodies from V–gene libraries displayed on phage", *J. Mol. Biol.*, 222:581–597 (1991).

Clackson et al., "Letters to nature making antibody fragments using phage display libraries", *Nature*, 352:624–628 (1991).

Barbas et al., "Assembly of combinatorial antibody libraries on phage surfaces: The gene III site", *Proc. Natl. Acad. Sci. USA*, 88:7978–7982 (1991).

McCafferty et al., "Letters to nature phage antibodies: filamentous phage displaying antibody variable domains", *Nature*, 348:552–554 (1990).

Kang et al., "Linkage of recognition and replication functions by assembling combinatorial antibody Fab libraries along phage surfaces", *Proc. Natl. Acad. Sci. USA*, 88:4363–4366 (1991).

Burtion et al., "A large array of human monoclonal antibodies to type 1 human immunodeficiency virus from combinatorial libraries of asymptomatic seropositive individuals", *Proc. Natl. Acad. Sci. USA*, 88:10134–10137 (1991).

Breitling et al., "Ad surface expression vector for antibody screening", *Gene*, 104:147–153 (1991).

Hoogenboom et al., "Multi–subunit proteins on the surface of filamentous phage: methodologies for displaying antibody (Fab) heavy and light chains", *Nucleic Acids Research*, 19:4133–4137 (1991).

Barbas et al., "Human monoclonal Fab fragments derived from a combinatorial library bind to respiratory syncytial virus F glycoprotein and neutralize infectivity", *Proc. Natl. Acad. Sci. USA*, 89:10164–10168 (1992).

Somerville et al., "Immunodetection of PrP$^{SC}$ in spleens of some scrapie–infected sheep but not BSE–infected cows", *Journal of General Virology*, 7:2389–2396 (1997).

Frenkel et al., "N–terminal EFRH sequence of Alzheimer's β–amyloid peptide represents the epitope of its anti–aggregating antibodies", *Journal of Neroimmunology*, 88:85–90 (1998).

Schenk et al., "Letters of nature immunization with amyloid–β attenuates Alzheimer–disease–like pathology in the PDDAPP mouse", *Nature*, 400:173–177 (1999).

Solomon et al., "Monoclonal antibodies inhibit in vitro fibrillar aggregation of the Alzheimer β–amyloid peptide", *Proc. Natl. Acad. Sci. USA*, 93:452–455 (1996).

Solomon et al., "Disaggregation of Alzheimer β–amyloid by site–directed mAb", *Proc. Natl. Acad. Sci. USA*. 94:4109–4112 (1997).

Motti et al., "Recognition by human sera and immunogenicity of HbsAg mimotopes selected from an M13 phage display library", *Gene*, 146:191–198 (1994).

Hanan et al., "Inhibitory effect of monoclonal antibodies on Alzheimer's β–amyloid peptide aggregation", *Int. J. Exp. Clin. Invest.* ., 3:130–133 (1996).

Meola et al., "Immunogenicity of filamentous phage displaying peptidemimotopes after oral administration", *Vaccine*, 15:1276–1285 (1997).

* cited by examiner

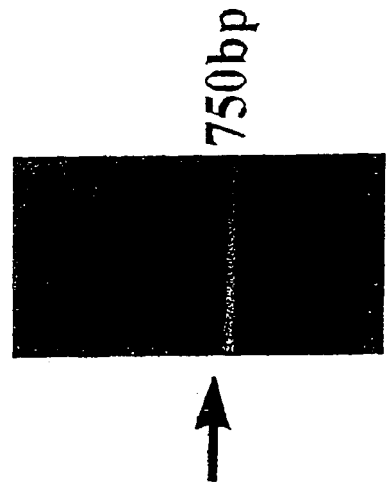
*FIG.1C* 750bp
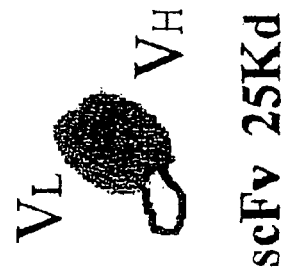
$V_L$ $V_H$
scFv 25Kd
*FIG.1E*
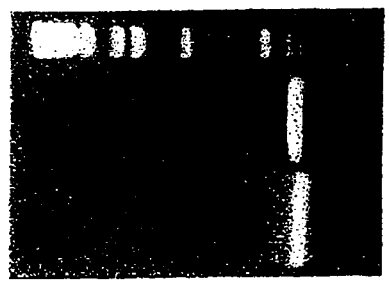
*FIG.1B*
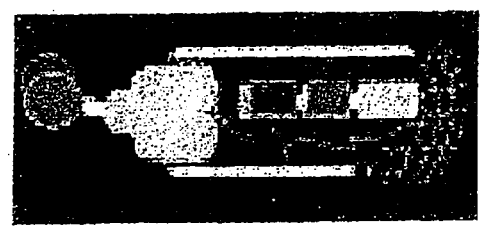
*FIG.1D*
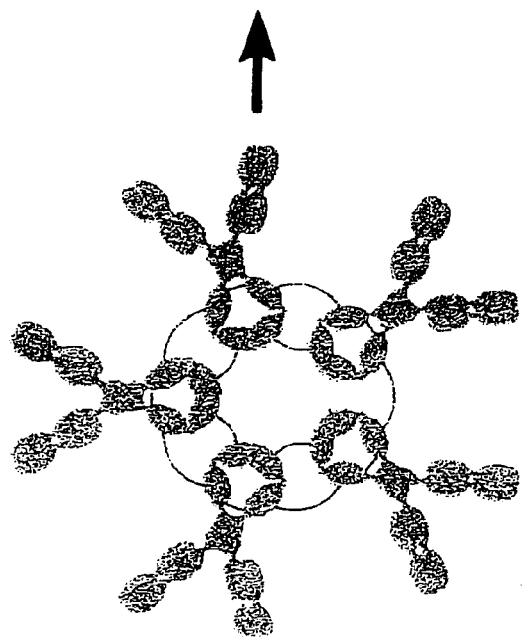
*FIG.1A*
IgM 950Kd

FIG. 11a

CAG GTC AAA CTG CAG GAG TCA GGG GCT GAG CTG GTG ACG CCT GGG GTC TCA GTG AAG ATT
gln val lys leu gln glu ser gly ala glu leu val arg pro gly val ser val lys ile TCC TGC AAG GGT TCT GGC TAC ACA TTC ACT GAT TAT GCT ATG CAC TGG GTG AAG CAG AGT
ser cys lys gly ser gly tyr thr phe thr asp tyr ala met his trp val lys gln ser
<u>                                              CDR 1                        </u>

CAT GCA AAG AGT CTA GAG TGG ATT GGA GTT ATT AGT ACT TAC TAT GGT GAT GCT AGC TAC
his ala lys ser leu glu trp ile gly val ile ser thr tyr tyr gly asp ala ser tyr AAC CAG AAG TTC AAG GGC AAG GCC ACA ATG ACT GTA GAC AAA TCC TCC AGC ACA GCC TAT
asn gln lys phe lys gly lys ala thr met thr val asp lys ser ser ser thr ala tyr
<u>                 CDR 2                                                      </u>

ATG GAA CTT GCC AGA CTG ACA TCT GAG GAT TCT GCC ATC TAT TAC TGT GCA AGA GGG GCT
met glu leu ala arg leu thr ser glu asp ser ala ile tyr tyr cys ala arg gly ala ACT ATG TCC TAC TTT GAC TAC TGG GGC CAA GTG ACC GTC TCC TCA ggt gga
thr met ser tyr phe asp tyr trp gly gln val thr val ser ser gly gly
<u>              CDR 3                                               </u>

FIG. 11b ggc ggt tca ggc gga gtt ggc tct ggc ggt ggc gga tcg GAC ATC GAG CTC ACT CAG TCT
gly gly ser gly gly val gly ser gly gly gly gly ser asp ile glu leu thr gln ser
                      Linker CCA GCA ATC ATG TCT GCA TCT CCA GGG GAG AAG GTC ACC ATG ACC TGC AGT GCC AGC TCA
pro ala ile met ser ala ser pro gly glu lys val thr met thr cys ser ala ser ser
                                                                    <u>CDR 1  </u>

AGT ATA AGT TAC ATG CAC TGG TAC CAG CAG AAG CCA GGC ACC TCC CCC AAA AGA TGG ATT
ser ile ser tyr met his trp tyr gln gln lys pro gly thr ser pro lys arg trp ile
<u>       CDR 1                                                                </u>

TAT GAC ACA TCC AAA CTG GCT TCT GGA GTC CCT GCT CGC TTC AGT GGC AGT GGG TCT GGG
tyr asp thr ser lys leu ala ser gly val pro ala arg phe ser gly ser gly ser gly
<u>      CDR 2                                                                 </u>

ACC TCT TAT TCT CTC ACA ATC AGC AGC ATG GAG GCT GAA GAT GCT GCC ACT TAT TAC TGC
thr ser tyr ser leu thr ile ser ser met glu ala glu asp ala ala thr tyr tyr cys CAT CAG CGG AGT AGT TAC CCA TTC ACG TTC GGA GGG GCC AAG CTG GAA ATA AAA
his gln arg ser ser tyr pro phe thr phe gly gly gly ala lys leu glu ile lys
<u>        CDR 3                                                          </u>

HUMAN PrP 106-126: KTNMKHMAGAAAAGAVVGGLG
MOUSE PrP 105-125: KTNLKHVAGAAAAGAVVGGLG

SEQUENCE LISTING

<160> NUMBER OF SEQ ID NOS: 29

<210> SEQ ID NO 1
<211> LENGTH: 4
<212> TYPE: PRT
<213> ORGANISM: Artificial
<220> FEATURE:
<223> OTHER INFORMATION: Synthetic peptide

<400> SEQUENCE: 1

Glu Phe Arg His
1

<210> SEQ ID NO 2
<211> LENGTH: 15
<212> TYPE: PRT
<213> ORGANISM: Artificial
<220> FEATURE:
<223> OTHER INFORMATION: Synthetic peptide

<400> SEQUENCE: 2

Gly Gly Gly Gly Ser Gly Gly Gly Ser Gly Gly Gly Gly Ser
1               5                   10                  15

<210> SEQ ID NO 3
<211> LENGTH: 43
<212> TYPE: PRT
<213> ORGANISM: Artificial
<220> FEATURE:
<223> OTHER INFORMATION: Synthetic peptide

```
<400> SEQUENCE: 3

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val Ile Ala Thr
            35                  40

<210> SEQ ID NO 4
<211> LENGTH: 4
<212> TYPE: PRT
<213> ORGANISM: Artificial
<220> FEATURE:
<223> OTHER INFORMATION: Synthetic peptide

<400> SEQUENCE: 4

Trp Val Leu Asp
1

<210> SEQ ID NO 5
<211> LENGTH: 717
<212> TYPE: DNA
<213> ORGANISM: Homo sapiens
<220> FEATURE:
<221> NAME/KEY: CDS
<222> LOCATION: (1)..(717)
<223> OTHER INFORMATION:

<400> SEQUENCE: 5
```

| | | | | | | | | | | | | | | | | |
|---|---|---|---|---|---|---|---|---|---|---|---|---|---|---|---|---|
| cag | gtc | aaa | ctg | cag | gag | tca | ggg | gct | gag | ctg | gtg | agg | cct | ggg | gtc | 48 |
| Gln | Val | Lys | Leu | Gln | Glu | Ser | Gly | Ala | Glu | Leu | Val | Arg | Pro | Gly | Val | |
| 1 | | | | 5 | | | | | 10 | | | | | 15 | | |
| tca | gtg | aag | att | tcc | tgc | aag | ggt | tct | ggc | tac | aca | ttc | act | gat | tat | 96 |
| Ser | Val | Lys | Ile | Ser | Cys | Lys | Gly | Ser | Gly | Tyr | Thr | Phe | Thr | Asp | Tyr | |
| | | | 20 | | | | | 25 | | | | | 30 | | | |
| gct | atg | cac | tgg | gtg | aag | cag | agt | cat | gca | aag | agt | cta | gag | tgg | att | 144 |
| Ala | Met | His | Trp | Val | Lys | Gln | Ser | His | Ala | Lys | Ser | Leu | Glu | Trp | Ile | |
| | | | 35 | | | | | 40 | | | | | 45 | | | |
| gga | gtt | att | agt | act | tac | tat | ggt | gat | gct | agc | tac | aac | cag | aag | ttc | 192 |
| Gly | Val | Ile | Ser | Thr | Tyr | Tyr | Gly | Asp | Ala | Ser | Tyr | Asn | Gln | Lys | Phe | |
| | 50 | | | | | 55 | | | | | 60 | | | | | |
| aag | ggc | aag | gcc | aca | atg | act | gta | gac | aaa | tcc | tcc | agc | aca | gcc | tat | 240 |
| Lys | Gly | Lys | Ala | Thr | Met | Thr | Val | Asp | Lys | Ser | Ser | Ser | Thr | Ala | Tyr | |
| 65 | | | | | 70 | | | | | 75 | | | | | 80 | |
| atg | gaa | ctt | gcc | aga | ctg | aca | tct | gag | gat | tct | gcc | atc | tat | tac | tgt | 288 |
| Met | Glu | Leu | Ala | Arg | Leu | Thr | Ser | Glu | Asp | Ser | Ala | Ile | Tyr | Tyr | Cys | |
| | | | | 85 | | | | | 90 | | | | | 95 | | |
| gca | aga | ggg | gct | act | atg | tcc | tac | ttt | gac | tac | tgg | ggc | caa | gtg | acc | 336 |
| Ala | Arg | Gly | Ala | Thr | Met | Ser | Tyr | Phe | Asp | Tyr | Trp | Gly | Gln | Val | Thr | |
| | | | 100 | | | | | 105 | | | | | 110 | | | |
| acg | gtc | acc | gtc | tcc | tca | ggt | gga | ggc | ggt | tca | ggc | gga | gtt | ggc | tct | 384 |
| Thr | Val | Thr | Val | Ser | Ser | Gly | Gly | Gly | Gly | Ser | Gly | Gly | Val | Gly | Ser | |
| | | | 115 | | | | | 120 | | | | | 125 | | | |
| ggc | ggt | ggc | gga | tcg | gac | atc | gag | ctc | act | cag | tct | cca | gca | atc | atg | 432 |
| Gly | Gly | Gly | Gly | Ser | Asp | Ile | Glu | Leu | Thr | Gln | Ser | Pro | Ala | Ile | Met | |
| | | 130 | | | | | 135 | | | | | 140 | | | | |
| tct | gca | tct | cca | ggg | gag | aag | gtc | acc | atg | acc | tgc | agt | gcc | agc | tca | 480 |
| Ser | Ala | Ser | Pro | Gly | Glu | Lys | Val | Thr | Met | Thr | Cys | Ser | Ala | Ser | Ser | |
| 145 | | | | | 150 | | | | | 155 | | | | | 160 | |
| agt | ata | agt | tac | atg | cac | tgg | tat | cag | cag | aag | cca | ggc | acc | tcc | ccc | 528 |
| Ser | Ile | Ser | Tyr | Met | His | Trp | Tyr | Gln | Gln | Lys | Pro | Gly | Thr | Ser | Pro | |
| | | | | 165 | | | | | 170 | | | | | 175 | | |

-continued

```
aaa aga tgg att tat gac aca tcc aaa ctg gct tct gga gtc cct gct      576
Lys Arg Trp Ile Tyr Asp Thr Ser Lys Leu Ala Ser Gly Val Pro Ala
        180                 185                 190 cgc ttc agt ggc agt ggg tct ggg acc tct tat tct ctc aca atc agc      624
Arg Phe Ser Gly Ser Gly Ser Gly Thr Ser Tyr Ser Leu Thr Ile Ser
            195                 200                 205 agc atg gag gct gaa gat gct gcc act tat tac tgc cat cag cgg agt      672
Ser Met Glu Ala Glu Asp Ala Ala Thr Tyr Tyr Cys His Gln Arg Ser
        210                 215                 220 agt tac cca ttc acg ttc gga ggg ggg gcc aag ctg gaa ata aaa          717
Ser Tyr Pro Phe Thr Phe Gly Gly Gly Ala Lys Leu Glu Ile Lys
225                 230                 235

<210> SEQ ID NO 6
<211> LENGTH: 239
<212> TYPE: PRT
<213> ORGANISM: Homo sapiens

<400> SEQUENCE: 6

Gln Val Lys Leu Gln Glu Ser Gly Ala Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Val Ile Ser Thr Tyr Tyr Gly Asp Ala Ser Tyr Asn Gln Lys Phe
    50                  55                  60

Lys Gly Lys Ala Thr Met Thr Val Asp Lys Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Arg Gly Ala Thr Met Ser Tyr Phe Asp Tyr Trp Gly Gln Val Thr
            100                 105                 110

Thr Val Thr Val Ser Ser Gly Gly Gly Gly Ser Gly Gly Val Gly Ser
        115                 120                 125

Gly Gly Gly Gly Ser Asp Ile Glu Leu Thr Gln Ser Pro Ala Ile Met
    130                 135                 140

Ser Ala Ser Pro Gly Glu Lys Val Thr Met Thr Cys Ser Ala Ser Ser
145                 150                 155                 160

Ser Ile Ser Tyr Met His Trp Tyr Gln Gln Lys Pro Gly Thr Ser Pro
                165                 170                 175

Lys Arg Trp Ile Tyr Asp Thr Ser Lys Leu Ala Ser Gly Val Pro Ala
            180                 185                 190

Arg Phe Ser Gly Ser Gly Ser Gly Thr Ser Tyr Ser Leu Thr Ile Ser
        195                 200                 205

Ser Met Glu Ala Glu Asp Ala Ala Thr Tyr Tyr Cys His Gln Arg Ser
    210                 215                 220

Ser Tyr Pro Phe Thr Phe Gly Gly Gly Ala Lys Leu Glu Ile Lys
225                 230                 235

<210> SEQ ID NO 7
<211> LENGTH: 6
<212> TYPE: PRT
<213> ORGANISM: Artificial
<220> FEATURE:
<223> OTHER INFORMATION: Synthetic peptide

<400> SEQUENCE: 7
```

-continued

Tyr Tyr Glu Phe Arg His
1               5

<210> SEQ ID NO 8
<211> LENGTH: 15
<212> TYPE: PRT
<213> ORGANISM: Artificial
<220> FEATURE:
<223> OTHER INFORMATION: Synthetic peptide

<400> SEQUENCE: 8

Val His Glu Pro His Glu Phe Arg His Val Ala Leu Asn Pro Val
1               5                   10                  15

<210> SEQ ID NO 9
<211> LENGTH: 3
<212> TYPE: PRT
<213> ORGANISM: Artificial
<220> FEATURE:
<223> OTHER INFORMATION: Synthetic peptide

<400> SEQUENCE: 9

Lys Leu His
1

<210> SEQ ID NO 10
<211> LENGTH: 45
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (17)..(17)
<223> OTHER INFORMATION: n is A, C, T or G

<400> SEQUENCE: 10
cccccctccg aacgtsnatg ggtaactcga tcgctgatgg cagta                45

<210> SEQ ID NO 11
<211> LENGTH: 24
<212> TYPE: DNA
<213> ORGANISM: Artificial
<220> FEATURE:
<223> OTHER INFORMATION: Primer

<400> SEQUENCE: 11
atctatgcgg cccagccggc catg                                       24

<210> SEQ ID NO 12
<211> LENGTH: 38
<212> TYPE: DNA
<213> ORGANISM: Artificial
<220> FEATURE:
<223> OTHER INFORMATION: Primer

<400> SEQUENCE: 12
gtggtgctga gtggatccta tactacactg ccaccggg                        38

<210> SEQ ID NO 13
<211> LENGTH: 58
<212> TYPE: DNA
<213> ORGANISM: Artificial
<220> FEATURE:
<223> OTHER INFORMATION: Primer

<400> SEQUENCE: 13

-continued

```
agctccgatg ctgaattcgg tgatagcggc tacgaagtgc atcatcagaa acctgcag        58
```

<210> SEQ ID NO 14
<211> LENGTH: 52
<212> TYPE: DNA
<213> ORGANISM: Artificial
<220> FEATURE:
<223> OTHER INFORMATION: Primer

<400> SEQUENCE: 14

```
ggtttctgat gatgcacttc gtagccgcta tcatgacgaa attcagcatc gg        52
```

<210> SEQ ID NO 15
<211> LENGTH: 9
<212> TYPE: PRT
<213> ORGANISM: Artificial
<220> FEATURE:
<223> OTHER INFORMATION: Synthetic peptide

<400> SEQUENCE: 15

His Gln Arg Ser Ser Tyr Pro Cys Thr
1               5

<210> SEQ ID NO 16
<211> LENGTH: 9
<212> TYPE: PRT
<213> ORGANISM: Artificial
<220> FEATURE:
<223> OTHER INFORMATION: Synthetic peptide

<400> SEQUENCE: 16

His Gln Arg Ser Ser Tyr Pro Cys Thr
1               5

<210> SEQ ID NO 17
<211> LENGTH: 9
<212> TYPE: PRT
<213> ORGANISM: Artificial
<220> FEATURE:
<223> OTHER INFORMATION: Synthetic peptide

<400> SEQUENCE: 17

His Gln Arg Ser Ser Tyr Pro Phe Thr
1               5

<210> SEQ ID NO 18
<211> LENGTH: 9
<212> TYPE: PRT
<213> ORGANISM: Artificial
<220> FEATURE:
<223> OTHER INFORMATION: Synthetic peptide

<400> SEQUENCE: 18

His Gln Arg Ser Ser Tyr Pro Tyr Thr
1               5

<210> SEQ ID NO 19
<211> LENGTH: 9
<212> TYPE: PRT
<213> ORGANISM: Artificial
<220> FEATURE:
<223> OTHER INFORMATION: Synthetic peptide

<400> SEQUENCE: 19

His Gln Arg Ser Ser Tyr Pro Phe Thr
1               5

<210> SEQ ID NO 20
<211> LENGTH: 9
<212> TYPE: PRT
<213> ORGANISM: Artificial
<220> FEATURE:
<223> OTHER INFORMATION: Synthetic peptide

<400> SEQUENCE: 20

His Gln Arg Ser Ser Tyr Pro Ser Thr
1               5

<210> SEQ ID NO 21
<211> LENGTH: 15
<212> TYPE: PRT
<213> ORGANISM: Artificial
<220> FEATURE:
<223> OTHER INFORMATION: Synthetic peptide

<400> SEQUENCE: 21

Asp Thr Glu Phe Arg His Ser Ser Asn Asn Phe Ser Ala Val Arg
1               5                   10                  15

<210> SEQ ID NO 22
<211> LENGTH: 15
<212> TYPE: PRT
<213> ORGANISM: Artificial
<220> FEATURE:
<223> OTHER INFORMATION: Synthetic peptide

<400> SEQUENCE: 22

Ser Thr Glu Phe Arg His Gln Thr Thr Pro Leu His Pro Asn Ser
1               5                   10                  15

<210> SEQ ID NO 23
<211> LENGTH: 15
<212> TYPE: PRT
<213> ORGANISM: Artificial
<220> FEATURE:
<223> OTHER INFORMATION: Synthetic peptide

<400> SEQUENCE: 23

Lys Glu Pro Arg His His Ile Gln His His Glu Arg Val Ile Arg
1               5                   10                  15

<210> SEQ ID NO 24
<211> LENGTH: 15
<212> TYPE: PRT
<213> ORGANISM: Artificial
<220> FEATURE:
<223> OTHER INFORMATION: Synthetic peptide

<400> SEQUENCE: 24

Ser Ala Ala Asp Phe Arg His Gly Ser Pro Pro Ile Ser Ala Phe
1               5                   10                  15

<210> SEQ ID NO 25
<211> LENGTH: 21
<212> TYPE: PRT
<213> ORGANISM: Artificial
<220> FEATURE:
<223> OTHER INFORMATION: Synthetic peptide

<400> SEQUENCE: 25

Lys Thr Asn Met Lys His Met Ala Gly Ala Ala Ala Ala Gly Ala Val
1               5                   10                  15

<210> SEQ ID NO 26
<211> LENGTH: 4
<212> TYPE: PRT
<213> ORGANISM: Artificial
<220> FEATURE:
<223> OTHER INFORMATION: Synthetic peptide

<400> SEQUENCE: 26

Asp Met Lys His
1

<210> SEQ ID NO 27
<211> LENGTH: 357
<212> TYPE: DNA
<213> ORGANISM: Artificial
<220> FEATURE:
<223> OTHER INFORMATION: Synthetic construct
<220> FEATURE:
<221> NAME/KEY: CDS
<222> LOCATION: (1)..(357)
<223> OTHER INFORMATION:

<400> SEQUENCE: 27

```
ggc ggt tca ggc gga gtt ggc tct ggc ggt ggc gga tcg gac atc gag      48
Gly Gly Ser Gly Gly Val Gly Ser Gly Gly Gly Gly Ser Asp Ile Glu
1               5                   10                  15 ctc act cag tct cca gca atc atg tct gca tct cca ggg gag aag gtc      96
Leu Thr Gln Ser Pro Ala Ile Met Ser Ala Ser Pro Gly Glu Lys Val
            20                  25                  30 acc atg acc tgc agt gcc agc tca agt ata agt tac atg cac tgg tat     144
Thr Met Thr Cys Ser Ala Ser Ser Ser Ile Ser Tyr Met His Trp Tyr
        35                  40                  45 cag cag aag cca ggc acc tcc ccc aaa aga tgg att tat gac aca tcc     192
Gln Gln Lys Pro Gly Thr Ser Pro Lys Arg Trp Ile Tyr Asp Thr Ser
    50                  55                  60 aaa ctg gct tct gga gtc cct gct cgc ttc agt ggc agt ggg tct ggg     240
Lys Leu Ala Ser Gly Val Pro Ala Arg Phe Ser Gly Ser Gly Ser Gly
65                  70                  75                  80 acc tct tat tct ctc aca atc agc agc atg gag gct gaa gat gct gcc     288
Thr Ser Tyr Ser Leu Thr Ile Ser Ser Met Glu Ala Glu Asp Ala Ala
                85                  90                  95 act tat tac tgc cat cag cgg agt agt tac cca ttc acg ttc gga ggg     336
Thr Tyr Tyr Cys His Gln Arg Ser Ser Tyr Pro Phe Thr Phe Gly Gly
            100                 105                 110 ggg gcc aag ctg gaa ata aaa                                          357
Gly Ala Lys Leu Glu Ile Lys
        115
```

<210> SEQ ID NO 28
<211> LENGTH: 119
<212> TYPE: PRT
<213> ORGANISM: Artificial
<220> FEATURE:
<223> OTHER INFORMATION: Synthetic construct

<400> SEQUENCE: 28

Gly Gly Ser Gly Gly Val Gly Ser Gly Gly Gly Gly Ser Asp Ile Glu
1               5                   10                  15

Leu Thr Gln Ser Pro Ala Ile Met Ser Ala Ser Pro Gly Glu Lys Val
            20                  25                  30

Thr Met Thr Cys Ser Ala Ser Ser Ser Ile Ser Tyr Met His Trp Tyr

-continued

```
                35                  40                  45
Gln Gln Lys Pro Gly Thr Ser Pro Lys Arg Trp Ile Tyr Asp Thr Ser
         50                  55                  60

Lys Leu Ala Ser Gly Val Pro Ala Arg Phe Ser Gly Ser Gly Ser Gly
 65                  70                  75                  80

Thr Ser Tyr Ser Leu Thr Ile Ser Ser Met Glu Ala Glu Asp Ala Ala
                 85                  90                  95

Thr Tyr Tyr Cys His Gln Arg Ser Ser Tyr Pro Phe Thr Phe Gly Gly
            100                 105                 110

Gly Ala Lys Leu Glu Ile Lys
            115

<210> SEQ ID NO 29
<211> LENGTH: 21
<212> TYPE: PRT
<213> ORGANISM: Mus sp.

<400> SEQUENCE: 29

Lys Thr Asn Leu Lys His Val Ala Gly Ala Ala Ala Ala Gly Ala Val
 1               5                  10                  15

Val Gly Gly Leu Gly
             20
```

BACTERIOPHAGE DISPLAYING Aβ EPITOPES AND METHOD OF USE

REFERENCE TO RELATED APPLICATIONS

The present application is the national stage under 35 U.S.C. 371 of international application PCT/IL00/00518, filed 31 Aug. 2000, which designated the United States, and which international application was published under PCT Article 21(2) in the English language and whose content is incorporated herein entirely by reference.

FIELD AND BACKGROUND OF THE INVENTION

The present invention relates to agents and compositions and to methods of utilizing same for treating plaque-forming diseases. More particularly, the methods according to the present invention involve the use of (i) plaque derived antigens cloned and displayed on the surface of a display vehicle for in vivo elicitation of antibodies capable of preventing plaque formation and of disaggregating existing plaques; and (ii) antibodies raised against plaque derived antigens, at least an immunologic portion of which is cloned and displayed on a display vehicle, which immunologic portion is capable of preventing plaque formation and of disaggregating existing plaques. The present invention further relates to a method of targeting a display vehicle to the brain of an animal, including man and to a method for detecting the presence of plaque forming prions.

Plaques forming diseases are characterized by the presence of amyloid plaques deposits in the brain as well as neuronal degeneration. Amyloid deposits are formed by peptide aggregated to an insoluble mass. The nature of the peptide varies in different diseases but in most cases, the aggregate has a beta-pleated sheet structure and stains with Congo Red dye. In addition to Alzheimer's disease (AD), early onset Alzheimer's disease, late onset Alzheimer's disease, presymptomatic Alzheimer's disease, other diseases characterized by amyloid deposits are, for example, SAA amyloidosis, hereditary Icelandic syndrome, multiple myeloma, and prion diseases. The most common prion diseases in animals are scrapie of sheep and goats and bovine spongiform encephalopathy (BSE) of cattle (Wilesmith et al, 1991). Four prion diseases have been identified in humans: (i) kuru, (ii) Creutzfeldt-Jakob Disease (CJD), (iii) Gerstmann-Streussler-Sheinker Disease (GSS), and (iv) fatal familial insomnia (FFI) (Gajdusek, 1977; Medori et al, 1992).

Etiology of Prion Diseases

Prion diseases involve conversion of the normal cellular prion protein ($PrP^C$) into the corresponding scrapie isoform ($PrP^{Sc}$). Spectroscopic measurements demonstrate that the conversion of $PrP^C$ into the scrapie isoform ($PrP^{Sc}$) involves a major conformational transition, implying that prion diseases, like other amyloidogenic diseases, are disorders of protein conformation. The transition from $PrP^C$ to $PrP^{Sc}$ is accompanied by a decrease in α-helical secondary structure (from 42% to 30%) and a remarkable increase in β-sheet content (from 3% to 43%) (Caughey et al, 1991; Pan et al, 1993). This rearrangement is associated with abnormal physiochemical properties, including insolubility in non-denaturing detergents and partial resistance to proteolysis. Previous studies have shown that a synthetic peptide homologous with residues 106–126 of human PrP (PrP106–126) exhibits some of the pathogenic and physicochemical properties of $PrP^{Sc}$ (Selvaggini et al, 1993; Tagliavini et al, 1993; Forloni et al, 1993). The peptide shows a remarkable conformational polymorphism, acquiring different secondary structures in various environments (De Gioia et al, 1994). It tends to adopt a β-sheet conformation in buffered solutions, and aggregates into amyloid fibrils that are partly resistant to digestion with protease. Recently, the X-ray crystallographic studies of a complex of antibody 3F4 and its peptide epitope (PrP 104–113) provided a structural view of this flexible region that is thought to be a component of the conformational rearrangement essential to the development of prion disease (Kanyo et al, 1999). The identification of classes of sequences that participate in folding-unfolding and/or solubilization-aggregation processes may open new direction for the treatment of plaque forming disease, based on the prevention of aggregation and/or the induction of disaggregation (Silen et al, 1989; Frenkel et al, 1998; Horiuchi and Caughey, 1999).

Alzheimer'8 Disease—Clinical Overview

Alzheimer's disease (AD) is a progressive disease resulting in senile dementia. Broadly speaking, the disease falls into two categories: late onset, which occurs in old age (typically above 65 years) and early onset, which develops well before the senile period, e.g., between 35 and 60 years. In both types of the disease, the pathology is similar, but the abnormalities tend to be more severe and widespread in cases beginning at an earlier age. The disease is characterized by two types of lesions in the brain, senile plaques and neurofibrillary tangles. Senile plaques are areas of disorganized neutrophils up to 150 mm across with extracellular amyloid deposits at the center, visible by microscopic analysis of sections of brain tissue. Neurofibrillary tangles are intracellular deposits of tau protein consisting of two filaments twisted about each other in pairs.

Senile Plaques and Other Amyloid Plaques

The principal constituent of the senile plaques is a peptide termed Aβ or beta-amyloid peptide (βAP or βA). The abbreviations Aβ and βA are used interchangeably throughout the present specification. The amyloid beta peptide is an internal fragment of 39–43 amino acids of a precursor protein termed amyloid precursor protein (APP). Several mutations within the APP protein have been correlated with the presence of Alzheimer's disease (See, e.g., Goate et al, 1991, valine$^{717}$ to isoleucine; Chartier-Harlin et al, 1991, valine$^{717}$ to glycine; Murrell et al, 1991, valine717 to phenylalanine; Mullan et al, 1992, a double mutation, changing lysine$^{595}$-methionine$^{596}$ to asparagine$^{595}$-leucine$^{596}$).

Such mutations are thought to cause Alzheimer's disease by increased or altered processing of APP to beta-amyloid, particularly processing of APP to increased amounts of the long form of beta-amyloid (i.e., Aβ1–42 and Aβ1–43). Mutations in other genes, such as the presenilin genes, PS1 and PS2, are thought indirectly to affect processing of APP to generate increased amounts of long form beta-amyloid (see Hardy J, 1997). These observations indicate that beta-amyloid, and particularly its long form, is a causative element in Alzheimer's disease.

Other peptides or proteins with evidence of self aggregation are also known, such as, but not limited to, amylin (Young et al, 1994); bombesin, caerulein, cholecystokinin octapeptide, eledoisin, gastrin-related pentapeptide, gastrin tetrapeptide, somatostatin (reduced), substance P; and peptide, luteinizing hormone releasing hormone, somatostatin N-Tyr (Banks et al, 1992).

Binding of high affinity monoclonal antibodies (mAbs) to such regions may alter the molecular dynamics of the whole protein chain or assembly. By appropriate selection, mAbs have been found to recognize incompletely folded epitopes and to induce native conformation in partially or wrongly folded protein (Frauenfelder et al, 1979, Blond et al 1987; Karplus et al, 1990; Carlson et al, 1992; Solomon et al, 1995).

Treatment

U.S. Pat. No. 5,688,561 to Solomon teaches methods of identifying monoclonal antibodies effective in disaggregating protein aggregates and preventing aggregation of such proteins. Specifically, U.S. Pat. No. 5,688,561 demonstrates anti-beta-amyloid monoclonal antibodies effective in disaggregating beta-amyloid plaques and preventing beta-amyloid plaque formation in vitro. U.S. Pat. No. 5,688,561 stipulates the in vivo use of such antibodies to prevent plaque formation by aggregation of beta-amyloid or to disaggregate beta-amyloid plaques that have already formed. These teachings do not, however, identify an epitope to be employed to generate such antibodies. In addition, these teachings do not provide means with which to enable the penetration of such antibodies into the brain through the blood brain barrier (BBB). Furthermore, this patent fails to teach the use of phage display technology as a delivery method for antigens or antibodies. Yet furthermore, no experimental results demonstrating the in vivo effectiveness of such antibodies are demonstrated by U.S. Pat. No. 5,688,561.

EP 526511 by McMichael teaches administration of homeopathic dosages (less than or equal to $11^{-2}$ mg/day) of beta-amyloid to patients with pre-established AD. In a typical human with about 5 liters of plasma, even the upper limit of this dosage would be expected to generate a concentration of no more than 2 pg/ml. The normal concentration of beta-amyloid in human plasma is typically in the range of 50–200 pg/ml (Seubert et al, 1992). Because this proposed dosage would barely alter the level of endogenous circulating beta-amyloid and because EP 526511 does not recommend the use of an adjuvant, it seems implausible that any therapeutic benefit would result therefrom.

PCT/US98/25386 by Schenk and a *Nature* paper by Schenk et al (1999) teach administration of beta-amyloid immunogens to a patient in order to generate antibodies to prevent formation of plaques or dissolve existing plaques. According to Schenk, 50 to 100 mg of antigen are required, 1 to 10 mg if an adjuvant is employed. These teachings also stipulate that a similar effect may be achieved by direct administration of antibodies against beta-amyloid, in both cases disregarding the blood brain barrier that, under normal circumstances, prevents the penetration of antibodies into the brain.

It is also important to note that these teachings are typically restricted to the use of " . . . any of the naturally occurring forms of beta-amyloid peptide, and particularly the human forms (i.e., Aβ39, Aβ40, Aβ41, Aβ42 or Aβ43)" or " . . . longer polypeptides that include, for example, a beta-amyloid peptide, active fragment or analog together with other amino acids", or "multimers of monomeric immunogenic agents".

These teachings ignore, however, earlier data teaching that the first 28 amino acids of beta-amyloid are sufficient to elicit antibodies which both disaggregate and inhibit aggregation of beta-amyloid plaques in vitro (Hanan et al, 1996; Solomon et al, 1996; Solomon et al, 1997).

Schenk and Schenk et al both fail to teach the use of the N-terminal epitope of beta-amyloid plaques which is known to be a sequential epitope composed of only four amino acid residues (EFRH, SEQ ID NO:1) located at positions 3–6 of the beta-amyloid peptide (Frenkel et al, 1998). Antibodies against this epitope have subsequently been shown to disaggregate beta-amyloid fibrils, restore beta-amyloid plaques solubilization and prevent neurotoxic effects on PC 12 cells (Solomon et al, 1997; and Solomon et al, 1996).

This epitope has been independently confirmed as the epitope bound by anti-aggregating antibodies using random combinatorial hexapeptide phage display (Frenkel et al, 1998).

The EFRH (SEQ ID NO:1) epitope is available for antibody binding when beta-amyloid peptide is either in solution or in aggregates. Blocking of this epitope by a monoclonal antibody prevents self-aggregation and enables resolubilization of already formed aggregates.

These findings suggest that the teachings of Schenk and colleagues are inefficient at best. Since, as has already been mentioned hereinabove, the normal concentration of beta-amyloid in human serum is 50–200 pg/ml, immunization with that peptide could be expected to produce either low antibody titers or high toxicity if strong adjuvants are used and as such it is not applicable for therapy. Indeed, in order to achieve significant serum titers of antibody against beta-amyloid a series of 11 monthly injections was required (Schenk et al, 1999). The degree to which these serum titers will persist over time is not yet known, and this point is especially crucial with respect to early onset Alzheimer's disease.

Schenk and colleagues further teach that an immunogenic peptide such as beta-amyloid may be displayed upon the surface of a virus or bacteria. However, they fail to teach use of an antigen so displayed to effect immunization. No mention is made of defining an epitope in this context and no experimental data is provided either. In addition, delivery of antibody displayed on a display vehicle is not taught by Schenk or Schenk et al altogether.

Collectively, the prior art fails to teach means with which an effective titer of anti-aggregation antibodies can be generated in vivo in a short time and/or be introduced into the brains of patients suffering a plaque-forming diseases. In addition, the persistence of titers generated via prior art teachings has not been established.

There is thus a widely recognized need for, and it would be highly advantageous to have, effective means of disaggregating amyloid plaques in vivo which would have lasting effect, high efficiency, rapid onset, no adverse effect on the treated subject and which is readily amenable to large scale production.

SUMMARY OF THE INVENTION

According to one aspect of the present invention there is provided a method of treating a plaque forming disease comprising the steps of (a) displaying a polypeptide on a display vehicle, the polypeptide representing at least one epitope of an aggregating protein associated with plaque formation in the plaque forming disease, the at least one epitope being capable of eliciting antibodies capable of disaggregating the aggregating protein and/or of preventing aggregation of the aggregating protein; and (b) introducing the display vehicle into a body of a recipient so as to elicit the antibodies capable of disaggregating the aggregating protein and/or of preventing aggregation of the aggregating protein.

According to another aspect of the present invention there is provided an agent for treating a plaque forming disease comprising a display vehicle displaying a polypeptide representing at least one epitope of an aggregating protein associated with plaque formation in the plaque forming disease, the at least one epitope being capable of eliciting antibodies capable of disaggregating the aggregating protein and/or of preventing aggregation of the aggregating protein.

According to yet another aspect of the present invention there is provided a pharmaceutical composition for treating a plaque forming disease comprising an effective amount of a display vehicle displaying a polypeptide, the polypeptide representing at least one epitope of an aggregating protein associated with plaque formation in the plaque forming disease, the at least one epitope being capable of eliciting an effective amount of antibodies capable of disaggregating the aggregating protein and/or of preventing aggregation of the aggregating protein, the pharmaceutical composition further comprising a pharmaceutically acceptable carrier.

According to still another aspect of the present invention there is provided a method of preparing a display vehicle for treating a plaque forming disease, the method comprising the step of genetically modifying a genome of a display vehicle by inserting therein a polynucleotide sequence encoding a polypeptide representing at least one epitope of an aggregating protein associated with plaque formation in the plaque forming disease, the at least one epitope being capable of eliciting antibodies capable of disaggregating the aggregating protein and/or of preventing aggregation of the aggregating protein, such that when the display vehicle propagates the polypeptide is displayed by the display vehicle.

According to an additional aspect of the present invention there is provided a method of treating a plaque forming disease comprising the steps of (a) displaying a polypeptide representing at least an immunological portion of an antibody being for binding at least one epitope of an aggregating protein associated with plaque formation in the plaque forming disease, the binding capable of disaggregating the aggregating protein and/or of preventing aggregation of the aggregating protein; and (b) introducing the display vehicle into a body of a recipient so as to disaggregate the aggregating protein and/or prevent its aggregation.

According to still an additional aspect of the present invention there is provided a method of introducing a display vehicle lacking an engineered targeting moiety into a brain of a recipient, the method comprising the step of administering the display vehicle intranasally to the recipient.

According to further features in preferred embodiments of the invention described below, the step of introducing the display vehicle into the body of the recipient so as to disaggregate the aggregating protein is effected through an olfactory system of the recipient.

According to yet another additional aspect of the present invention there is provided an agent for treating a plaque forming disease comprising a display vehicle displaying a polypeptide representing at least an immunological portion of an antibody which can bind at least one epitope of an aggregating protein associated with plaque formation in the plaque forming disease, the immunological portion of the antibody being capable of disaggregating said aggregating protein and/or of preventing aggregation of the aggregating protein.

According to yet an additional aspect of the present invention there is provided a pharmaceutical composition for treating a plaque forming disease comprising an effective amount of a display vehicle displaying a polypeptide representing at least an immunological portion of an antibody which can bind at least one epitope of an aggregating protein associated with plaque formation in the plaque forming disease, the immunological portion of the antibody being capable of disaggregating the aggregating protein and/or of preventing aggregation of the aggregating protein, the pharmaceutical composition further comprising a pharmaceutically acceptable carrier.

According to still an additional aspect of the present invention there is provided a method of preparing a display vehicle for treating a plaque forming disease comprising the step of genetically modifying a genome of a display vehicle by inserting therein a polynucleotide sequence encoding at least an immunological portion of an antibody capable of binding at least one epitope of an aggregating protein associated with plaque formation in the plaque forming disease, the immunological portion of the antibody being capable of disaggregating the aggregating protein and/or of preventing aggregation of the aggregating protein.

According to a further aspect of the present invention there is provided a polypeptide comprising at least an immunological portion of an antibody being capable disaggregating a prion protein aggregate and/or of preventing aggregation of said prion protein.

According to further features in preferred embodiments of the invention described below, the polypeptide is capable of binding at least one epitope formed by an amino acid sequence set forth in SEQ ID NO:25.

According to yet a further aspect of the present invention there is provided a method of detecting a presence or an absence of a prion protein in a biological sample, the method comprising the steps of: (a) incubating an anti-prion antibody or an immunological portion thereof with the biological sample; (b) determining a presence or an absence of antigen complexes formed with the anti-prion antibody or the immunological portion thereof, to thereby determine the presence or the absence of the prion protein in the biological sample.

According to still further features in the described preferred embodiments the plaque forming disease is selected from the group consisting of early onset Alzheimer's disease, late onset Alzheimer's disease, presymptomatic Alzheimer's disease, SAA amyloidosis, hereditary Icelandic syndrome, senility and multiple myeloma.

According to still further features in the described preferred embodiments the plaque forming disease is selected from the group consisting of scrapie, bovine spongiform encephalopathy (BSE), kuru, Creutzfeldt-Jakob Disease (CJD), Gerstmann-Streussler-Sheinker Disease (GSS) and fatal familial insomnia (FFI).

According to still further features in the described preferred embodiments the aggregating protein is selected from the group consisting of beta-amyloid, serum amyloid A, cystatin C, IgG kappa light chain and prion protein.

According to still further features in the described preferred embodiments the display vehicle is selected from the group consisting of a virus, a bacteria and a polypeptide carrier.

According to still further features in the described preferred embodiments the virus is selected from the group consisting of a double stranded DNA virus, a single stranded DNA virus, a positive strand RNA virus and a negative strand RNA virus.

According to still further features in the described preferred embodiments the display vehicle is a bacteriophage.

According to still further features in the described preferred embodiments the display vehicle is a filamentous bacteriophage.

According to still further features in the described preferred embodiments the bacteriophage display vehicle is capable of propagating within bacterial flora of the host.

According to still further features in the described preferred embodiments the bacteriophage display vehicle is capable of propagating within E. coli.

According to still further features in the described preferred embodiments the bacteriophage display vehicle is fd.

According to further features in the described preferred embodiments of the invention, the display vehicle is incapable of propagation in vivo.

According to still further features in the described preferred embodiments a triple dose of $10^{10}$ units of the chosen display vehicle induces an antibody titer of at least 1:50,000 within 30 days of administration, as measured by ELISA.

According to still further features in the described preferred embodiments the at least one epitope of said prion protein is formed by an amino acid sequence set forth in SEQ ID NO:25.

According to still further features in the described preferred embodiments the immunological portion of an antibody serves for binding at least one epitope of an aggregating protein associated with plaque formation in a plaque forming disease, said immunological portion of said antibody being capable of disaggregating said aggregating protein and/or of preventing aggregation of said aggregating protein.

According to still further features in the described preferred embodiments the prion protein is the aggregating protein associated with plaque formation.

According to still further features in the described preferred embodiments the biological sample is derived from tissues and/or body fluids of a human, a primate, a monkey, a pig, a bovine, a sheep, a deer, an elk, a cat, a dog and a chicken.

The present invention successfully addresses the shortcomings of the presently known configurations by providing methods, agents, and pharmaceutical compositions for preventing or reversing the progression of a plaque forming disease. The present invention further includes methods for preparing agents and pharmaceutical compositions useful for preventing or treating plaque-forming diseases and to a method of detecting the presence of a pathogenic prion protein in a biological sample.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show details of the invention in more detail than is necessary for a fundamental understanding of the invention, the description taken with the drawings making apparent to those skilled in the art how the several forms of the invention may be embodied in practice.

In the drawings:

FIG. 1a is a schematic depiction of an IgM antibody.

FIG. 1b is a photograph of an ethidium bromide stained 1.5% agarose gel showing cDNA fragments of the heavy and the light chains of IgM508. First lane: Kb (Ladder); second and third lanes: $V_H$ and $V_L$ fragments.

FIG. 1c is a photograph of an ethidium bromide stained 1.5% agarose gel showing scFv DNA fragment derived from antibody IgM 508.

FIG. 1d is a schematic depiction of filamentous phage displaying an scFv.

FIG. 1e is a schematic depiction of a soluble scFv.

FIGS. 11a and 11b show nucleotide (SEQ ID NO:5) and deduced amino acid (SEQ ID. NO:6) sequences of scFv 508F heavy chain (FIG. 11a); and the linker and the variable region of the light chain (FIG. 11b) (SEQ ID NOs:27 and 28). The amino acid sequence is presented by a three-letter code; CDRs and the linker are underlined.

Figure 28:
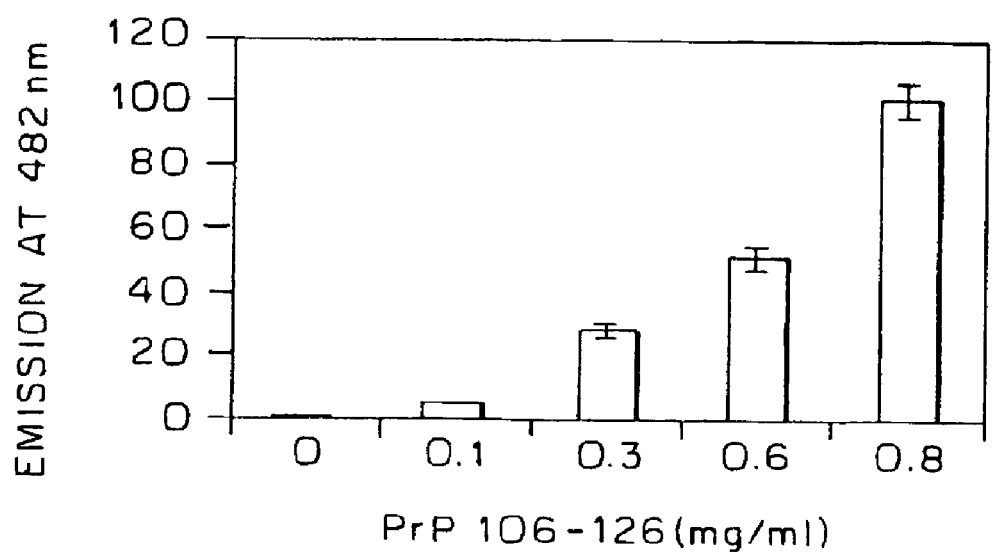

FIG. 28 illustrates the extent of aggregation of the PrP peptide, using ThT binding assay. PrP 106–126 (0–0.8 mg/ml) was incubated for 7 days at 37° C. and emission at 482 nm was measured to determine the extent of aggregation.

Figure 29:
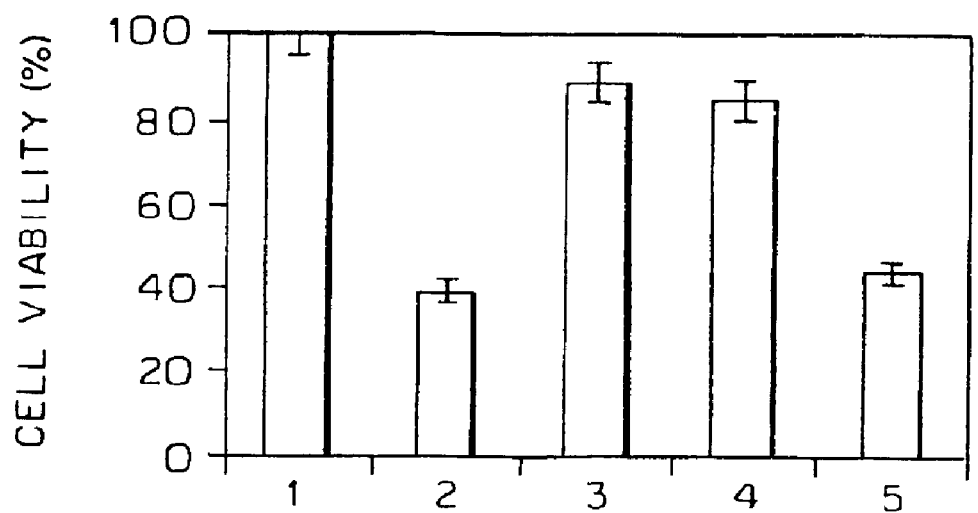

FIG. 29 demonstrates the protective effect of mAbs 3–11, 2–40 on PrP peptide neurotoxicity. PC12 cells were seeded in a 96 wells plate in a DMEM medium supplemented with 2 mM insulin 2 mM L-glutamine and 100 units penicillin/streptomycin and were incubated for three days. The following treatments were conducted: (1) Positive Control, untreated cells; (2) 100 $\mu$M PrP 106–126 that was preincubated for 7 days at 37° C.; (3, 4, 5) an aggregated peptide that was preincubated for 1 hour before exposure to the cells together with the mAbs 3–11 (treatment 3), 2–40 (treatment 4) and 3F4 (treatment 5). Cell viability was assessed using the MTT assay.

Figure 30:
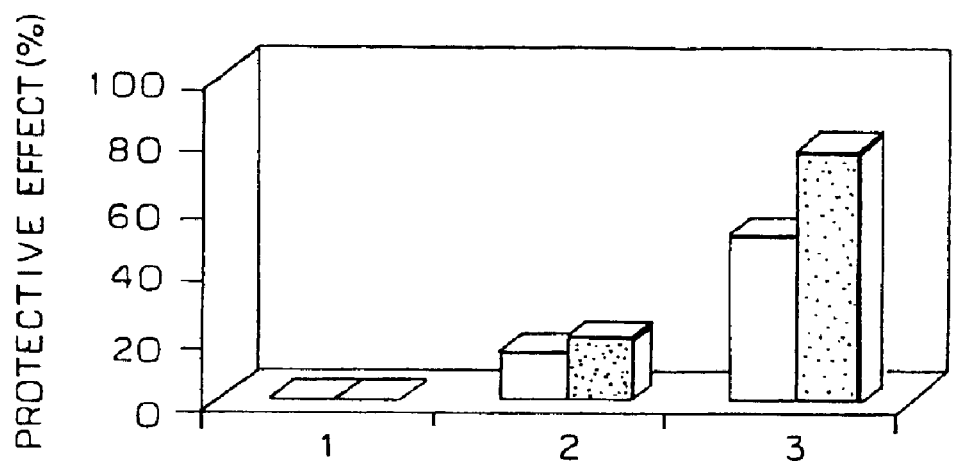

FIG. 30 illustrates the modulation of PrP conformation by the mAbs. PrP 106–126 (0.3 mg/ml) was incubated for 7 days at 37° C. (1) and with mAbs 2–40, 3–11 and 3F4 (treatments 2, 3 and 4, respectively). The antibodies were incubated with the sample for 24 hours either prior to the PrP incubation (grey bars) or following a one-week PrP incubation (white bars). Fibril formation was assessed by the ThT binding assay.

Figure 31:
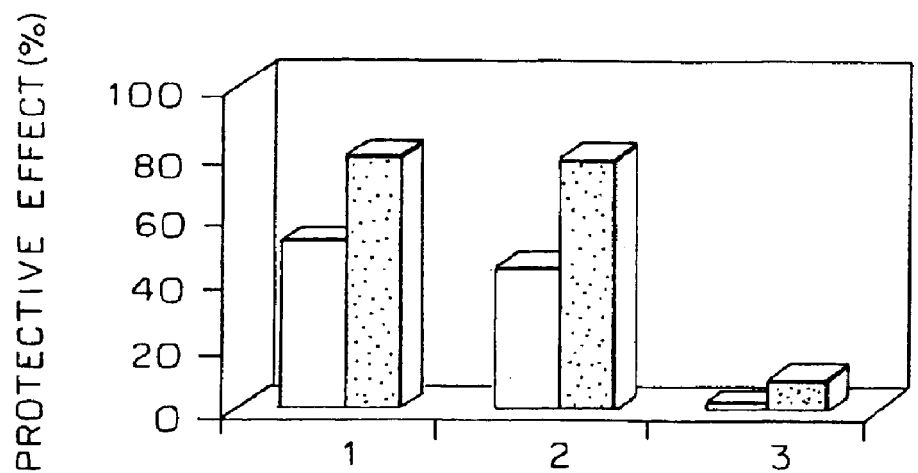

FIG. 31 shows the concentration dependent protective effect of mAb 3–11 against PrP fibrillar aggregate formation. PrP 106–126 (0.3 mg/ml) was incubated for 7 days at 37° C. with diluted mAb 3–11 (1:1, 1:10, 1:50, corresponding to treatments 1, 2, and 3, respectively). The antibody was incubated with the sample for 24 hours either prior to (grey bars), or following (white bars), the one-week incubation of PrP. Amyloid fibril formation was assessed using ThT binding assay

DESCRIPTION OF THE PREFERRED EMBODIMENTS

The present invention is of methods, pharmaceutical agents and compositions, which can be used for treating plaque-forming diseases, including, but not limited to, Alzheimer's disease and prion generated plaque-forming diseases. Specifically the present invention can be used to (i) induce active immunity to plaque derived antigens in a recipient by immunizing with at least one epitope of an aggregating protein associated with plaque formation in a plaque forming disease on a display vehicle, so that antibodies elicited in response to immunization are capable of preventing plaque formation and/or of disaggregating existing plaques; and (ii) induce passive immunity by administering at least an immunological portion of an antibody which can bind to at least one epitope of an aggregating protein associated with plaque formation in a plaque forming disease, raised against plaque derived antigens, cloned and displayed on a display vehicle, capable of preventing plaque formation and of disaggregating existing plaques. This passive immunity may be of exceptionally long duration if the display vehicle employed is capable of replicating within the recipient. The present invention further relates to a method of targeting a display vehicle to the brain of an animal, including man, so that plaques present in the brain, such as beta amyloid plaques in brains of Alzheimer's disease patients, may be disaggregated. Finally, the present invention also related to a method of detecting aggregate forming prion proteins in a biological sample.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description. The invention is capable of other embodiments or of being practiced or carried out in various ways. Also, it is to be understood that the phraseology and terminology employed herein is for the purpose of description and should not be regarded as limiting.

While reducing one aspect of the present invention to practice, as is further exemplified in Examples 1–15 of the Examples section that follows, antigens derived from beta amyloid peptide were displayed on the surface of a filamentous phage that was used for immunization of experimental animals. All of the peptides employed contained the EFRH epitope (SEQ ID NO:1, residues 3–6, SEQ ID NO:3) of beta amyloid peptide (SEQ ID NO:3). The epitope was presented as a fusion protein of fd phage coat glycoprotein III or VIII. Doses ranging from $10^{10}$ to $10^{12}$ phages per injection were employed on 8-week-old female BALB/c mice. A typical immunization schedule included three injections at 14-day intervals, administered either intraperitoneally or intranasally.

During and after the immunization process, the antibody serum titer of subject mice was tested for the production of A$\beta$ specific antibodies by enzyme linked immunosorbent assay (ELISA) as detailed in methods and materials hereinbelow. Serum titers were subsequently shown to persist for 11 months in response to a protocol including only 3 immunizations. While all tested epitopes containing EFRH (SEQ ID NO:1) produced a titer, displaying the epitope on the surface of a display vehicle produced far highest and unexpected titers. These high titers are believed to be a result of the great number of copies presented to the immune system using this method, and this idea is supported by results of binding assays using controlled amounts of sera.

The anti-aggregating properties of the obtained polyclonal antibody raised against EFRH (SEQ ID NO:1) epitopes with respect to beta-amyloid fibril formation was measured by the ThT binding assay. Serum, at dilution of 1:10 and 1:100, disrupted formation of fibril structure of $\beta$-amyloid with extensive deterioration of fibril morphology, as indicated by a substantial decrease in ThT fluorescence. The unrelated serum used as control (serum from un-immunized mouse) did not significantly inhibit fibril formation.

The effect of the same serum on disruption of already formed $\beta$A fibril (the toxic form of $\beta$AP) was also determined. Serum of EFRH (SEQ ID NO:1) immunized mice incubated with pre-formed $\beta$A fibrils disrupted the fibril structure. The unrelated control antibody had no significant effect on fibril morphology. Together, these results confirm the ability of EFRH (SEQ ID NO:1) epitope presented by suitable display vehicles to evoke production of anti-aggregation antibodies, which can inhibit or reverse the process of fibril formation.

Diluted serum produced according to this embodiment of the present invention prevented the neurotoxicity of beta amyloid peptide. This result implies potential clinical utility in preventing brain deterioration of patients suffering from amyloid plaque diseases.

While reducing another aspect of the present invention to practice, and as is further exemplified in Examples 15–21 of the Examples section which follows, it was uncovered that site-directed antibodies (designated mAbs 3–11 and 2–40), which were generated against a prion derived peptide, are useful in preventing or disaggregating prion generated plaques.

Binding of the prion-derived peptide (PrP 106–126) to these mAbs led to a significant protective effect against aggregation as was measured by the ThT and MTT assays. The mAbs generated by the preset invention also significantly decrease the peptide fibrillar aggregation and reverse the aggregated form to a disaggregated conformation as assayed by the ThT binding assay.

The binding of mAbs 3–11 and 2–40 to the PrP peptide either in solution or to the aggregate suggests that this epitope is involved in aggregation process and may act as a regulatory site controlling both the solubilization and disaggregation process of PrP peptide and perhaps the whole PrP protein.

Thus, according to one aspect of the present invention there is provided a method of treating a plaque forming disease. The method according to this aspect of the present invention is effected by displaying a polypeptide on a display vehicle, the polypeptide representing at least one epitope of an aggregating protein associated with plaque formation in the plaque forming disease, the at least one epitope being capable of eliciting antibodies capable of disaggregating the aggregating protein and/or of preventing aggregation of the aggregating protein, and introducing the display vehicle into a body of a recipient, so as to elicit the antibodies capable of disaggregating the aggregating protein and/or of preventing aggregation of the aggregating protein.

According to a preferred embodiment of the present invention the display vehicle is selected such that less than 30 days following an introduction of a triple dose of $10^{10}$ units thereof to the recipient, a titer of the antibodies in the recipient is above 1:50,000, as is determined by ELISA.

According to another aspect of the present invention there is provided an agent for treating a plaque forming disease. The agent according to this aspect of the present invention comprising a display vehicle displaying a polypeptide, the polypeptide representing at least one epitope of an aggregating protein associated with plaque formation in the plaque forming disease, the at least one epitope being capable of eliciting antibodies capable of disaggregating the aggregating protein and/or of preventing aggregation of the aggregating protein.

According to still another aspect of the present invention there is provided a pharmaceutical composition for treating a plaque forming disease. The composition according to this aspect of the present invention comprising an effective amount of a display vehicle displaying a polypeptide, the polypeptide representing at least one epitope of an aggregating protein associated with plaque formation in the plaque forming disease, the at least one epitope being capable of eliciting an effective amount of antibodies capable of disaggregating the aggregating protein and/or of preventing aggregation of the aggregating protein, and a pharmaceutically acceptable carrier.

According to yet another aspect of the present invention there is provided a method of preparing a display vehicle for treating a plaque forming disease. The method according to this aspect of the present invention is effected by genetically modifying a genome of a display vehicle by inserting therein a polynucleotide sequence encoding a polypeptide representing at least one epitope of an aggregating protein associated with plaque formation in the plaque forming disease, the at least one epitope being capable of eliciting antibodies capable of disaggregating the aggregating protein and/or of preventing aggregation of the aggregating protein, such that when the display vehicle propagates the polypeptide is displayed by the display vehicle.

Use of beta amyloid peptide antigens in conjunction with adjuvants to effect immunization has previously been difficult due to the resulting combination of high toxicity and low titers which result. Using prior art methods as a starting point, immunization of a mouse with a 16 amino acids peptide of beta-amyloid conjugated to KLH (SEQ ID NO:9) was carried out. This immunization produced a low but measurable antibody titer against beta-amyloid.

While reducing one aspect of the present invention to practice, splenectomy of the immunized mouse facilitated preparation of IgM hybridoma 508 expressing scFvAb with specificity to beta-amyloid. RNA was subsequently extracted from this hybridoma and was employed for antibody cloning. IgM 508 hybridoma showed specific activity to Aβ in preventing its toxic affect on PC12 cells (Anavi S., 1998). $V_H$ and $V_L$ sequences of IgM 508 were cloned separately and linked using a commercially available vector to form a single chain antibody with anti-beta amyloid specificity. This single chain antibody was subsequently expressed as a fusion protein in a phage display library and clones with anti beta amyloid activity were selected for propagation in E. coli.

Further reduction to practice was demonstrated by determining the apparent binding constants of the purified antibody presenting phage to amyloid beta were measured by ELISA test, and half-maximal binding was obtained at an antibody concentration of 340 ng/ml, corresponding to $8 \times 10^{-6}$ M. This result anticipates that the prepared single chain antibody will be effective under in vivo conditions. This phage was also able to disrupt already formed fibril structures confirming that the purified single chain antibody is biologically active, as suggested by the binding constant determination.

While reducing another aspect of the present invention to practice, it was uncovered that monoclonal antibodies raised against a peptide sequence of a prion protein were effective in disaggregating, or preventing the formation, of prion plaques.

A model for assessing PrP 106–126 toxicity was established by the present inventors and utilized to test the effectiveness of two immunoglobulin clones [designated mAb 3-11 (IgM) and mAb 2–40 (IgG1)] for neuroprotective and disaggregative capabilities.

As is further detailed in Examples 15–21, both mAb 3–11 and mAb 2–40 significantly reduced the dose dependent toxic effects of PrP 106–126 on PC-12 cells. Co-incubation of mAb 3–11 with PrP 106–126 prevented fibrillar aggregation, while administration of mAb 3–11 to already formed aggregates, resulted in disaggregation of 5% of the amyloid fibrils (Example 21).

Thus, according to an additional aspect of the present invention there is provided a method of treating a plaque forming disease. The method according to this aspect of the present invention is effected by displaying a polypeptide representing at least an immunological portion of an antibody being for binding at least one epitope of an aggregating protein associated with plaque formation in the plaque forming disease, the binding capable of disaggregating the aggregating protein and/or of preventing aggregation of the aggregating protein, and introducing the display vehicle into a body of a recipient so as to disaggregate the aggregating protein and/or prevent its aggregation.

According to a preferred embodiment of the present invention, and as is further described hereinbelow and exemplified hereinunder in the Examples section, introducing the display vehicle into the body of the recipient so as to disaggregate the aggregating protein and/or prevent the aggregation of the aggregating protein is effected through an olfactory system of the recipient.

According to yet an additional aspect of the present invention there is provided an agent for treating a plaque forming disease. The agent according to this aspect of the present invention comprising a display vehicle displaying a polypeptide representing at least an immunological portion of an antibody which can bind at least one epitope of an aggregating protein associated with plaque formation in the plaque forming disease, the immunological portion of the antibody being capable of disaggregating said aggregating protein and/or of preventing aggregation of the aggregating protein.

According to still an additional aspect of the present invention there is provided a pharmaceutical composition for treating a plaque forming disease. The composition according to this aspect of the present invention comprising an effective amount of a display vehicle displaying a polypeptide representing at least an immunological portion of an antibody which can bind at least one epitope of an aggregating protein associated with plaque formation in the plaque forming disease, the immunological portion of the antibody being capable of disaggregating the aggregating protein, and a pharmaceutically acceptable carrier.

According to a further aspect of the present invention there is provided a method of preparing a display vehicle for treating a plaque forming disease. The method according to this aspect of the present invention is effected by genetically modifying a genome of a display vehicle by inserting therein a polynucleotide sequence encoding at least an immunological portion of an antibody capable of binding at least one epitope of an aggregating protein associated with plaque formation in the plaque forming disease, the immunological portion of the antibody being capable of disaggregating the aggregating protein.

For purposes of this specification and the accompanying claims, the terms "patient", "subject" and "recipient" are used interchangeably. They include humans and other mammals that are the object of either prophylactic, experimental, or therapeutic treatment.

For purposes of this specification and the accompanying claims, the terms "beta amyloid peptide" is synonymous with "β-amyloid peptide", "βAP", "βA", and "Aβ". All of these terms refer to a plaque forming peptide derived from amyloid precursor protein.

As used herein, "PrP protein", "PrP", "prion" and "prion protein" refer to polypeptides that are capable, under appropriate conditions, of inducing the formation of aggregates responsible for plaque forming diseases. For example, normal cellular prion protein ($PrP^C$) is converted under such conditions into the corresponding scrapie isoform ($PrP^{Sc}$) which is responsible for plaque forming diseases such as, but not limited to, bovine spongiform encephalopathy (BSE), or mad cow disease, feline spongiform encephalopathy of cats, kuru, Creutzfeldt-Jakob Disease (CJD), Gerstmann-Straussler-Scheinker disease (GSS), and fatal familial insomnia (FFI).

As used herein in the specification and in the claims the term "disaggregating" refers to solubilization of aggregated proteins typically held together by non covalent bonds.

For purposes of this specification and the accompanying claims the terms "comprising" refers to inclusion of one or more recited element but does not exclude other elements not specifically recited. For example, a composition that comprises Aβ peptide encompasses both an isolated Aβ peptide and Aβ peptide as a component of a larger polypeptide sequence. Similarly, an immunological portion of an antibody may be included as a part of a larger of the antibody, say the entire antibody.

As used herein in the specification and in the claims section that follows, the term "treating" includes substantially inhibiting, slowing or reversing the progression of a disease, substantially ameliorating clinical symptoms of a disease or substantially preventing the appearance of clinical symptoms of a disease.

As used herein in the specification and in the claims section that follows, the term "plaque forming disease" refers to diseases characterized by formation of plaques by an aggregating protein (plaque forming peptide), such as, but not limited to, beta-amyloid, serum amyloid A, cystantin C, IgG kappa light chain or prion protein, in diseases such as, but not limited to, early onset Alzheimer's disease, late onset Alzheimer's disease, presymptomatic Alzheimer's disease, SAA amyloidosis, hereditary Icelandic syndrome, senility, multiple myeloma, and to prion diseases that are known to affect humans, such as for example, kuru, Creutzfeldt-Jakob disease (CJD), Gerstmann-Straussler-Scheinker disease (GSS), and fatal familial insomnia (FFI) and animals, such as, for example, scrapie and BSE.

Because amyloid plaques associated with the diseases described hereinabove are located within the brain, any proposed treatment modality must demonstrate an ability to cross the blood brain barrier (BBB) as well as an ability to dissolve amyloid plaques. Normally, the average size of molecules capable of penetrating the BBB is approximately 2 kDa. Monoclonal antibodies are typically in the range 135–900 kDa. Therefore, future therapeutic use of antibodies in treating amyloid plaque diseases must rely on either reduction of their size concurrent with retention of activity, or on development of novel delivery strategies.

Small synthetic peptides consisting of antigen epitopes, such as the EFRH (SEQ ID NO:1) epitope of Aβ or the PrP 106–126 peptide (SEQ ID NO:25) described herein, are in general poor antigens and need to be coupled to a larger carrier. Even after coupling they may induce only a low affinity immune response. For example, injection of Aβ-KLH or Aβ-fibril leads to very slow immune response (Anavi S., 1998) and many efforts have been made to circumvent low affinity response, with limited success.

Since the pathological effects of plaque forming polypeptides are maintained only in the central nervous system (CNS), the capability of highly specific Abs in preventing such plaques in vivo is dependent on the permeability of the blood brain barrier (BBB). For example, in the progressive stage of AD, evidence shows alteration in the permeability of the BBB, which may lead to direct delivery of such antibody from the periphery to the CNS to disaggregate already formed plaques and minimize further toxic effects (Schenk et al, 1999). Preferred embodiments of the present invention include direct delivery of monoclonal Abs presented on display vehicles to the brain across the blood brain barrier.

An increasing body of evidence shows that olfactory deficits and degenerative changes in the central olfactory pathways are affected early in the clinical course of AD. Moreover, the anatomic patterns involved in AD suggest that the olfactory pathway may be the initial stage in the development of AD.

olfactory receptor neurons are bipolar cells that reside in the epithelial lining of the nasal cavity. Their axons traverse the cribriform plate and project to the first synapse of the olfactory pathway in the olfactory pathway in the olfactory bulb of the brain. This configuration makes them a highway by which viruses or other transported substances may gain access to the CNS across the BBB.

In the early stages of AD, the BBB may limit the entry of antibody circulating in the periphery to the CNS. In contrast Aβ anti-aggregating antibodies displayed on a phage surface have the potential not only to be delivered directly to the CNS by intranasal administration but also to prevent olfactory permanent damage by Aβ in the patients. As previously shown, intranasal administration (Mathison et al, 1998; Chou et al, 1997; Draghia et al, 1995) enables the direct entry of viruses and macromolecules into the CSF or CNS.

Use of olfactory receptor neurons as a point of delivery for an adenovirus vector to the brain is reported in the literature. This method reportedly causes expression of a reporter gene in the brain for 12 days without apparent toxicity (Draghia et al, 1995).

Thus, according to a preferred embodiment of the present invention, a vehicle displaying an immunological portion of an antibody capable of disaggregating, or preventing the formation of, a polypeptide aggregate associated with a plaque forming disease is delivered via this route to the brain.

As Aβ is produced continuously by cells in peripheral tissues which cross the blood brain barrier (BBB) leading to localized toxic effects in specific neuronal populations, intranasal administration of such a vehicle may also prevent the progression of the disease by minimizing the amount of peripheral Aβ available to form plaques.

The use of display vehicles such as filamentous phages as a drug delivery system to the CNS opens new horizons for therapeutic approaches for Alzheimer's disease, as well as for other neurodegenerative diseases involving toxic extracellular aggregation of human peptides such as for example, prion generated diseases.

The display vehicle according to the present invention can be of any type including viral (e.g., bacteriophage, such as filamentous bacteriophage, fd, for example), bacterial and prion display vehicles. Thus, for example, the display vehicle can be a double stranded DNA virus, a single stranded DNA virus, an RNA virus (positive or negative strand), a bacteria and a polypeptide carrier. According to a preferred embodiment of the present invention the display vehicle is capable of propagation in the recipient. Thus, for example, a bacteriophage display vehicle can be propagated in bacterial flora, such as *Escherichia coli* residing in the recipient's body. Alternatively, the display vehicle is an in vivo non-propagateable particle.

The phage or virus vehicle has promise as a targetable in vivo therapy approach. Although concerns about the potential infection of the natural intestinal flora (Delmastro et al, 1997; Willis et al, 1993; Poul et al, 1999,) have been expressed, UV inactivation of phage showed (Delmastro et al, 1997) that they are as immunogenic as their infective counterparts. Use of inactivated phage may preclude incorporation of phage-encoded transgenes into the nucleus for subsequent expression in host cells (Larocca et al, 1998), an important practical consideration. Therefore, according to alternate preferred embodiments, the display vehicles employed in the present invention may be either replicating or non-replicating.

Phage or virus display involves the expression of cDNA clones as fusion proteins with phage or virus coat proteins. If the cDNAs selected for expression encode antigens, the phage or virus may then be employed as an antigen-presenting vehicle, which can optionally replicate within a recipient.

As described above, according to preferred embodiments of the present invention, antigens displayed by a phage or virus may be used directly for vaccination, without antigen purification. In this case, the bulk of the coat proteins serve to stimulate a general immune response because they are "non-self" with respect to the vaccinated subject. The antigen-coat protein fusion elicits a specific antibody against epitopes in the displayed cDNA gene product.

Antibody phage or virus display is accomplished, for example, by fusing the coding sequence of the antibody variable regions to a phage or virus coat protein. To this end, the variable (V) regions ($V_H$ and $V_L$) mRNA isolated from antibody-producing cells is reverse-transcribed into cDNA, and heavy and light chains assembled randomly to encode single chain Fv (scFv). These cassettes are cloned directly into a suitable vector such as a phagemid vector for expression and display on the phage or virus surface. This linkage between antibody genotype and phenotype allows the enrichment of antigen specific phage or virus antibodies, using immobilized or labeled antigen. Phage or virus that display a relevant antibody will be retained on a surface coated with antigen, while non-adherent phages or viruses will be washed away. Bound phages or viruses can be recovered from the surface, re-infected into suitable host cells and re-grown for further enrichment and, eventually for binding analysis.

The success of antibody phage or virus display hinges on the combination of this display and enrichment method. Phage or virus antibody genes can be sequenced, mutated and screened to improve antigen binding.

It is possible to rearrange the genes that code for the various regions of an antibody molecule such that its specificity and affinity for an antigen are altered. The antibody can be maintained on the surface of the phage or virus for further manipulation or be released as soluble scFv (~25 kDa) fragment.

Since its invention at the beginning of the 1990's, antibody phage display has revolutionized the generation of monoclonal antibodies and their engineering. This is because phage display allows antibodies to be made completely in vitro, bypassing the immune system and the immunization procedure, and allowing in vitro tailoring of the affinity and specificity of the antibody. It is therefore anticipated that the most efficient new vaccine development strategies will employ this technology.

Additional features can be added to the vector to ensure its safety and/or enhance its therapeutic efficacy. Such features include, for example, markers that can be used to negatively select against cells infected with the recombinant virus such as antibiotic sensitivity. Negative selection is therefore a means by which infection can be controlled because it provides inducible suicide through the addition of antibiotic. Such protection ensures that if, for example, mutations arise that produce altered forms of the viral vector or recombinant sequence, cellular transformation will not occur. Features that limit expression to particular cell types can also be included. Such features include, for example, promoter and regulatory elements that are specific for the desired cell type.

Viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell.

As used herein in the specification and in the claims section that follows, the term polypeptide refers to a stretch of amino acids covalently linked there amongst via peptide bonds. Different polypeptides have different functionalities according to the present invention. While according to one aspect a polypeptide is derived from an immunogen designed to induce an active immune response in a recipient, according to another aspect of the invention, a polypeptide is derived from an antibody which results following the elicitation of an active immune response, in, for example, an animal, and which can serve to induce a passive immune response in the recipient. In both cases, however, the polypeptide is encoded by a polynucleotide according to any possible codon usage.

As used herein the phrase "immune response" or its equivalent "immunological response" refers to the development of a beneficial humoral (antibody mediated) and/or a cellular (mediated by antigen-specific T cells or their secretion products) response directed against an aggregating protein (plaque forming peptide) in a recipient patient. Such a response can be an active response induced by administration of immunogen or a passive response induced by administration of antibody or primed T-cells. A cellular immune response is elicited by the presentation of polypeptide epitopes in association with Class I or Class II MHC molecules, to activate antigen-specific $CD4^+$ T helper cells and/or $CD8^+$ cytotoxic T cells. The response may also involve activation of monocytes, macrophages, NK, cells, basophils, dendritic cells, astrocytes, microglia cells, eosinophils or other components of innate immunity.

As used herein "active immunity" refers to any immunity conferred upon a subject by administration of an antigen.

As used herein "passive immunity" refers to any immunity conferred upon a subject without administration of an antigen. "Passive immunity" therefore includes, but is not limited to, administration of a replicating display vehicle that includes an immunological portion of an antibody presented on its surface to a recipient. Although replication of such a vehicle is active, the immune response is passive from the standpoint of the recipient.

For purposes of this specification and the accompanying claims the terms "epitope" and "antigenic determinant" are used interchangeably to refer to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8–10 amino acids in a unique spatial conformation. Methods of determining spatial conformation of epitopes include, for example, x-ray crystallography and 2-dimensional nuclear magnetic resonance. See, e.g., *Epitope Mapping Protocols in Methods in Molecular Biology*, Vol. 66, Glenn E. Morris, Ed. (1996). Antibodies that recognize the same epitope can be identified in a simple immunoassay showing the ability of one antibody to block the binding of another antibody to a target antigen. T-cells recognize continuous epitopes of about nine amino acids for CD8 cells or about 13–15 amino acids for CD4 cells. T cells that recognize the epitope can be identified by in vitro assays that measure antigen-dependent proliferation, as determined by $^3$H-thymidine incorporation by primed T cells in response to an epitope (Burke et al, 1994), by antigen-dependent killing (cytotoxic T lymphocyte assay, Tigges et al, 1996) or by cytokine secretion.

The presence of a cell-mediated immunological response can be determined by proliferation assays ($CD4^+$ T cells) or CTL (cytotoxic T lymphocyte) assays. The relative contributions of humoral and cellular responses to the protective or therapeutic effect of an immunogen can be distinguished by separately isolating IgG and T-cells from an immunized syngeneic animal and measuring protective or therapeutic effect in a second subject.

As used herein and in the claims, the terms "antibody" or "immunoglobulin" are used interchangeably and refer to any of several classes of structurally related proteins that function as part of the immune response of an animal or recipient, which proteins include IgG, IgD, IgE, IgA, IgM and related proteins.

Under normal physiological conditions antibodies are found in plasma and other body fluids and in the membrane of certain cells and are produced by lymphocytes of the type denoted B cells or their functional equivalent. Antibodies of the IgG class are made up of four polypeptide chains linked together by disulfide bonds. The four chains of intact IgG molecules are two identical heavy chains referred to as H-chains and two identical light chains referred to as L-chains.

In order to produce polyclonal antibodies, a host, such as a rabbit or goat, is immunized with the antigen or antigen fragment, generally with an adjuvant and, if necessary, coupled to a carrier. Antibodies to the antigen are subsequently collected from the sera of the host. The polyclonal antibody can be affinity purified against the antigen rendering it monospecific. Previous experience has shown that standard production of polyclonal antibodies is not the method of choice for preparation of disaggregating antibodies for plaque forming peptides due to problems of poor titer and toxicity.

In order to produce monoclonal antibodies hyperimmunization of an appropriate donor, generally a mouse, with the antigen is undertaken. Isolation of splenic antibody producing cells is then carried out. These cells are fused to a cell characterized by immortality, such as a myeloma cell, to provide a fused cell hybrid (hybridoma) which can be maintained in culture and which secretes the required monoclonal antibody. The cells are then be cultured, in bulk, and the monoclonal antibodies harvested from the culture media for use. By definition, monoclonal antibodies are specific to a single epitope. Monoclonal antibodies often have lower affinity constants than polyclonal antibodies raised against similar antigens for this reason.

Monoclonal antibodies may also be produced ex-vivo by use of primary cultures of splenic cells or cell lines derived from spleen (Anavi S., 1998. In order to produce recombinant antibody (see generally Huston et al, 1991; Johnson et al, 1991; Mernaugh et al, 1995), messenger RNAs from antibody producing B-lymphocytes of animals, or hybridoma are reverse-transcribed to obtain complementary DNAs (cDNAs). Antibody cDNA, which can be full length or partial length, is amplified and cloned into a phage or a plasmid. The cDNA can be a partial length of heavy and light chain cDNA, separated or connected by a linker. The antibody, or antibody fragment, is expressed using a suitable expression system to obtain recombinant antibody. Antibody cDNA can also be obtained by screening pertinent expression libraries.

The antibody can be bound to a solid support substrate or conjugated with a detectable moiety or be both bound and conjugated as is well known in the art. For a general discussion of conjugation of fluorescent or enzymatic moieties see Johnstone et al (1982). The binding of antibodies to a solid support substrate is also well known in the art. See for a general discussion Harlow et al (1988) and Borrebaeck (1992).

As used herein and in the claims, the phrase "an immunological portion of an antibody" include an F(ab')$_2$ fragment of an antibody, an Fab fragment of an antibody, an Fv fragment of an antibody, a heavy chain of an antibody, a light chain of an antibody, an unassociated mixture of a heavy chain and a light chain of an antibody, a heterodimer consisting of a heavy chain and a light chain of an antibody, a catalytic domain of a heavy chain of an antibody, a catalytic domain of a light chain of an antibody, a variable fragment of a light chain of an antibody, a variable fragment of a heavy chain of an antibody, and a single chain variant of an antibody, which is also known as scFv. In addition, the term includes chimeric immunoglobulins which are the expression products of fused genes derived from different species, one of the species can be a human, in which case a chimeric immunoglobulin is said to be humanized. Typically, an immunological portion of an antibody competes with the intact antibody from which it was derived for specific binding to an antigen.

Optionally, an antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

As used herein the terms "immunogenic agent" or "immunogen" or "antigen" are used interchangeably to describe a molecule capable of inducing an immunological response against itself on administration to a recipient, either alone, in conjunction with an adjuvant, or presented on a display vehicle.

As used herein the term "adjuvant" refers to a compound that, when administered in conjunction with an antigen, augments the immune response to the antigen, but when administered alone does not generate an immune response to the antigen. Adjuvants can augment an immune response by several mechanisms including lymphocyte recruitment, stimulation of B and/or T cells, and stimulation of macrophages.

A pharmaceutical preparation according to the present invention includes, as an active ingredient, a display vehicle displaying at least one epitope of an aggregating protein associated with plaque formation in a plaque forming disease, the at least one epitope being capable of eliciting antibodies capable of disaggregating the aggregating protein. Alternatively, a pharmaceutical composition according to the present invention includes, as an active ingredient, a display vehicle displaying at least an immunological portion of an antibody being for binding at least one epitope of an aggregating protein associated with plaque formation in said plaque forming disease, said immunological portion of said antibody being capable of disaggregating said aggregating protein.

The preparation according to the present invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the preparation accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in *Remington's Pharmaceutical Sciences*, Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular injections.

Alternately, one may administer a preparation in a local rather than systemic manner, for example, via injection of the preparation directly into the brain of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents that increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired circulating antibody concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl et al, 1975, in *The Pharmacological Basis of Therapeutics*, Ch. 1 p.1).

Dosage amount and interval may be adjusted individually to provide plasma or brain levels of antibodies that are sufficient to prevent aggregation or disaggregate existing aggregates (minimal effective concentration, MEC). The MEC will vary for each preparation, but can be estimated from in vitro data. Dosages necessary to achieve the MEC will depend on individual characteristics and route of administration. Binding assays can be used to determine plasma concentrations.

Dosage intervals can also be determined using the MEC value. Preparations should be administered using a regimen, which maintains plasma levels above the MEC for 10–90% of the time, preferable between 30–90% and most preferably 50–90%.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

The present invention also relates to a method of detecting both the pathogenic and non-pathogenic form of a prion protein in a biological sample.

Thus according to another aspect of the present invention there is provided a method of detecting a presence or an absence of a prion protein in a biological sample, the method comprising the steps of: (a) incubating an anti-prion antibody or an immunological portion thereof with the biological sample; and (b) determining a presence or an absence of antibody-antigen complexes, thereby determining the presence or the absence of the prion protein in the biological sample.

It will be appreciated that such complexes can be detected via any one of several methods known in the art, which methods can employ biochemical and/or optical detection schemes.

Thus, this aspect of the present invention provides a method of assaying or screening biological samples, such as body tissue or fluid suspected of including a prion protein either in a native non-disease conformation or a disease related conformation.

The detection method according to this aspect of the present invention can also be utilized for rapid and cost effective screening of products such as pharmaceuticals (derived from natural sources), foods, cosmetics or any materials that might contain prions.

It will be appreciated that such a detection method can also be utilized in an assay for uncovering potential anti-prion drugs useful in prevention or disaggregation of prion aggregates.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, *Molecular Cloning: A laboratory Manual* Sambrook et al, (1989); *Current Protocols in Molecular Biology* Volumes I–III, Ausubel, R. M. (ed.) (1994); Ausubel et al, *Current Protocols in Molecular Biology*, John Wiley and Sons, Baltimore, Md. (1989); Perbal, *A Practical Guide to Molecular Cloning*, John Wiley & Sons, New York (1988); Watson et al, *Recombinant DNA*, Scientific American Books, New York; Birren et al (eds) *Genome Analysis: A Laboratory Manual Series*, Vols. 1–4, Cold Spring Harbor Laboratory Press, New York (1998); methodologies as set forth in U.S. Pat. Nos. 4,666,828; 4,683,202; 4,801,531; 5,192,659 and 5,272,057; *Cell Biology: A Laboratory Handbook*, Volumes I–III, Cellis, J. E. (ed.) (1994); *Current Protocols in Immunology* Volumes I–III, Coligan J. E. (ed.) (1994); Stites et al, (eds), *Basic and Clinical Immunology* (8th Edition), Appleton & Lange, Norwalk, Conn. (1994); Mishell and Shiigi (eds), *Selected Methods in Cellular Immunology*, W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; *Oligonucleotide Synthesis* Gait, M. J. (ed.) (1984); *Nucleic Acid Hybridization* Hames, B. D., and Higgins S. J. (eds.) (1985); "*Transcription and Translation*" Hames, B. D., and Higgins S. J. (eds.) (1984); "Animal Cell Culture" Freshney, R. I. (ed.) (1986); *Immobilized Cells and Enzymes* IRL Press (1986); *A Practical Guide to Molecular Cloning* Perbal supra, and *Methods in Enzymology* pp. 1–317, Academic Press; "*PCR Protocols: A Guide To Methods And Applications*", Academic Press, San Diego, Calif. (1990); Marshak et al, *Strategies for Protein Purification and Characterization—A Laboratory Course Manual* CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Reference is made to the following materials and methods, which were employed in experiments described in the following examples.

Materials and Experimental Methods

The following materials and experimental methods were employed while reducing the present invention to practice as is further demonstrated in the Examples that follow:

General Recombinant DNA and Phage Techniques

Standard recombinant DNA techniques were performed essentially as described (Sambrook et al, 1989). General protocols for antibody-phage display technology are from the Pharmacia Biotech (Uppsala, Sweden) Recombinant Phage Antibody System (RPAS).

Construction of 508 scFv on the Phage Display

The 508 IgM hybridoma used as the source for antibody variable-region sequences was generated from splenocytes of a mouse that had been immunized with a peptide corresponding to the 16 amino terminal residues of βAP conjugated to keyhole limpet hemocyanin, used as a carrier. mRNA extraction, first strand cDNA synthesis, PCR amplification of variable heavy ($V_H$) and variable light ($V_L$) sequences, and assembly of scFv cassettes, were done according to protocols essentially as described (Pharmacia Biotech RPAS manual). Assembled 508 scFv DNA was digested with SfiI and NotI, and 100 ng were ligated with 150 ng of vector DNA prepared by digestion of phagemid pCC-Gal6(Fv) (Berdichevsky et al, J1999) with SfiI and NotI. This phage-display system is designed to express the scFv in frame fusion protein with cellulose binding domain (CBD) derived from *Clostridium thermocellum* (Morag et al, 1995). Ligated DNA was introduced into XL-1 Blue cells (Stratagene, La Jolla, Calif.) by transformation and transformants were plated onto 2×YT Agar plates containing 100 μg/ml ampicillin and 1% glucose for overnight growth at 37° C.

Selection of β-amyloid Binding scFv-CBD Fusion Proteins

Individual clones were picked and grown, each in 5 ml 2×YT, 1% glucose, 100 μg/ml Ampicillin overnight at 30° C.

IPTG was added at 1 mM for a 3-hour induction period. Soluble scFv-CBD fusion proteins were isolated from each clone by sonication of induced cell pellets. In order to identify functional soluble 508(Fv) from non-functional ones, 250 ng/well β-amyloid peptide were covalently bound to epoxy-coated microtiter plates for 16 hours at 4° C. (Solomon et al, 1996). The plates were washed with PBS/ 0.05%—Tween 20 (PBST), and blocked with a mixture of 3% bovine serum albumin and milk powder in PBS for 16 hours at 4° C. The plates were then washed and incubated with the soluble scFv-CBD recovered from the clones for 1 hour at 37° C. The bound antibody was detected with a rabbit anti CBD antiserum followed by HRP-conjugated goat anti rabbit antibodies. Plates were developed with the peroxidase chromogenic substrate ABTS and the signal was recorded with an ELISA microtiter plate reader at 405 nm. Positive phage clones (pCC-508(Fv)) were propagated and their DNA was sequenced using an automated model 373A DNA sequencer (Applied Biosystems, USA).

Production of 508(Fv)-CBD Fusion Proteins in *E. coli*

For high-level expression in *E. coli*, wild type (wt) and mutated 508(Fv) derivatives were cloned into the pFEKCA3 vector as described (Berdichevsky et al, 1999). This vector utilizes the strong T7 promoter for expression, where the T7 RNA polymerase gene is carried as a lac repressor controlled-IPTG inducible gene in *E. coli* BL21 (DE3) (Studier et al, 1990). Upon IPTG induction, 508(Fv)-CBD proteins accumulated as insoluble inclusion bodies. They were recovered by the cellulose-assisted refolding method as previously described (Berdichevsky et al, 1999). SDS polyacrylamide gel electrophoresis (SDS/PAGE) was used to separate proteins according to their molecular weight under denaturing conditions (Laemmli 1970).

Stability Assay of the Purified 508(Fv)-CBD Protein

The activity of purified 508(Fv)-CBD protein was checked before and after storage at 4° C. for 7 days. 250 ng/well β-amyloid peptide was covalently bound to epoxycoated wells of microtiter plates for 16 hours at 4° C. (Solomon et al, 1997). Wells were blocked with a mixture of 3% bovine serum albumin and bovine hemoglobin in PBS for 2 hours at 37° C., then washed and incubated with the 508(Fv)-CBD protein (0.5 μg/ml or as otherwise specified) for 1 hour at 37° C. Bound antibody fragments were detected by incubation with HRP-conjugated rabbit anti-mouse antibodies (BioMakor, Rehovot, Israel), diluted 1:5,000 and rabbit anti CBD diluted 1:10,000 in PBST for 1 hour at 37° C. The bound antibody fragments were monitored as described above.

Construction of a Phage Library for the Isolation the 508 (Fv) βAP Binding Mutants Splicing overlap extension (SOE) PCR technique (Lefenbrve et al, 1995) was used to replace $V_L$ cysteine codon 96 of 508(Fv) with other codons. pCC-508(Fv) DNA was used as template. In a first step, the template DNA was amplified with the following primers:

The antisense primer 508-mut-FOR: 5'-CCCCCCTCCGAAC GTSNATGGGTAACTcgatcgCTGATGGCAGTA-3' (SEQ ID NO:10) inserts a PvuI restriction site (underlined), where S represents nucleotides C or G and N represents A, C, T or G. This primer was used for the replacement of cysteine codon 96 with phenylalanine (F), leucine (L), serine (S), tyrosine (Y) or tryptophan codons. The primer SfiI 5'BACK: 5'-ATCTATGCggcccagccggccATG-3' (SEQ ID NO:11) inserts an SfiI site at the 5' end of the scFv. The resulting PCR product (SfiI-508mut) corresponds to the 5' half of 508(Fv)-CBD. In the second PCR step, the complete 508 (Fv)-CBD was re-assembled by amplifying pCC-58(Fv) DNA with the SfiI-508mut PCR product from step 1 serving as the 5' end primer and CBD(BX): 5'GTGGTGCTGAGTg-gatccta TACTACACTGCCACCGGG-3' (SEQ ID NO:12) as the 3' end primer. The final PCR product (SfiI-508mut-BX) is a complete 508(Fv)-CBD cassette with replacements at $V_L$ codon 96 and an engineered PvuI restriction site as a silent mutation for analysis. SfiI-508mut-BX DNA was digested with SfiI, PvuI and NotI and ligated in a three fragment ligation with SfiI and NotI linearized pCC-Gal6 (Fv) DNA which is a phagemid vector used to display an anti *E. coli* β-galactosidase scFv (Berdichevsky et al, 1999). The resulting ligated phagemid DNA was introduced into *E. coli* XL-1-Blue cells by electroporation. Cultures of *E. coli* were used to produce displaying phage by rescue with M13KO7 helper phage (Pharmacia Biotech, Uppsala, Sweden).

Affinity Selection of β-amyloid Binding 508mut-(Fv) Displaying Phage Clones

A sample containing rescued phage particles was subjected to one round of affinity selection (biopanning) and amplification. For the selection cycle, 0.5 μg/ml biotinylated β-amyloid 1–16 amino acid peptide (βAP(1–16), acids 1–16 OF SEQ ID NO:3) in a total volume of 1 ml were used. The phages were pre-incubated with the biotinylated peptide for 2 hours at room temperature, and the reaction mixture was then layered on streptavidin-coated 30 mm polystyrene Petri dishes and incubated for 20 minutes at room temperature. Unbound phages were removed by extensive washing with PBST. The bound phages were eluted with 0.3 ml of 0.1 M HCl titrated to pH 2.2 with glycine. The eluate was neutralized with 80 μl of 0.5 M Tris (HCl) pH 10, and used to infect *E. coli* XL-1-Blue cells. Individual bacterial colonies containing amplified phage particles were used as a template for colony PCR (Novagen Madison, USA) with primers SfiI5'Back and CBD(BX). The PCR product of about the size of an intact scFv-CBD fragment (about 1250 bp) was digested with the restriction enzyme PvuI and analyzed by agarose gel electrophoresis.

ScFv Binding to Biotinylated βAP(1–16)

Binding of scFv to βAP(1–16) was analyzed by ELISA. Coated plates with 50 μl of 1 μg/ml streptavidin in 0.1 M NaHCO$_3$, pH 9.6, were washed three times with PBST and 50 μl of 6 ng/μl biotinylated βAP(1–16) were then added to the wells and incubated for 30 minutes at 37° C. Wells were blocked with a mixture of 3% bovine serum albumin and bovine hemoglobin in PBS for 2 hours at 37° C., then washed and incubated with the scFv (0.5 μg/ml or as otherwise specified) for 1 hour at 37° C. For inhibition experiments, peptides were pre-incubated with the antibody for 30 minutes at 37° C. before their addition to peptide coated wells. After washing, bound antibody fragments were detected as described above. βAP specific binding phage clones were propagated and their DNA was isolated and sequenced as described above.

Cell Culture and βAP Cytotoxicity Assay

Rat phenochromocytoma PC12 cells were cultured in DMEM supplemented with 5% horse serum, 10% fetal calf serum, 2 mM L-glutamine, and 100 units/ml penicillin/ streptomycin and incubated at 37° C. under 5% CO$_2$. For the neurotoxicity assay, cultured PC12 cells were seeded into a 96-well plate at a density of $10^4$ cells/100 μl/well in a serum-free medium supplemented with 2 M of insulin. The effect on the prevention of the neurotoxicity of βA was measured as follows: 0.12 mM P-amyloid that was incubated for a week at 37° C. for the generation of fibrils, and further incubated in the presence of 508F(Fv)-CBD or with the unrelated Gal6(Fv)-CBD at a molar ratio of βAP to scFv of 15:1 or 30:1 for 24 hours. The βA/antibody mixture was added to the wells containing PC12 cells. The plates were incubated at 37° C. for 2 days, after which cell viability was assessed by measuring cellular redox activity with 3-(4,5-dimethylthiazol-2-yl)-2,5-diphenyl tetrazolium bromide (MTT), as described (Sladowski et al, 1993). The plates were incubated overnight at 37° C. MTT reduction was determined colorimetrically using an ELISA microtiter plate reader set at 550 nm.

Aggregation of β-Amyloid Peptide Measured by Thioflavin T (ThT) Fluorimetry

Aggregation of β-amyloid peptide was measured by the Thioflavin T (ThT) binding assay, in which the fluorescence intensity reflects the degree of β-amyloid fibril formation. ThT characteristically stains amyloid-like deposits (Levine H III, 1993) and exhibits enhanced fluorescence emission at 485 nm upon excitation at 435 nm when added to the suspension of aggregated β-sheet preparations. Aqueous solutions of 0.12 mM RAP in 0.1 M Tris (HCl) pH 7.1 were incubated at 37° C. for 1 week and further incubated in the presence of 508F(Fv)-CBD or with the unrelated Gal6(Fv)-CBD at a molar ratio of βAP to scFv of 15:1 or 30:1 for 24 hours. The fluorescence was measured after addition of 1 ml of ThT (2 μM in 50 mM Glycine, pH 9) with an LSB-50 Perkin Elmer Ltd., UK, spectrofluorometer.

Preparations of Phage Delivery System

12 Balb/c-female mice were divided to four groups of 3 mice per group. One group was used as control. Following a single dose of $10^{11}$ phage particles (fd phage, taken from a 15-mer phage peptide library which was provided by George P. Smith, University of Missouri, Columbia, Mo.) administered intranasally, mice were sacrificed in intervals of 1, 14 and 28 days in each group and their brains were taken for further analysis.

Ability of Phage Carrying scFv to Enter/Remove RAP Fragment from the Brain

ScFv-508F fusion to filamentous minor coat gpIII were used in order to investigate the ability of βAP anti-aggregating scFv to be carried by a filamentous phage display system directly into the CNS.

This scFv was prepared from anti-aggregation hybridoma 508 as described above and preserved its specific binding activity. Nine Balb/c mice divided into three groups were treated as follows. Mice of a first group were treated with 0.2 ml of $10^{-3}$ M biotin βA(1–16) alone. Mice of a second group were treated with a mix of $10_{10}$ phage carrying 508F-scFv that were pre incubated with 0.2 ml of $10^{-3}$ M biotin βA(1–16) for 1 hour. Mice of a third group were used as control. Following a single dose applied intranasally, mice were sacrificed in each group in intervals of 1, 14 and 28 days and their brains were taken for further analysis.

Preparations of Tissue Sections

Immediately following decapitation, brains were removed and cut into two halves along the mid-sagittal sinus. Randomly, one half-brain was fixed by immersion in 4% paraformaldehyde solution in 0.1 M phosphate buffer for two hours in 4° C. and then immersed for cold protection in 4.5% sucrose in 0.1 M PBS over night. The sections were then moved to 30% sucrose for 2 hours in 4° C. Sections of coronal blocks containing the olfactory and hippocampus were put in OCT and cut with thicknesses of 6 μm with a cryostat at −20° C., and then taken up on glass slides. Slides were kept at −70° C. These slides were used for phage detection using an immunofluorescence technique.

The other mid-sagittal half-brain was used for preparing paraffin tissue section for histology. The section were fixed in 4% paraformaldehyde for 2 hours, then transferred to 10% formalin saline for 2 days in room temperature, followed by embedding in paraffin, and cut with thicknesses of 4 μm on a microtome and then taken up on glass slides. The slides were kept at room temperature until used.

Detection of Antigen in Brain Sections

Immunofluorescence: Sections were blocked with 3% bovine serum albumin in PBS for 30 minutes and then incubated with rabbit polyclonal serum anti fd (1:100) or Streptavidin coupled with PE (sigma) for 1 hour at 37° C. Slides were then washed three times, 5 minutes each, in PBS, treated again with the blocking buffer for 5 minutes at room temperature, and then reacted with secondary r Cy™ 3 donkey anti-rabbit IgG (for phage detection) at 1:400 (sigma) or with streptavidin coupled to PE, 1:50 dilution, for 1 hour at room temperature. Finally, the preparations were washed three times in PBS, observed using a fluorescence microscope at a final magnification of ×10, and recorded on film or using a Hamamatsu digital camera (C4742) and Metamorph (Universal Imaging; West Chester, Pa.) computer software.

Histology: Six-micrometer sections were stained with hematoxylin and eosin. The stained sections were examined and photographed at a final magnification of ×40. Finally, the preparations were washed three times in PBS, observed on a microscope, and recorded on film.

Immunization with f3-YYEFRH

Immunizations were performed with a genetically engineered fd phage carrying the peptide YYEFRH (SEQ ID NO:7) fused to its minor coat gpIII. Doses of $10^{10}$ phages per injection were used to immunize at 14-day intervals, through intraperitoneal injections. Mice were injected with the phages with or without Freund's complete adjuvant (Difco) for the first injection and Freund's incomplete adjuvant (Difco) for the second injection. Following 7 days of each injections, the mice were bled and their serum were tested by ELISA for antibody IgG reactivity for both phage coat proteins and for βA.

Epitope Libraries

The 15-mer phage-peptide library used in this study was provided by George P. Smith (University of Missouri, Columbia, Mo.). The library consists of about $1.9 \times 10^9$ phage particles and comprises a random peptide repertoire of 15 amino acid residues fused to coat glycoprotein VIII of the fd phage. Experiments with this library were carried out according to instructions of the provider (George P. Smith University of Missouri, Columbia, Mo.).

Biotinylation of Antibodies

For antibody biotinylation, 100 μg of each antibody in 0.1 M NaHCO$_3$, pH 8.6, was incubated for 2 hours at room temperature with 5 μg of biotinamidocoproate N-hydroxysuccinimide ester (Sigma, B 2643) from a stock solution of 1 mg/ml in dimethylformamide and dialyzed at 4° C. against phosphate-buffered saline (PBS; 0.14M NaCl/ 0.01 M phosphate buffer, pH 7.4) overnight.

Isolation of Phage Presenting Epitopes from Peptide Library

A library sample containing 109 infectious phage particles was subjected to three rounds of selection (biopanning) and amplification. For each selection cycle a biotinylated monoclonal antibody (1 μg/μl) in a total volume of 25 μl was used. The phage clones were pre incubated with the biotinylated antibody overnight at 4° C., and the reaction mixtures were then layered in 1 ml of PBS containing 0.5% Tween 20 on streptavidin-coated 30 mm polystyrene Petri dishes and incubated for 20 minutes at room temperature. Unbound phages were removed by extensive washing (10 times for 10 minutes each) in PBS/0.05% Tween 20. The bound phages were eluted with 0.3 ml of 0.1 M HCl titrated to pH 2.2 with glycine. The eluate was neutralized and used to infect *E. coli* K91 cells. After three rounds of panning individual bacterial colonies containing amplified particles were grown on a microtiter plate and the selected phages were tested by ELISA for their ability to bind to the studied antibody, as described below.

Antibody Binding To Isolated Phage

Binding of antibodies to phage was analyzed by ELISA. Wells of microtiter plates (Maxisorb, Nunc) were coated with 50 μMl (at dilution of 1:1000 in 0.1 M NaHCO$_3$, pH 8.6) of rabbit anti-phage serum and incubated overnight at 40 C. The wells were blocked with a mixture of 3% bovine serum albumin and hemoglobin at a ratio of 1:1 (in PBS) for 2 hours at 37° C. Coated plates were washed three times with PBS/0.05% Tween 20, and 50 μl of enriched phage clones containing 10$^{10}$ phage particles were added to the wells and incubated for 1 hour at 37° C. After washing, the studied antibody was added (1 Mg/ml or as otherwise specified) and allowed to bind to the coated plate overnight at 4° C. and the binding constant thereof was measured. Positive phage clones were propagated and their DNA were sequenced in the insert region at the Sequencing Unit of the Weizmann Institute of Science (Rehovot, Israel) by using Applied Biosystem Kit (United States, Applied Biosystem).

fd gpVIII Phage Display of βA(1–16)

Coat glycoprotein VIII of filamentous phage is presented in approximately 2700 copies on the phage coat. The following oligonucleotides were prepared: sense—5'-agctccGATGCTGAATTCGGTGATAGCGGCTACGAA GTGCATCATCAGAAAcctgcag-3' (SEQ ID NO:13); and antisense—5'-ggTTTCTGATGATGCACTTCGTAGC CGCTATCATGACGAAATTCAGCATCgg-3' (SEQ ID NO:14). These oligonucleotides were used to form a duplex (68–70° C., 10 minutes, followed by slow cool to room temperature) that encodes for amino acids 1–16 of human βAP and contain a silent mutation of a specific restriction site (EcoRI), which is useful for further analysis. The duplex was phosphorylated and ligated into HindIII/PstI linearized f88–4 phagemid, which is a vector used to display fusion peptides on gpVIII of filamentous phage. The resulting ligated phagemid DNA was introduce into *E. coli* K91K cells by transformation and transformants were plated onto 2×YT Agar plates containing 10 μg/ml tetracycline and 1% glucose for overnight growth at 37° C. Individual bacterial colonies containing phage particles were used to inoculate 2×YT medium containing 10 μg/ml tetracycline for overnight growth at 37° C. for amplification. The DNA phagemid product obtained from each colony was analyzed by EcoRI. Positive clones were further amplified for antigen preparation.

Immunization with f88-EFRH

Immunizations were performed with a genetically engineered fd phage carrying the peptide VHEPHEFRHVAL-NPV (SEQ ID NO:8) fused to its major coat glycoprotein VIII. Doses of 10$^{10}$ phages per injection were used to immunize at 14-day intervals, through intraperitoneal injections. Mice were injected the phages with or without Freund's complete adjuvant (Difco) for the first injection and Freund's incomplete adjuvant (Difco) for the second injection. Following 7 days of each injections, the mice were bled and their serum were tested by ELISA for antibody IgG reactivity for both phage coat proteins and for βA.

Inhibition of Antibody Binding to β-Amyloid Peptide

The inhibition of antibody binding to βAP(1–16) by various small peptides was performed using 250 ng/well biotinylated β-amyloid peptides (1–16) bound covalently to ELISA plates as previously described. The plates were washed with PBS/0.05% Tween 20 and blocked with a mixture of 3% bovine serum albumin and hemoglobin, ratio 1:1 (in PBS) for 2 hours at 37° C. The peptides were pre incubated with 1:3000 dilution of serum after third immunization with f88-EFRH for 30 minutes at 37° C. before their addition to βAP-coated wells and were left overnight at 4° C. therein. After washing, bound antibody was detected by incubation with HRP-conjugated rabbit anti-mouse immunoglobulin, as described above. The results were used to derive the IC$_{50}$, which is the half molar concentration of peptide that fully inhibits antibody binding. Peptides were synthesized by Applied Biosystems Synergy Model 430A in the Unit for Chemical Services of the Weizmann Institute of Science by solid-phase using Fmoc chemistry.

Cell Culture and Cytotoxicity Assay

Rat phenochromocytoma PC12 cells were cultured in DMEM supplemented with 5% horse serum, 10% fetal calf serum, 2 mM L-glutamine, and 100 units/ml penicillin/streptomycin and incubated at 37° C. under 5% CO$_2$. For the neurotoxicity assay, cultured PC12 cells were seeded into a 96-well plate at a density of 10$^4$ cells/100 μl/well in a serum-free medium supplemented with 2 M of insulin. The effect on the prevention of the neurotoxicity of βA was measured as follows: 0.12 mM β-amyloid that was incubated for a week at 37° C. for the generation of fibrils, and further incubated in the presence of serum of EFRH-phage immunized mice and serum of a non-relevant phage immunized mice at dilutions of 5:1 and 10:1 for 24 hours. The βA antibody mixture was added to the wells containing PC12 cells. The plates were incubated at 37° C. for 2 days, after which cell viability was assessed by measuring cellular redox activity with 3-(4,5-dimethylthiazol-2-yl)-2,5-diphenyl tetrazolium bromide (MTT), as described (Sladowski et al, 1993). The plates were incubated overnight at 37° C. MTT reduction was determined colorimetrically using an ELISA microtiter plate reader set at 550 nm.

Preparation of Monoclonal Antibodies Against PrP 106–126

Mice immunized with synthetic peptide corresponding to the sequence of human PrP 106–126 (SEQ ID NO:25) (obtained from Chiron Technologies, Claton Victoria, Australia) coupled to the larger carrier KLH were used for generating monoclonal antibodies following the fusion techniques of Kohler and Milstein (Kohler et al, 1975).

Hybridomas were tested for the production of peptide-specific antibodies by ELISA, as follows: Peptide PrP 106–126 was covalently attached to the epoxy groups of Eupergit-C coated 96 well plates (Solomon et al, 1992, 1993). The residual epoxy groups were blocked by incubating the plates with 3% skim milk (blocking solution). Undiluted hybridoma supernatants were applied for 1 hour at 37° C. Wells were excessively rinsed (as in each step of the procedure) and further incubated with horseradish peroxidase (HRP) labeled goat-anti-mouse antibodies specific for mouse IgG or IgM (diluted in blocking solution). After washing, antibody binding was visualized using ortho-phenyldiamine as substrate for HRP. Optical density was measured at 492 nm. Selected monoclonal antibodies were scaled-up and purified according to published procedures: IgG molecules on a protein A column (Harlow et al, 1988) and IgM on KaptiveM column. Two mAbs, namely 2–40 and 3–11, were used for further studies. The mAb 3F4 was purchased from Senetek, Ca. USA.

Search for Antibody's Epitope Location Using Phage Display Library

The antibodies 3–11 (IgM) and 2–40 (IgG) were biotinylated. The following libraries (provided by G. P. Smith) were searched to find the epitope of the antibodies studied, as previously described (Frenkel et al, 1998).

1. fUSE5/15-mer library where foreign 15-mer are displayed on all 5 copies of pIII.
2. f88–4/6-mer library where foreign 6-mer are displayed on up to ~300 copies of pVIII (recombinant gene VIII encoding the peptide is inducible with IPTG).

The biopanning of the phages to find the antibodies' epitope was performed as previously described (Frenkel et al, 1998).

Competitive Inhibition of Antibodies Bound to PrP by Peptide NMKH

The ELISA competitive binding of the above antibodies to covalently bound PrP peptide was performed as described above. The antibodies were preincubated with peptide NMKH at equimolar ratio before adding to the wells.

PrP 106–126 Aggregation and Immunocomplexation

In vitro aggregation of peptide 106–126 was induced by incubation of an aqueous solution of PrP 106–126 (10 mg/ml) for various time intervals at 37° C. The aggregated peptide was incubated either with monoclonal antibodies 2–40, 3–11 or 3F4 at conditions specified later.

Cytotoxicity Assay of PrP 106–126 using PC12 Cells

Rat pheochromocytoma PC12 cells were cultured in DMEM supplemented with 8% horse serum, 8% fetal calf serum, 2 mM L-glutamine and 100 units/ml penicillin/streptomycin and incubated at 37° C. under 5% $CO_2$.

For the neurotoxicity assay, cultured PC12 cells were seeded on 96-well plates at a density of $2 \times 10^4$ cells/100 µl/well in a serum-free medium supplemented with 2 µM of insulin. Cells were treated for 3–5 days with 100 µM PrP 106-126 preincubated 4–7 days at 37° C. The cell viability was assessed by the MTT assay that measures the activity of mitochondrial enzymes responsible for the conversion of the tetrazolium salt, 3-(4,5-dimethylthiazol-2-yl)-2,5-diphenyl-tetrazolium bromide (MTT) to a formazan product in viable cells (Hansen et al, 1989). MTT was added to the wells to a final concentration of 1 mg/ml and incubated with the cells for an additional 3 hours at 37° C. Cell lysis buffer (20% wt/vol SDS in a solution of 50% dimethylformamide, pH 4.7) was added, and the plate was incubated overnight at 37° C. MTT reduction was determined colorimetrically by measuring the optical density (OD) at 550 nm.

Prevention of PrP 106–126 Neurotoxicity

The effect of mAbs on the inhibition of PrP 106–126 neurotoxicity was determined as follows: PrP 106–126 (10 mg/ml) was incubated for 7 days at 37° C. to induce maximal aggregation of the peptide. Monoclonal antibodies 3–11, 2–40 and 3F4 were added for 1 hour to samples of 1 mM of the already aggregated peptide. The antibody-peptide mixtures, as well as the aggregated peptide alone, were applied to the cells to a peptide final concentration of 100 µM. Cell viability following a 3 day incubation at 37° C. with the aforementioned reaction mixture, was assessed as described above. 100% viability was defined as the value of MTT assay for untreated cells.

Modulation of PrP Conformation Followed by Thioflavin T (ThT) Fluorimetry Assay

Increasing amounts of PrP 106–126 peptide (0–0.8 mg/ml) were incubated for 7 days at 37° C. Prion amyloid fibril formation was measured by the Thioflavin T (ThT) binding assay. The binding of ThT to amyloid fibrils of certain origins generates a specific fluorescent signal: a 114 nm red shift in the excitation peak from 336 nm of excitation spectrum of the free dye in solution to a new excitation peak at 450 nm of the bound dye. Additionally the bound dye has an enhanced emission at 482 nm (Naiki et al, 1989, Levine, 1993). The aggregation of the prion peptide was followed using samples of PrP 106–126 (0.3 mg/ml) in 0.1 M Tris/HCl pH-7.1 incubated for 7 days at 37° C., either with or without mAbs 3–11, 2–40 and 3F4 at various dilutions. Disaggregation of already formed prion amyloid fibrils was measured using samples of PrP 106–126 that were incubated for 7 days at 37° C. and then supplemented with the mAbs for an additional 24 hours. Fluorescence (emission at 482 nm after excitation at 435 nm) was measured after an addition of the samples to ThT (2 µM in 50 mM glycine, pH-9).

EXPERIMENTAL RESULTS

Examples 1–6 below relate to the production of a single chain version of the anti aggregating monoclonal antibody. Examples 7–8 below relate to delivery of peptide or antibody displaying phage to the brain. Examples 9–14 below relate to the production of high titers of anti-aggregating polyclonal antibodies by direct immunization with beta amyloid antigens displayed on a phage, and to characterization of these antibodies.

Example 1

Generation of an IgM Hybridoma 508

Immunization of a mouse with a 16 amino acid peptide of beta-amyloid (acids 1–16 of SEQ ID NO:3) conjugated to KLH (SEQ ID NO:9) was carried out as described hereinabove. Repetitious immunization eventually produced a low but measurable antibody titer against beta-amyloid. Subsequent splenectomy of the immunized mouse facilitated preparation of IgM hybridoma 508 expressing scFvAb with specificity to beta-amyloid. RNA was subsequently extracted from this hybridoma. The IgM 508 hybridoma showed specific activity to Aβ in preventing its toxic affects on PC12 cells (Anavi S. 1998).

Example 2

Cloning of the Variable Domains of the 508 IgM Hybridoma as a scFv

Figure 2:
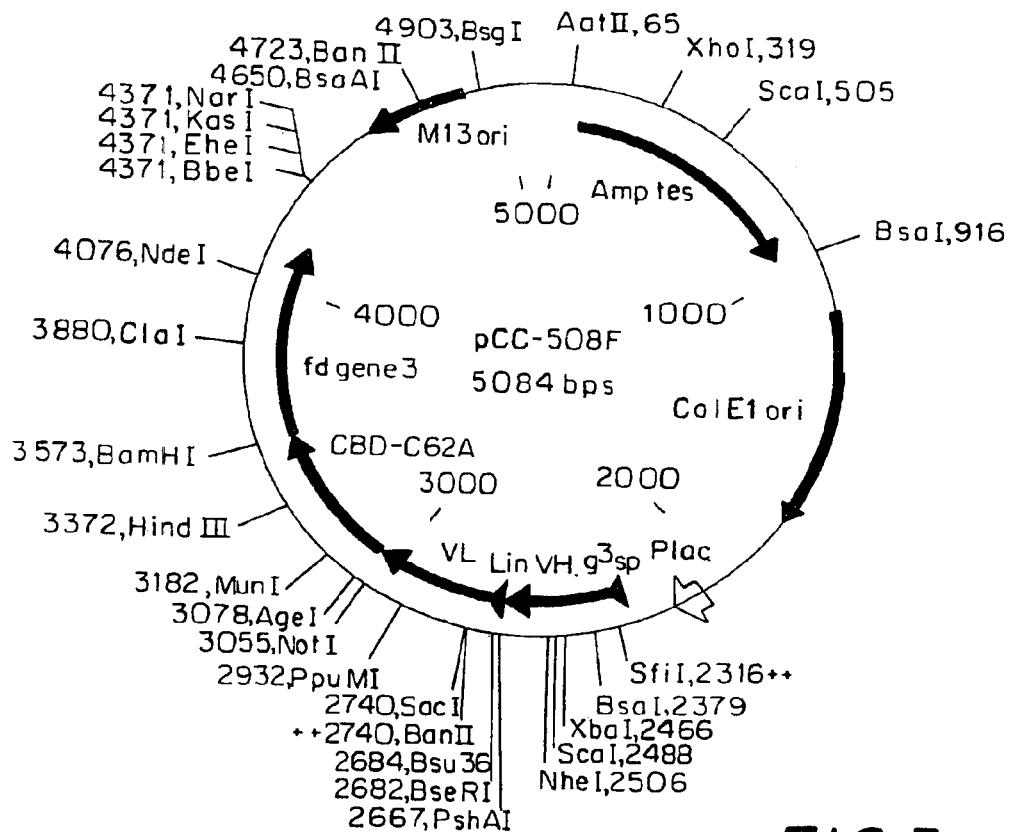
FIG. 2 is a physical map of plasmid pCC-508F that is used for the production of scFv-508-CBD fusion protein (also referred to herein as 508(Fv)-CBD) under control of lac promoter. Amp res—a gene encoding β-lactamase; $V_H$ and $V_L$-sequences coding for the variable domains of the heavy and light chains of scFv-508, respectively; Lin—a gene coding for a $(Gly_4Ser)_3$ (SEQ ID NO:2) linker present between the variable domains $V_H$ and $V_L$. Restriction sites and positions thereof are also shown.
Figure 3:
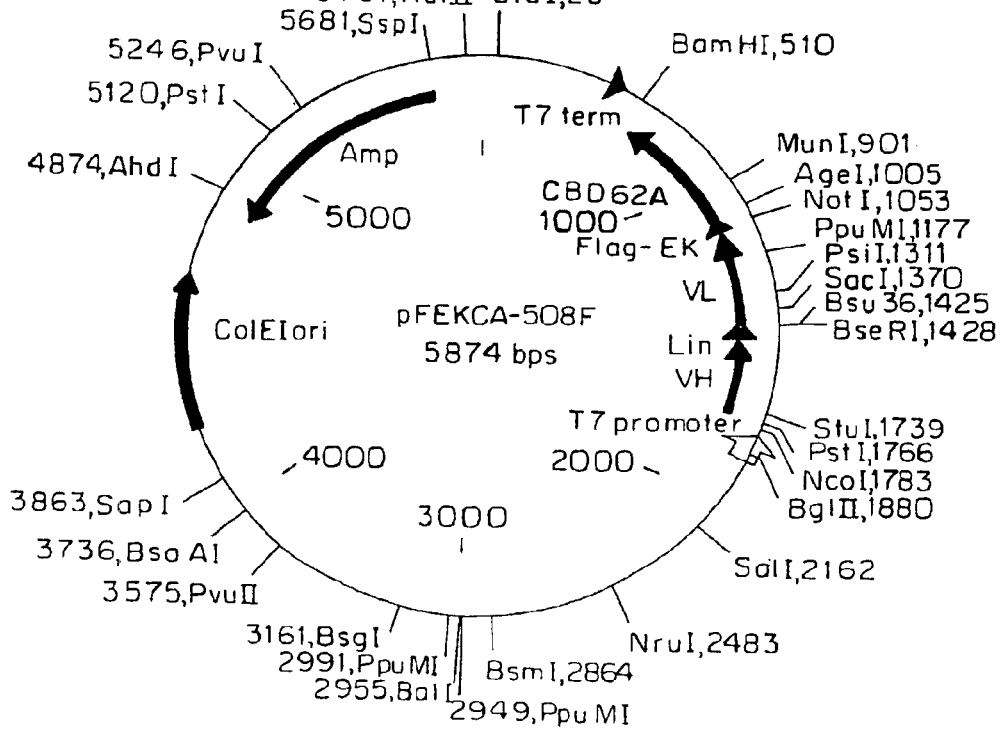
FIG. 3 is a physical map of plasmid pfFEKCA-508 that is used according to the present invention for cytoplasmic expression of the scFv-508-CBD fusion protein under the control of a T7-promoter. Amp res—a gene encoding β-lactamase; $V_H$ and $V_L$—sequences coding for the variable domains of the heavy and light chains of scFv-508, respectively; Lin—a gene coding for a $(Gly_4Ser)_3$ (SEQ ID NO:2) linker present between the variable domains $V_H$ and $V_L$. T7-promoter and T7 term—T7 promoter and T7 terminator sequences, respectively. Restriction sites and positions thereof are also shown.
Figure 4:
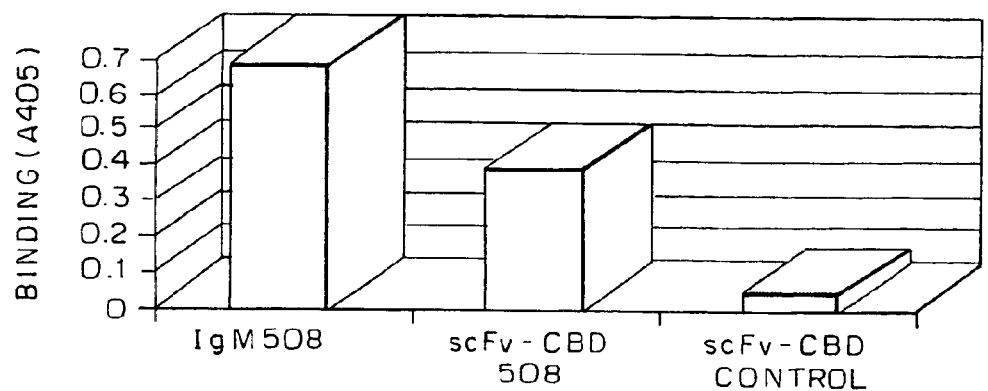
FIG. 4 shows an analysis of βAP binding by antibody 508(Fv)-CBD in an ELISA assay. The analyzed antibodies were added to βAP coated wells. Bound antibodies were detected with HRP conjugated secondary antibodies. The parental 508 IgM antibody was used as a positive control. The unrelated anti-β-galactosidase antibody Gal6(Fv)-CBD was used as a negative control.
Figure 5:
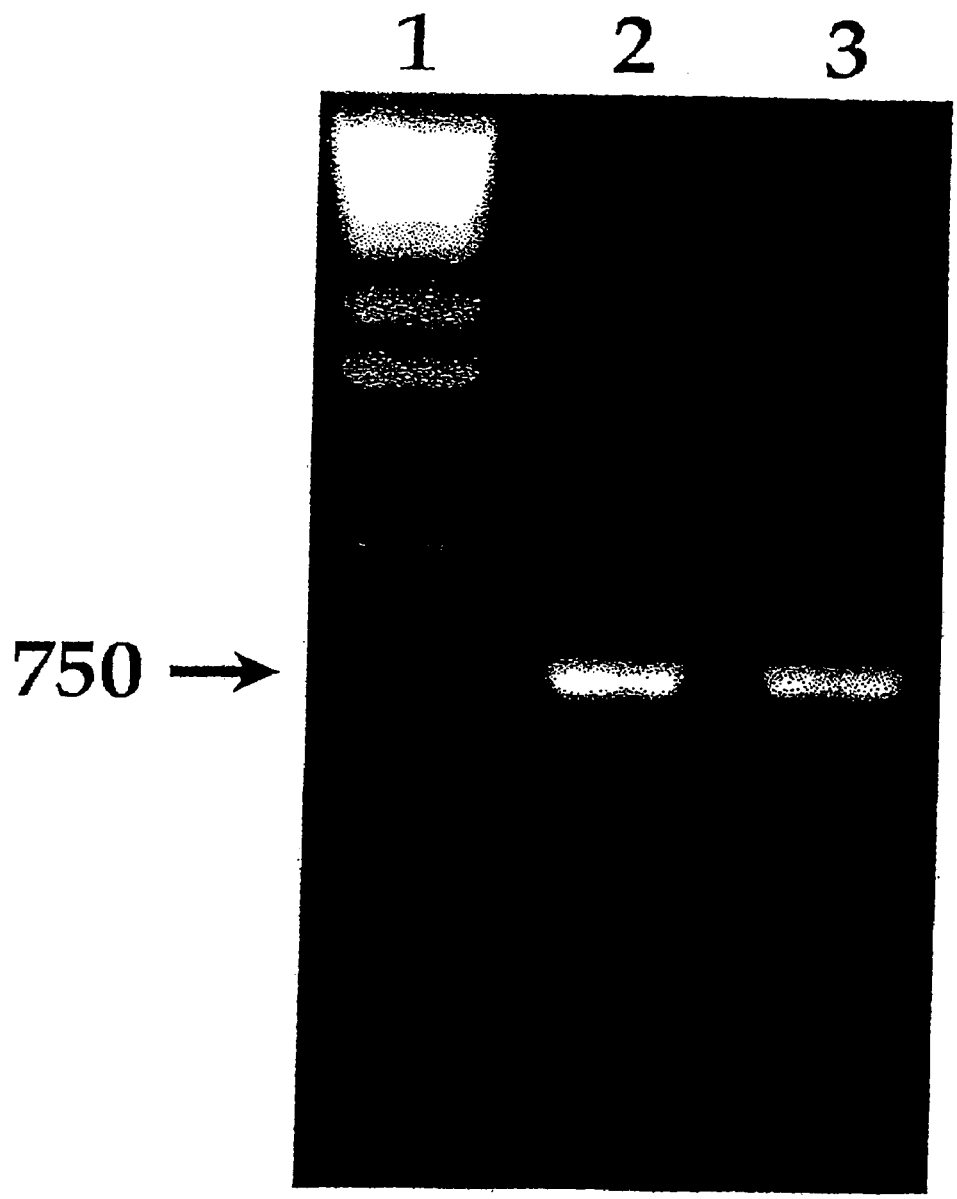
FIG. 5 shows PCR analysis of phage DNA inserts. DNA isolated from pCC-508(Fv), lane 2, and pCC-Gal6(Fv), Lane 3, were PCR amplified and separated on a 1.5% agarose gel. Ethidium bromide staining and UV illumination were used to visualize the bands. Lane 1 contains a DNA size marker. The arrow marks the position of an intact scFv migrating at about 750 bp.

MAb 508 showed specific recognition of β-amyloid and prevented its toxic affects on PC12 cells (Anavi S., 1998). For cloning the 508 antibody as a scFv in a phage display vector, RNA was extracted from $10^8$ 508 hybridoma cells and was used as a source for antibody variable region coding sequences. RT-PCR was used to amplify the variable domains that were cloned into the phage display vector pCC-Gal6(Fv), as described in Materials and Methods. When hybridoma derived antibodies are cloned as scFvs, some of the clones may contain aberrant sequences that are not functional. Therefore, to identify phagemid clones carrying functional β-amyloid binders from the generated clones, 10 individual clones were picked at random and soluble scFv-CBD fusion protein was produced thereby. FIG. 2 shows a physical map of plasmid pCC-508 that was used to express the 508-scFv. The CBD domain serves as an immunological detection of soluble scFv protein or as a novel approach in refolding of soluble scFv protein inclusion bodies of overexpressed protein (Berdichevsky et al, 1999). The plasmid used for 508-scFv over expression is shown in FIG. 3. The soluble scFv-CBD from the selected clones was incubated in wells of an ELISA plate that has been coated with β-amyloid peptide. Of the analyzed clones, 50% showed specific binding to βAP. FIGS. 1a–e demonstrate and illustrate the preparation of 508 scFv from IgM antibody. FIG. 4 shows βAP binding by the scFv-CBD produced by a positive clone that was chosen for further analysis. PCR analysis was used to characterize its DNA insert. It was found that the positive clone (designated pCC-508(Fv)) contained an intact DNA insert (FIG. 5). DNA sequencing of pCC-508(Fv) confirmed that the clone expresses an intact scFv fragment (see, FIGS. 11a–b and SEQ ID NOs:5 and 6, for nucleic and amino acid sequences, respectively, modified as further described below).

Example 3

Site Directed Mutagenesis of 508-(Fv) Antibody

Figure 7:
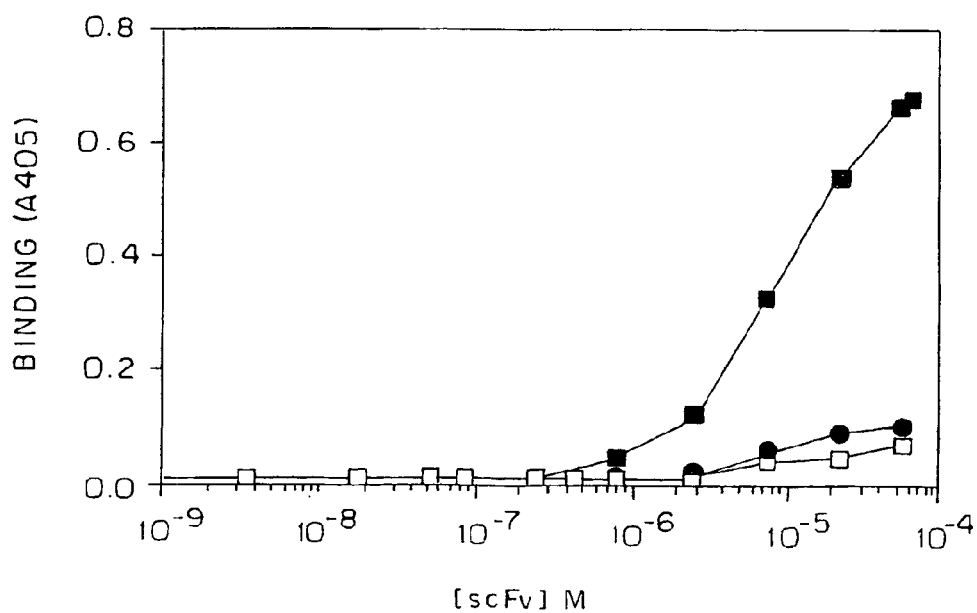
FIG. 7 demonstrates the stability of 508(Fv)-CBD. Purified 508(Fv)-CBD protein was stored at 4° C. for one day (dark squares) or one week (dark circles), and then analyzed for βAP binding in an ELISA assay, as described in the legend to FIG. 4. The unrelated antibody Gal6(Fv)-CBD served as a negative control (open squares).
Figure 6:
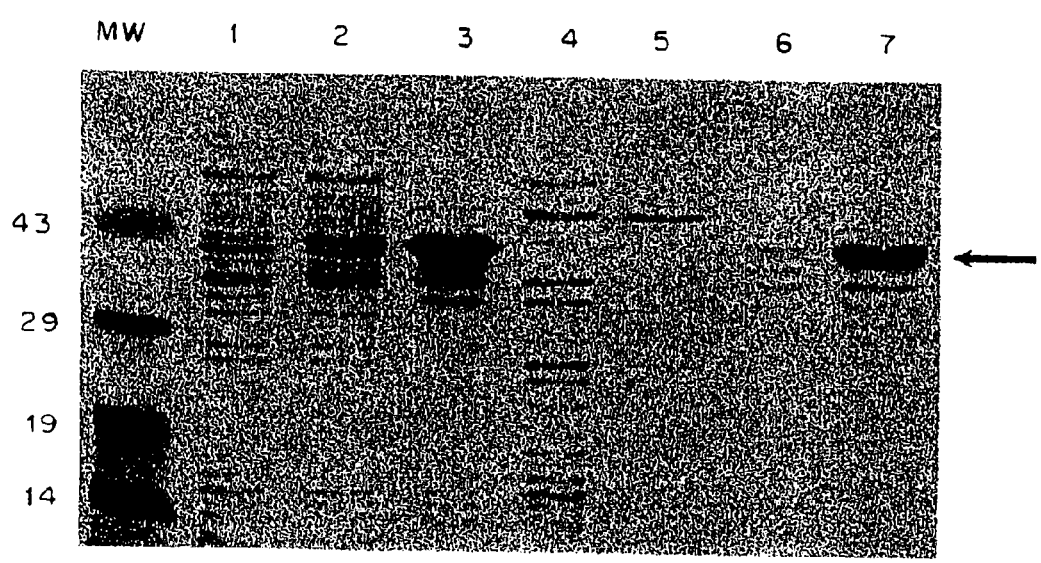
FIG. 6 demonstrates expression and purification of 508 (Fv)-CBD. 5–10 μg protein were loaded in each lane of a 14% SDS polyacrylamide gel. Proteins were visualized by Coomassie brilliant blue staining. The arrow marks the position of the scFv-CBD fusion protein. Lane 1—total cell extract from non-induced BL21(DE3) cells carrying 508 (Fv)-CBD expression vector. Lane 2—total cell extract from BL21(DE3) cells carrying 508((Fv)-CBD expression vector induced for 3 hours with IPTG. Lane 3—washed, solubilized and reduced inclusion bodies that were used in refolding. Lane 4—protein that did not bind to cellulose during cellulose-assisted refolding. Lane 5—protein washed away from cellulose with TBS. Lane 6—protein washed away from crystalline cellulose with distilled water. Lane 7—soluble 508(Fv)-CBD recovered from cellulose by high-pH elution and neutralization.

The DNA sequencing analysis of pCC508-(Fv) revealed the unusual appearance of a cysteine residue at the position 96 of $V_L$ CDR3 (Kabat et al, 1991). The deduced amino acid sequence of $V_L$ CDR3 is: $H^{89}QRSSYPCT^{97}$ (SEQ ID NO:15). The presence of an unpaired cysteine residue in a scFv may reduce its folding yield and also decrease its stability in solution and its storage half life. Therefore, 508(Fv) was subcloned into an expression vector and produced in E. coli as described in Materials and Methods. FIG. 6 summarizes the production process of 508(Fv)-CBD by the cellulose-assisted refolding method (Berdichevsky et al, 1999). Although 508(Fv)-CBD could be purified to near homogeneity (FIG. 6, lane 7) by this method, it refolded relatively poorly and was unstable upon storage at 4° C. (FIG. 7). It was assumed that substitution of the cysteine with a different residue may increase the production yield and stability of the soluble scFv without having an adverse affect on its affinity (Kirpriyanov et al, 1997).

Figure 8A:
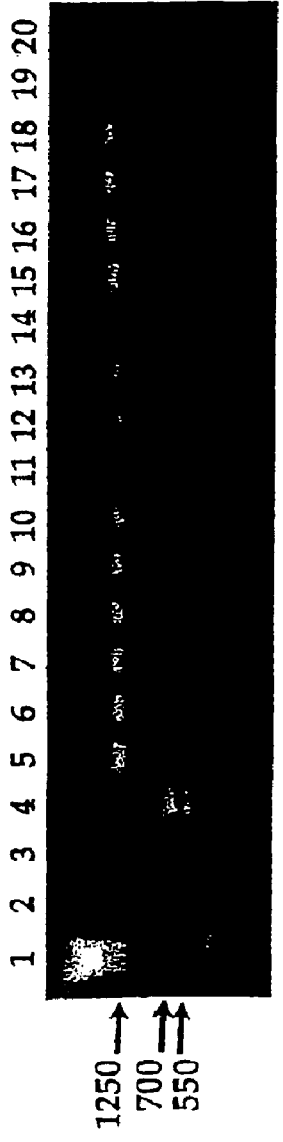
FIG. 8 demonstrates quantitation of 508(Fv) mutants affinity-enrichment by PCR and DNA restriction analysis. The DNA of 19 508(Fv)-mutant micro library clones before (FIG. 8a) and of 11 clones picked up after one cycle of affinity selection (FIG. 8b) were analyzed. The DNA was digested with PvuI and separated on a 1.5% agarose gel. A non-mutated scFv-CBD appears as an intact 1250 bp fragment (upper arrow). A mutated clone is indicated by the appearance of both 700 bp (middle arrow) and 550 bp (lower arrow) fragments. A DNA size marker is shown in lane 1.

For the replacement of the 508 $V_L$ cysteine 96 codon SOE PCR was used, which enabled the replacement of Cys 96 with phenylalanine, leucine, serine, tyrosine or tryptophan codons. In addition, the PCR scheme employed permits the persistence of the cysteine residue at that position. 508(FV) mutants were cloned into the pCC-Gal6(Fv) phage vector, resulting in the generation of a micro library (having 6 potential variant). The replacing residues chosen are generally acceptable at that CDR3 position, as they are found in various antibodies in the Kabat database (Kabat et al, 1991). However, different replacements may vary in their effect on βAP binding. To test which replacement maintains βAP binding, a single cycle of affinity selection was performed on the 508(Fv)-Mut micro phage library using biotinylated βAP(1–16) as a capturing antigen. PCR amplification and restriction analysis was used to monitor the enrichment of library clones after the affinity selection cycle. When the 508Mut-(Fv)-CBD DNA is digested with PvuI, a typical restriction pattern is obtained upon agarose-gel electrophoresis and ethidium-bromide staining. The lower 750 and 500 bp fragments represent the 508Mut-(FV)-CBD DNA, while an intact 1250 bp fragment represents scFv-CBD from the pCC-Gal6(Fv) DNA which was used as a vector. It was found that before affinity selection the library was heavily contaminated with the pCC-Gal(Fv) vector DNA. This is evident from the fact that the DNA of 18/19 randomly picked library clones was not cleaved at the PvuI site engineered adjacent to 508 $V_L$ position 96. Only one of the 19 analyzed clones showed the expected restriction pattern associated with a mutation (FIG. 8a). However, after affinity selection, 5/11 randomly selected clones showed the expected restriction pattern (FIG. Bb). This indicates an enrichment factor of about 10 fold, which demonstrates the ability of 508 scFv mutants to bind the βAP(1–16) epitope. The DNA sequences of the 5 mutants were determined and are shown in Table 1 below. Suitable replacements of 508 VL cysteine 96 codon were found to be phenylalanine, serine or tyrosine.

TABLE 1

Figure 8B:
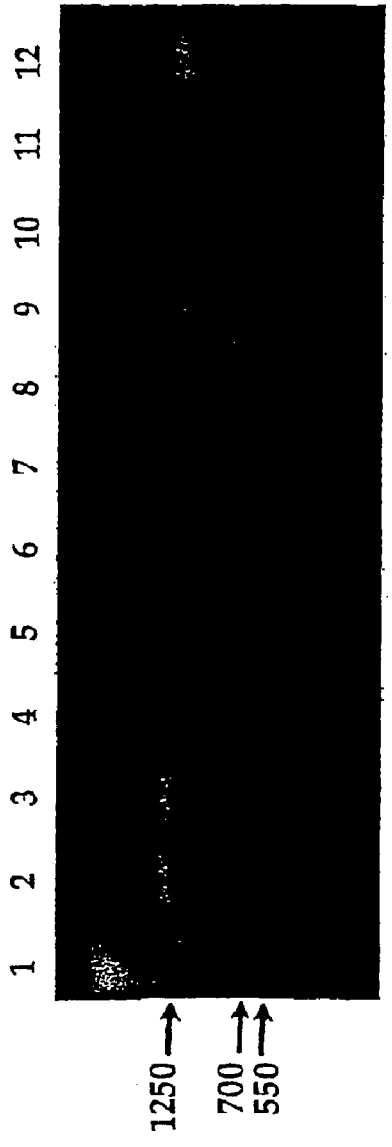

| Lane (FIG. 8b) | Amino Acid Sequence | SEQ ID NO: |
|---|---|---|
| 4 | $^{89}$HQRSSYP-$C^{96}$-T | 16 |
| 5 | $^{89}$HQRSSYP-$F^{96}$-T | 17 |
| 6 | $^{89}$HQRSSYP-$Y^{96}$-T | 18 |
| 8 | $^{89}$HQRSSYP-$F^{96}$-T | 19 |
| 11 | $^{89}$HQRSSYP-$S^{96}$-T | 20 |

Example 4

The recognition of βAP(1–16) by scFv 508 Mutants

Figure 9A:
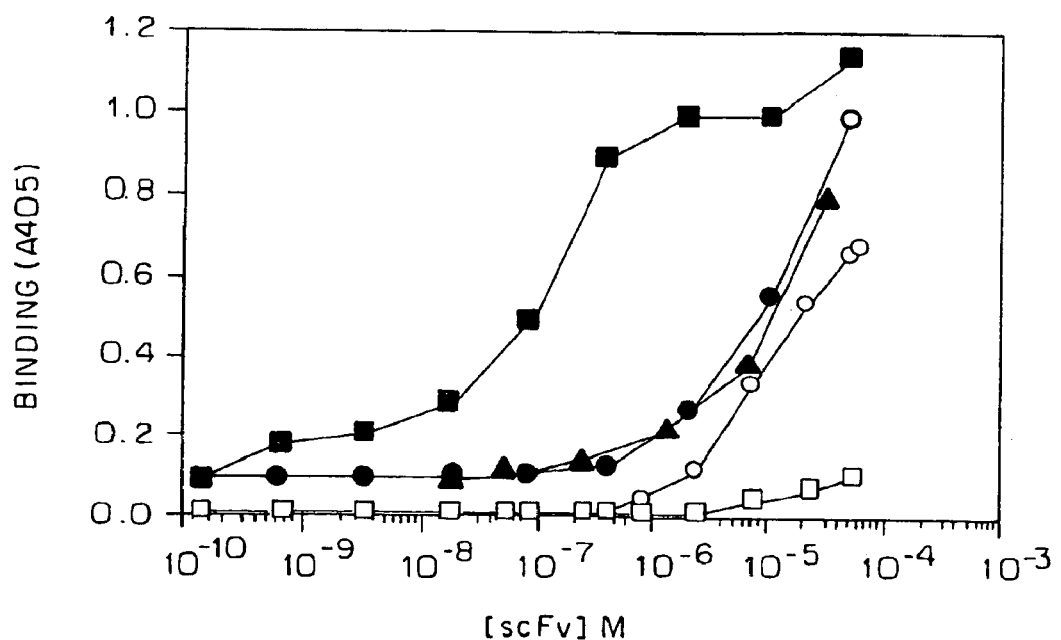
FIG. 9 shows an analysis of βAP binding (FIG. 9a) and stability (FIG. 9b) of mutated 508(Fv) derivatives in an ELISA assay. The analyzed antibodies were added to βAP-coated wells. Bound antibodies stored at 4° C. for one day or for one week were detected as described in the legend to FIG. 7. 508(Fv) wild type (open squares), C96F (dark squares), C96Y (dark circles), C96S (dark triangles). The unrelated anti-β-galactosidase antibody Gal6(Fv)-CBD was used as a negative control (open squares).
Figure 9B:
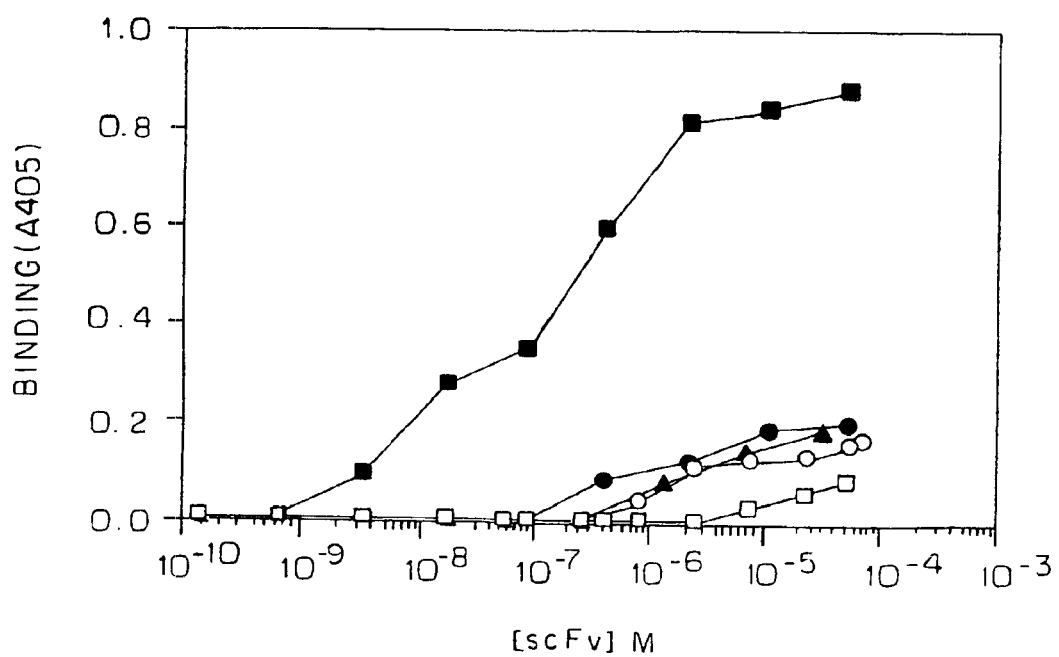
Figure 10:
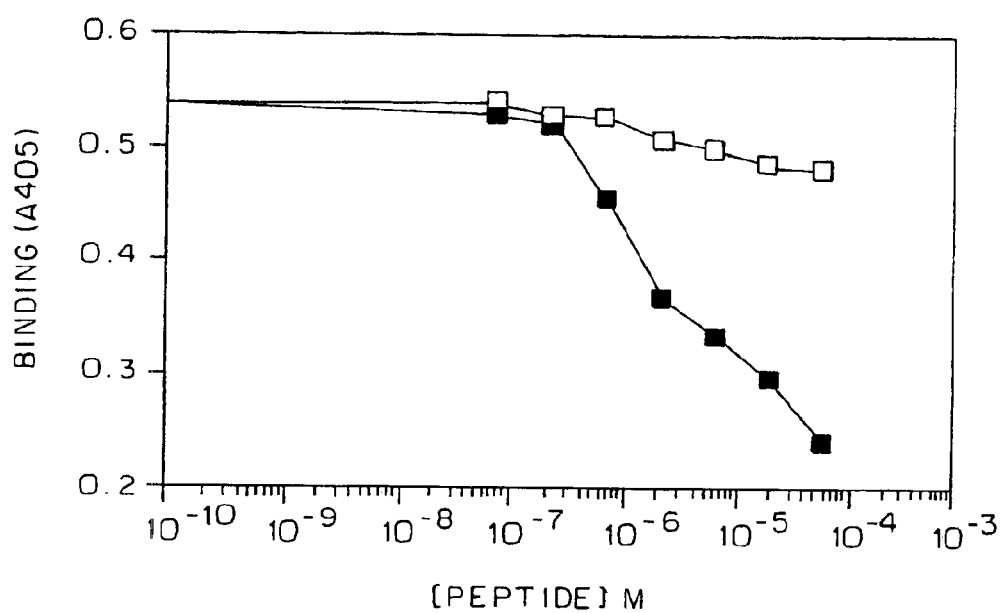
FIG. 10 shows an analysis of the specific inhibition of βAP binding by antibody 508F(Fv) in a competitive ELISA assay. The antibody was pre-incubated with varying concentrations of the competing peptides: βAP (acids 1–16 of SEQ ID NO:3) (dark squares) or the unrelated peptide WVLD (SEQ ID NO:4) (open squares), before being added to RAP coated wells. Bound antibodies were detected as described in the legend to FIG. 7.

For further examination of mutated 508 scFv derivatives, the mutated genes were subcloned into an expression vector and overexpressed in E. coli, as described for the wild type protein above. The interactions of the various mutated 508-(Fv) proteins (Table 1) with βAP(1–16) were tested in an ELISA assay. FIGS. 9a–b show that while the wild type 508-(Fv)-CBD binds at a half maximum binding (HMB) of $10^{-5}$ M, all the mutants showed improved binding to βAP: the HMB of C96S and C96Y is $5 \times 10^{-6}$ M and the HMB of C96F is $10^{-7}$ M. For further examination the 508-scFv mutant that carries the C96F mutation (508F(Fv)) was chosen, which show the higher affinity and shelf stability (FIGS. 9a–b). The specificity of βAP(1–16) binding by 508F(Fv) was tested in a competitive ELISA. As is shown in FIG. 10, binding of the purified 508F(Fv)-CBD to βAP was inhibited by soluble βAP(1-16) peptide serving as the competitor in the liquid phase in a dose-dependent manner. Inhibition of 50% binding was obtained at about 1 μM competitor. Binding was not affected by an irrelevant peptide (WVLD, SEQ ID NO:4).

Example 5

Prevention of the —Amyloid Neurotoxic Effect by 508F(Fv)

Figure 12:
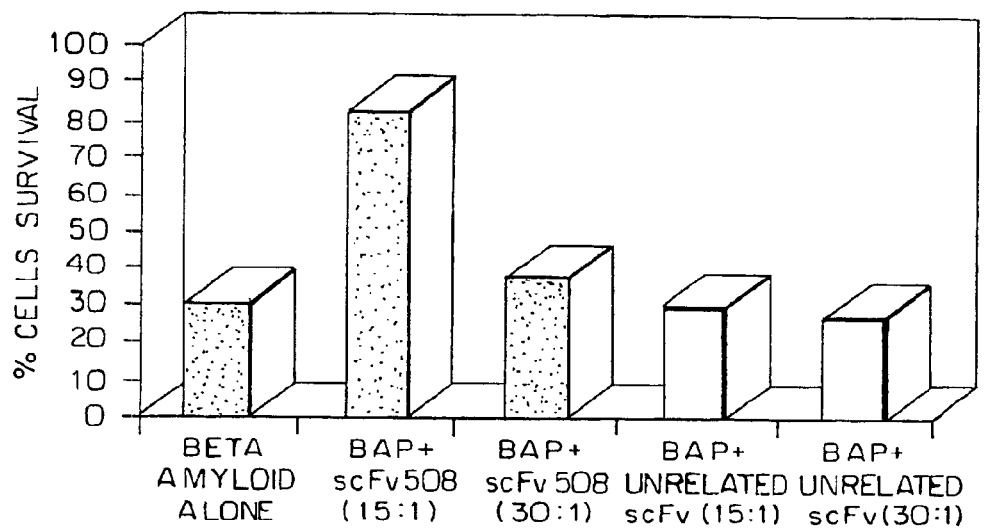
FIG. 12 demonstrates the prevention of βAP mediated toxic effect on PC12 cells by 508F(Fv). Cells were incubated with fibrillar βA alone, or with fibrillar βA that had been incubated with antibodies at different molar ratio of antibody/βAP, as indicated. An 3-(4,5-dimethylthiazol-2-yl)-2,5-diphenyl tetrazolium bromide (MTT) assay was used to estimate cell survival.

In order to find out whether 508F(Fv) exhibits a protective effect similar to the parental IgM antibody in preventing βA mediated neurotoxicity toward cultured cells, an in vitro test was applied using rat phenochromocytoma PC12 as described (Solomon et al, 1997). Viability of the cells exposed to βA with or without antibody was measured. As shown in FIG. 12, 508F(Fv) prevented the neurotoxicity of βA (90% cell viability) at a molar ratio βAP:scFv of 15:1, while the unrelated scFv showed no effect. Purified CBD or the scFv alone had no affect on the cells.

Example 6

Disaggregation of β-Amyloid Fibril by 508F(Fv)

Figure 13:
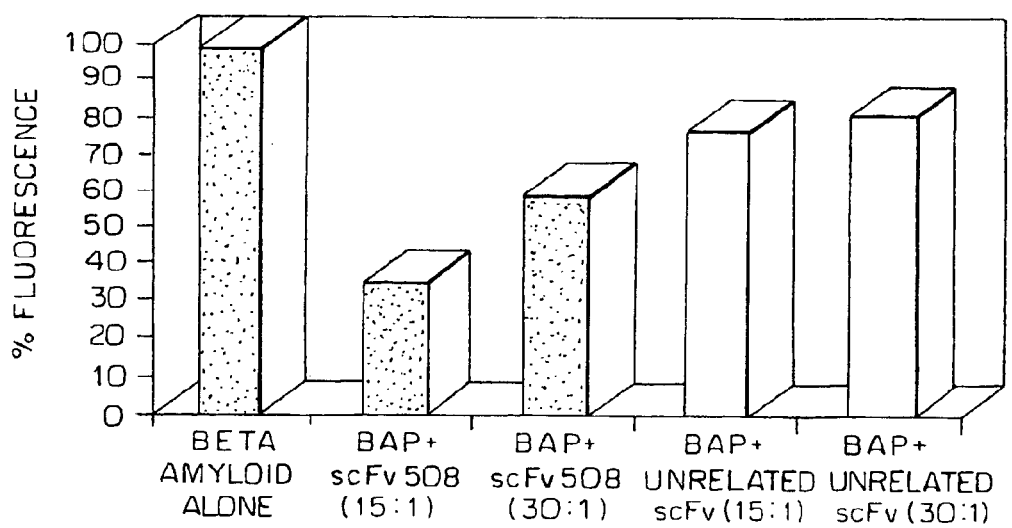
FIG. 13 demonstrates the disaggregation of fibrillar βA by 508F(Fv). The fibrillar state of pre-formed βA fibrils were measured with or without incubation with antibodies at different molar ratio of antibody/βAP, as indicated. The fluorescence of thioflavin-T (ThT) reagent in a ThT assay that is proportional to fibril βA was used to assess the fibril morphology.
Figure 14C:
FIGS. 14a–d demonstrate the detection of filamentous phage (f88-EFRH) in brain sections via immunofluorescence one day following a single dose applied intranasally. Appearance of filamentous phage in mouse olfactory bulb and hippocampus sections using fluorescent rabbit anti-phage antibody (FIGS. 14a and 14c, respectively) as is compare to an untreated mouse brain (FIGS. 14b and 14d, respectively). The sections were observed using a fluorescence microscope at a final magnification of ×10.
Figure 14D:
Figure 14A:
Figure 14B:
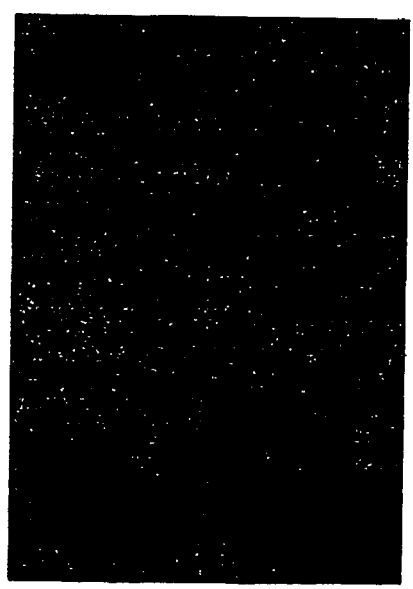
Figure 15C:
FIGS. 15a–d show histology of mouse brain sections after phage f88-EFRH clearance. Brain sections of olfactory organ (FIG. 15a) and hippocampus (FIG. 15c) after 28 days following phage f88-EFRH administration were stained with hematoxylin and eosin, and compared to sections of an untreated brain (FIGS. 15b and 15d, respectively). The stained sections were examined and photographed at a final magnification of ×40.
Figure 15D:
Figure 15A:
Figure 15B:
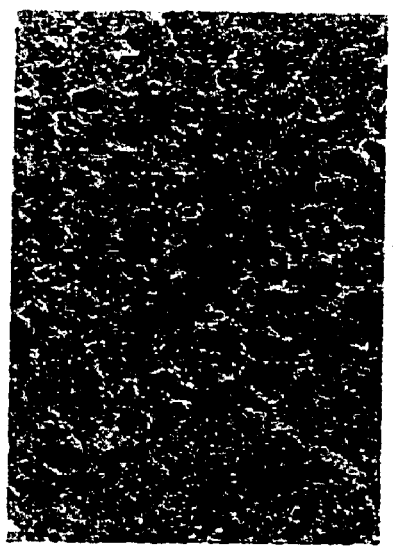
Figure 16C:
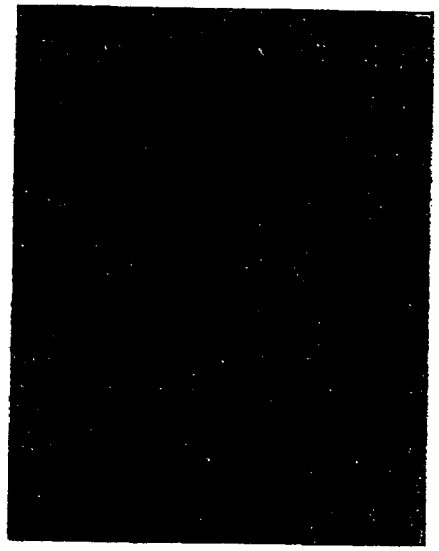
FIGS. 16a–d show histology of mouse brain after phage pCC-508F coupled to biotinylated βAP (acids 1–16 of SEQ ID NO:3) administration. Olfactory organ (FIG. 16a) and hippocampus (FIG. 16b) sections one day following phage administration were stained with hematoxylin and eosin, and were compared to untreated mouse brain sections (FIGS. 16c and 16d, respectively). The stained sections were examined and photographed at a final magnification of ×40.
Figure 16D:
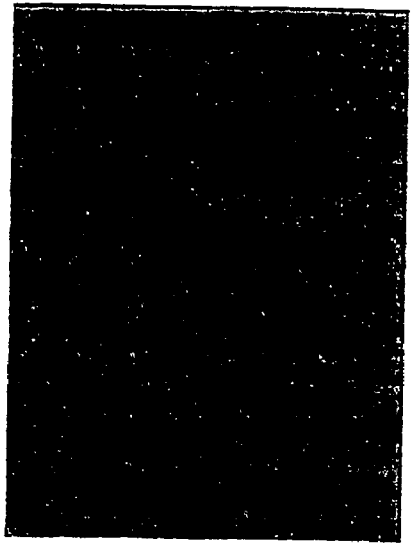
Figure 16A:
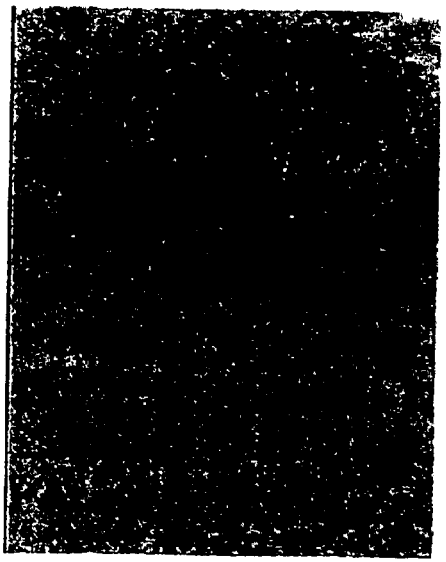
Figure 16B:
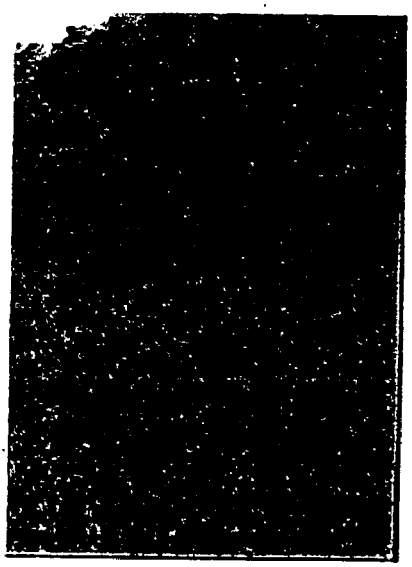

To examine the effect of 508F(Fv) on disruption of the βA fibril (the toxic form of βAP) the ThT reagent that binds specifically to fibrillar structures (Levine H III, 1993) was used. The interference with the already formed βA fibril was measured at the same molar ratio of βAP:scFv as in the βA neurotoxic assay and was quantitated by ThT fluorimetry. FIG. 13 shows that 508F(Fv) incubated with pre-formed βA fibrils disrupted the fibril structure indicating extensive deterioration of fibril morphology, as is evidenced by a substantial (62%) decrease in ThT fluorescence.

Example 7

Ability of Filamentous Phage to Enter the CNS Via Olfactory Track

Female Balb/c mice were treated with phage vector fB8-EFRH via intranasal administration. The purpose of this experiment was to check the ability of filamentous phage to reach the hippocampus region via olfactory tract. Since the phage is not carrying any specific molecule for targeting neuron cells, it should be vanished without causing any harm after several day following the administration. In order to investigate the appearance of phage in the olfactory bulb and the hippocampus region double labeling of antibodies was used as follows: rabbit polyclonal antibody anti filamentous phage and mouse monoclonal antibody against EFRH (SEQ ID NO:1) epitope fused to glycoprotein VIII of the phage surface. One day following a single intranasal administration of $10^{11}$ phages animals showed such phages in their olfactory bulb and hippocampus (FIGS. 14a–d). Seven days after the administration phages were detected in the olfactory bulb of only one mouse of the three tested, whereas no phages were revealed in the hippocampus. No evidence of phages was detectable 28 days following administration. As shown in FIGS. 15a–d, no evidence of change in the neuron population of the brain of treated mice was evident.

Example 8

Filamentous Phage Is Suitable Vehicle for Carrying Active Antibody Fragment to the CNS To check whether a filamentous phage can carry an antibody to the CNS via the olfactory track and still preserve the activity against β-amyloid a filamentous phage displaying 508F was incubated with $10^{-3}$ M biotinylated βAP (1–16), in order to form antibody antigen immunocomplex. Balb/c mice were divided into two groups and were administrated intranasally with two different antigens: 508F-βAP (1–16) immunocomplex and for comparison biotinylated βAP(1–16) alone. Following a single dose the mice were sacrificed and brain sections thereof prepared and reacted with streptavidin coupled to a fluorescent agent. Fluorescence was detected only in brain sections of mice that were administered with 508F-βAP(1–16), but not, or to a much lesser extent, in brain sections of mice that were administered with βAP(1–16) alone. No histological findings characterized treated mice (FIGS. 16a–d).

It is therefore assumed that the phage act as an inert vehicle of antibody to the brain, carrying the βAP(1–16) molecule into the brain.

Example 9

Figure 17:
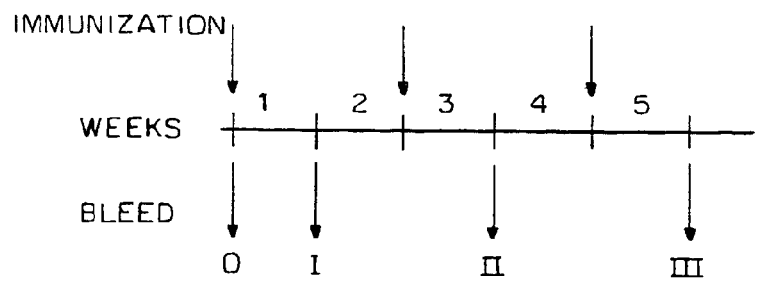
FIG. 17 is a diagram of immunization schedule with filamentous phage displaying the EFRH (SEQ ID NO:1) epitope of β-amyloid peptide.
Figure 18A:
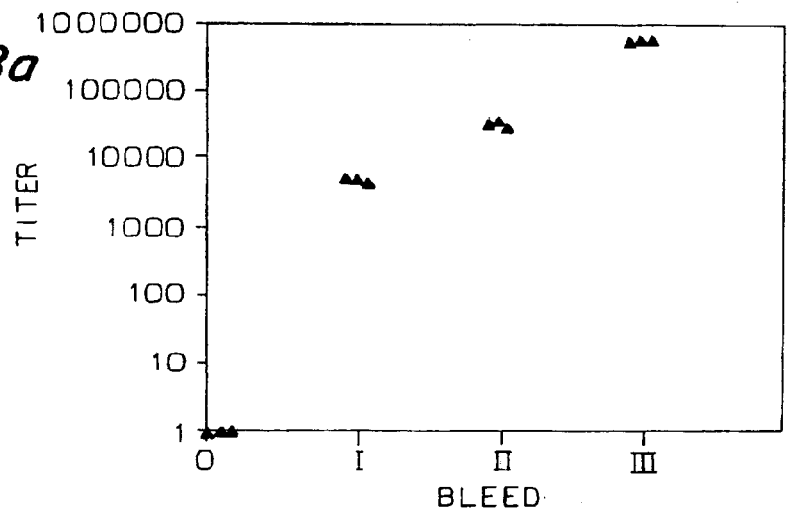
FIGS. 18a and 18b show immunization with f3 filamentous phage displaying EFRH (SEQ ID NO:1) epitope of β-amyloid peptide as a fusion of phage glycoprotein III (gpIII). Serum IgG titer of different bleeds from mice immunized with the EFRH-phage according to the schedule of FIG. 17 against wild type filamentous phage coat proteins (FIG. 18a) and the N-terminal epitope (acids 1–16, SEQ ID NO:3) of β-amyloid (FIG. 18b).
Figure 18B:
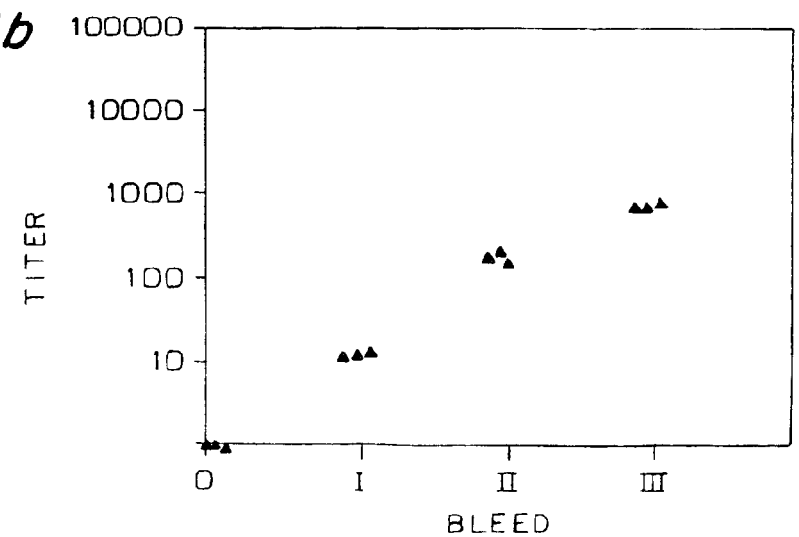
Figure 19:
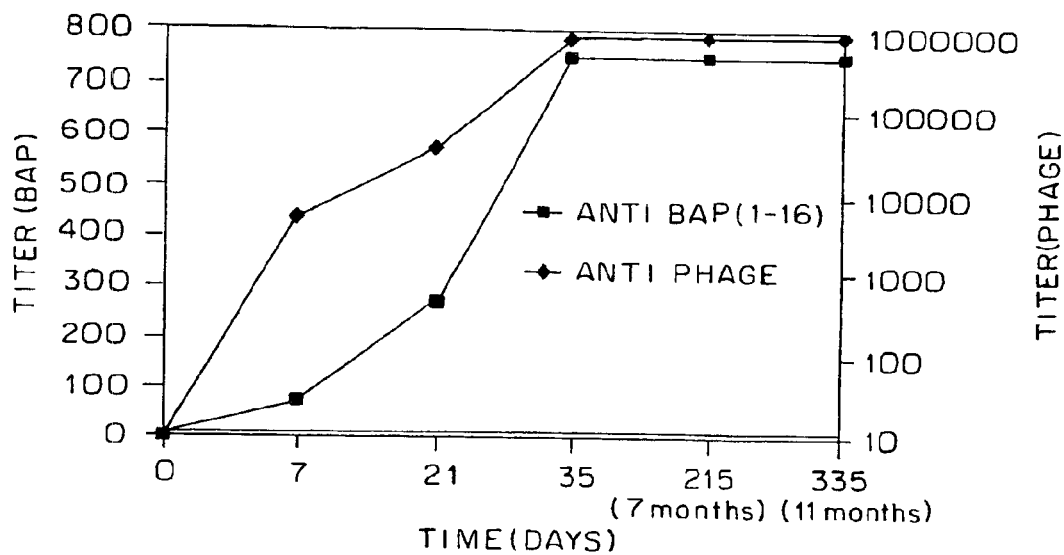
FIG. 19 demonstrates long lasting immunization with f3 filamentous phage. Serum IgG titer of different bleeds from mice immunized with EFRH-phage against wild type filamentous phage coat proteins and the N-terminal (acids 1–16, SEQ ID NO:3) of β-amyloid.

Raising Anti-Aggregating βAP Antibody Through Immunization of Mice with f3-EFRH Phage The anti-aggregating epitope within βAP (EFRH, SEQ ID NO:1) map to positions 3–6 of the amino acid sequence of βAP. In order to generate specific immune response against βAP, mice were immunized with genetically engineered fd phage carrying the peptide YYEFRH (SEQ ID NO:7) fused to its minor coat gpIII according to the immunization schedule shown in FIG. 17. Doses of $10_{10}$ phage particles per injection were used to immunize, at 14-day intervals, through intraperitoneal injection. Following 7 days of each injection, mice were bled and their sera tested by ELISA for IgG antibody reactivity against wild type phage (not bearing the peptide YYEFRH (SEQ ID NO:7) on its surface) and against βAP (FIGS. 18a–b). This route of administration gave a very high response against βAP (1:750) following the third injection. Furthermore, it was found that injection through phage carrying epitope is long lasting (FIG. 19), it is non-toxic and may be given without adjuvant. The phage vector is found to be an immunogenic tool to raise a high affinity immune response within 14 days from the first injection. The immune response against the peptide YYEFRH (SEQ ID NO:7) is low, compared to the immune response against the entire phage and could be explained by the low copy number of the fusion gpIII on the phage envelope. Therefore, for further analysis phages displaying the epitope through glycoprotein VIII were employed.

Example 10

Isolation of f88-EFRH Peptide-Displayed Phage by an Anti-Aggregating mAb

To identify a disaggregating EFRH (SEQ ID NO:1) peptide epitope a phage-epitope library was screened with biotinylated antibody. After three cycles of panning and phage amplification, 90 individually isolated bacterial colonies were grown in microtiter plates and their phages were assayed for antibody binding. ELISA analysis revealed that of the phage-clones that were selected followed by three biopanning cycles, most (above 80%) bound specifically to anti-aggregating mAb, respectively. DNA from 6 positive clones was sequenced (Table 2). The sequence EFRH (SEQ ID NO:1) appeared in 4 clones, one additional clone had the sequence EPRH (residues 2-5 of SEQ ID NO:23), with only one residue replacement of proline with phenylalanine. In one additional clone, the inserted peptide bears the sequence of the three residues FRH (acids 2–4 of SEQ ID NO:1), lacking the glutamate residue.

TABLE 2

| Amino acid Sequence (name) | SEQ ID NO: | No. of Phages |
|---|---|---|
| VHEPHEFRHVALNPV (C3-II) | 8 | 2 |
| DTEFRHSSNNFSAVR (C7-II) | 21 | 1 |
| STEFRHQTTPLHPNS (C11-I) | 22 | 1 |
| KEPRHHIQHHERVIR (F8-II) | 23 | 1 |
| SAADFRHGSPPISAF (D3-I) | 24 | 1 |

Figure 20:
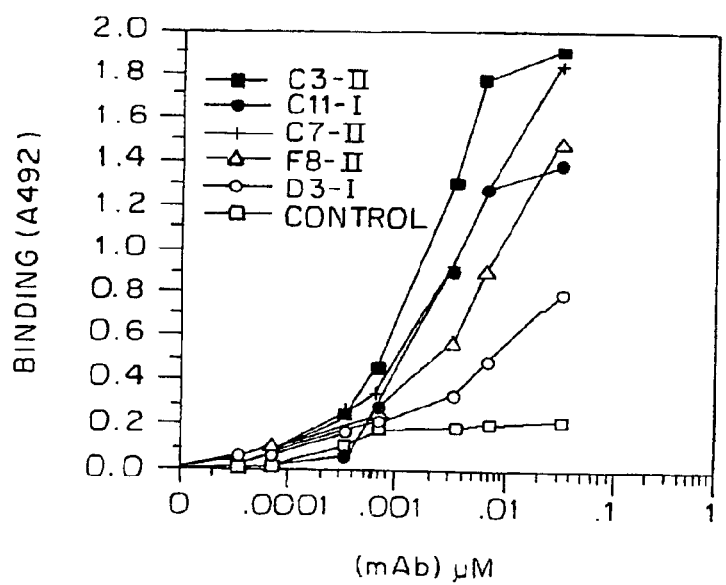
FIG. 20 show binding of anti-aggregating βAP monoclonal antibody (mAb 10D5) to peptide-presenting phage selected from an f88 phage library. Unrelated mAb 5.5 raised against acetylcholine receptor was used as a negative control. Antibodies were added to phage-coated wells and ELISA was used to detect binding.
Figure 21:
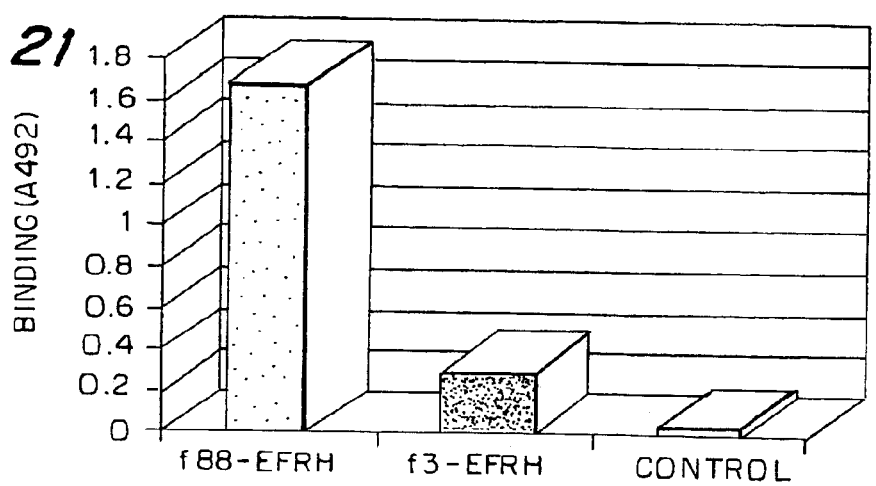
FIG. 21 show binding of anti-aggregating βAP mAb (10D5) to a YYEFRH (SEQ ID NO:7)-phage and VHEP-HEFRHVALNPV (SEQ ID NO:8)-phage. Antibody in concentration of 1 μg/ml was added to phage-coated wells and binding was analyzed by ELISA. Filamentous phage without insert was used as a control.

Binding of anti-aggregating mAb to the EFRH (SEQ ID NO:1)-bearing phage was concentration dependent; half-maximal binding was obtained at an antibody concentration of 100 ng/ml, corresponding to $10^{-9}$ M (FIG. 4), which resembles the level of binding of these antibodies to the whole peptide. One specific f88-EFRH (SEQ ID NO:1) phage (termed C3-II, table 2) showed higher level of avidity as is compared to the others (FIG. 20). It may be due to higher level of EFRH (SEQ ID NO:1) epitope exposure on its surface. Binding tests of f88-EFRH or f3-EFRH with the same concentration of anti-aggregating antibody (1 μ/ml) demonstrated a higher number of EFRH (SEQ ID NO:1) epitope copies per phage that may lead to higher serum titer via phage immune response (FIG. 21).

Example 11

Figure 22A:
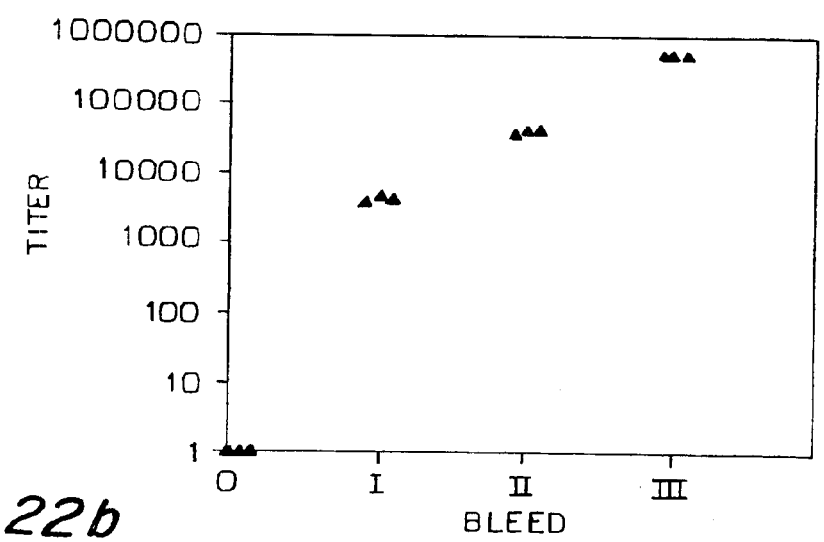
FIGS. 22a–b show immunization with f88 filamentous phage displaying EFRH (SEQ ID NO:1) epitope of β-amyloid peptide as a fusion of phage glycoprotein VIII (gpVIII). Serum IgG titer of different bleeds from mice immunized with EFRH-phage against wild type filamentous phage coat proteins (FIG. 22a) and the N-terminal epitope (acids 1–16, SEQ ID NO:3) of β-amyloid peptide (FIG. 22b).
Figure 22B:
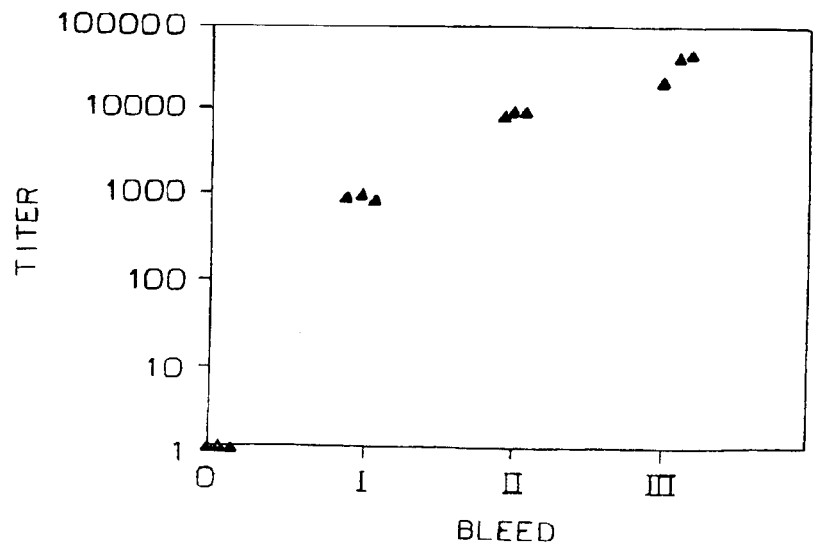

Raising Anti-Aggregating βAP Antibody Through Immunization of Mice with f88-Phage In order to generate the same specific immune response against βAP, mice were immunized with genetically engineered fd phage carrying the peptide VHEPHEFRHVALNPV (SEQ ID NO:8) fused to its major coat gpVIII. This phage was selected from a 15-mer phage peptide library by an anti aggregating βAP antibody and is presenting the mAb epitope (underlined) within βAP. This phage was used to immunize mice as described. Following 7 days of each injection with $10^{10}$ phage particles (without adjuvant) the mice were bled and their sera tested by ELISA for IgG antibody reactivity against wild type phage and against βAP. The results are summarized in FIGS. 22a–b. All animals showed a measurable response of IgG antibody against the wild type phage, and titers increased with the second and the third injection. This route also gave the highest titer measurable responses against βAP (1:50,000) after the third injection (FIG. 22b).

Example 12

Inhibition of Antibody Serum Binding to β-Amyloid Peptide

Figure 23:
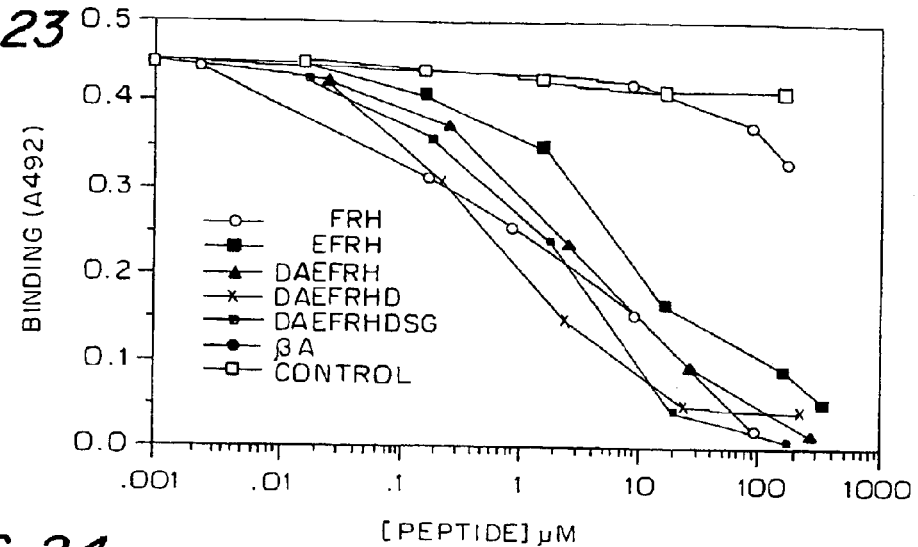
FIG. 23 shows inhibition of serum of immunized mice in binding to βAP by synthetic peptides derived from the N-terminal of β-amyloid peptide. The assay was done with 1:3000 dilution of serum after a third immunization with f88-EFRH reacted with the various peptides (FRH; EFRH (SEQ ID NO:1); DAEFRH (residues 1–6 of SEQ ID NO:3; DAEFRHD (residues 1–7 of SEQ ID NO:3); DAEFRHDSG (residues 1–9 of SEQ ID NO:3); and βA) in various concentrations per well, as indicated. The peptide WVLD (SEQ ID NO:4) was used as a negative control.

The interaction of mouse serum immunized by phage f88-EFRH with βAP was further assayed by competitive inhibition experiments. FIG. 23 shows inhibition of mice serum antibody with synthesized peptides derived from βAP, each of which includes the sequence EFRH (SEQ ID NO:1)) such as: DAEFRH (positions 1–6, SEQ ID NO:3), DAEFRHD (positions 1–7, SEQ ID NO:3), DAEFRHDSG (positions 1–9, SEQ ID NO:3), and βAP itself, DAEFRHDSGYEVHHQKLVFFAEDVGSNKGAIIGLMVGGVV (positions 1–40, SEQ ID NO:3).

FIG. 23 shows that all of the synthetic peptides which bear the motive EFRH (SEQ ID NO:1) similarly inhibited binding of mouse serum antibody to the βAP with $IC_{50}$ values of about $5 \times 10^{-6}$ M. These data indicate that the epitope of mouse serum antibody within the βAP molecule is composed of four amino acid residues corresponding to positions 3–6 in the βAP that were found to act as a regulatory site controlling both the solubilization and the disaggregation process of the βA molecule.

Example 13

Figure 24:
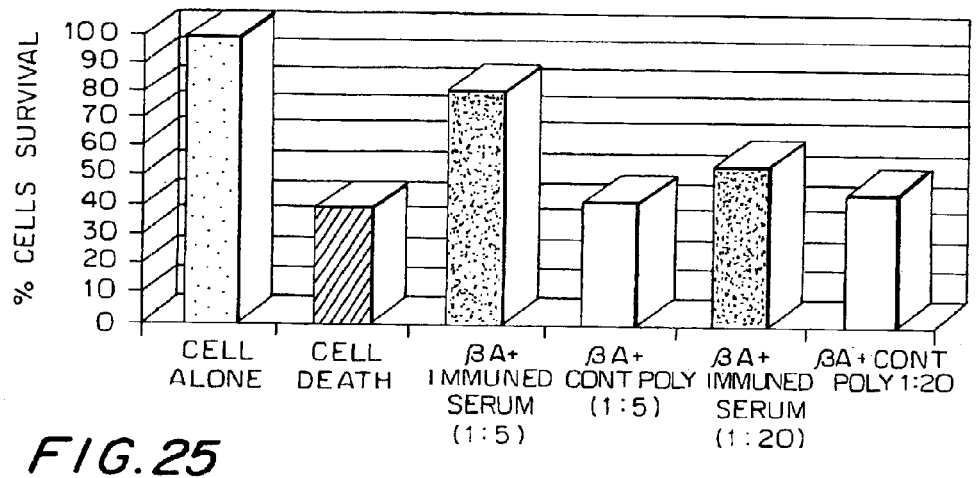
FIG. 24 demonstrates prevention of βAP mediated toxic effect on PC12 cells by serum antibodies raised against f88-EFRH-phage. Cells were incubated with fibrillar βA alone, or with fibrillar βA that has been incubated with serum from the third bleeding at different concentration. The negative control was serum from a non-immunized mouse. The MTT assay was used to estimate cell survival.

Prevention of the 1-Amyloid Neurotoxic Effect by Serum Antibody Raised Against EFRH-Phage In order to find out whether serum of f88-EFRH immunized mice exhibits a protective effect similar to the parental IgG antibody in preventing βA mediated neurotoxicity toward cultured cells, the in vitro test using rat phenochromocytoma PC12 was applied as described (Solomon et al, 1997). Viability of the cells exposed to βA with or without antibody was measured. As shown in FIG. 24, diluted serum of 1:5 prevented the neurotoxicity of βA (80% cell viability), while the unrelated serum showed no effect.

Example 14

Figure 25:
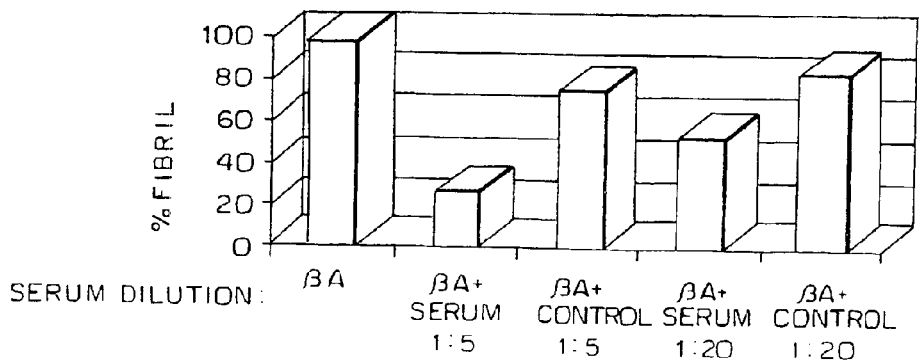
FIG. 25 demonstrates interference with fibrillar β-amyloid formation by serum antibodies raised against the f88-EFRH-phage. Estimation of the fluorescence of ThT which correlates with the amount of fibrillar β-amyloid formed after incubation for a week at 37° C. in the presence of serum samples diluted as indicated. The negative control was serum from a non-immunized mouse. The positive control was without serum. Fibril formation was measured by the ThT assay.

Disaggregation of 1-Amyloid Fibril by Serum of EFRH (SEQ ID NO:1) Immunized Mice To examine the effect of serum of f88-EFRH immunized mice on disruption of the βA fibril (the toxic form of βAP) the ThT reagent that binds specifically to fibrillar structures (Levine H. III, 1993) was used. βAP samples were incubated for a week at 37° C. and then were exposed to different dilutions of mouse serum antibody. Fibril formation was quantitated by the ThT fluorometry binding assay. FIG. 25 shows that mouse serum, at dilution of 1:5 and 1:20, disrupted the fibril structure of βA with extensive deterioration of fibril morphology, as indicated by a substantial 75% (1:5 dilution) and 50% (1:20 dilution) decrease in ThT fluorescence. The unrelated serum used as control (serum from non-immunized mouse), did not significantly inhibit fibril formation as is compared to the immunized serum. This result strongly emphasizes the ability of the EFRH (SEQ ID No:1) epitope displayed by a filamentous phage vector to evoke an immune response resulting in anti-aggregation antibody.

Example 15

The teachings of the present invention can also be applied to prion related diseases that are also characterized by plaque formation.

The possible involvement of the PrP protein in the pathogenesis of nerve cell degeneration and glial cell reaction led to the identification of a PrP sequences that play a role in the amyloid formation. A fragment of PrP consisting of amino acids 106–126 was demonstrated to be toxic to rat hippocampal neurons (Forloni et al, 1993), to mouse cortical and cerebellar cells (Brown et al, 1994; 1997), and to be particularly highly fibrillogenic (Selvaggini et al, 1993). The formed fibrils were partially resistant to proteases digestion and exhibited properties of in situ amyloid (Selvaggini et al, 1993, Tagliavini et al, 1993). Synthetic peptides corresponding to this region of PrP exhibit conformational flexibility from α-helix to a β-sheet conformation (Selvaggini et al, 1993) that was similar to conformational changes from $PrP^C$ to $PrP^{Sc}$. The conformational plasticity of this region is further emphasized by the findings that two distinct prion strains which exhibit different sites of proteolytic cleavage within this region (Bessen et al, 1994; Telling et al, 1996).

As is further described below, the inventors of the present invention have generated mAbs specific to epitopes formed by amino acids 106–126 of the PrP protein. Such antibodies are useful in studying plaque formation and morphology and as possible active agents for treating or preventing prion generated plaque diseases.

Preparation of Monoclonal Antibodies Against PrP 106–126

Mice immunized with a synthetic peptide corresponding to the amino acid sequence of human PrP 106–126 coupled to the larger carrier KLH were used for generating monoclonal antibodies reactive against epitopes on this peptide. Sera derived from the immunized mice were subjected to ELISA and several positive clones composed mainly of immunoglobulin M (IgM) molecules and to a lesser extent IgG molecules were detected and isolated.

Two immunoglobulin clones that were isolated as described above and designated mAbs 3–11 (IgM) and mAb 2–40 (IgG1) were utilized in further studies.

Example 16

Search for Epitope Location using Phage Display Library

Phage display libraries displaying various peptide fragments of the human PrP 106–126 polypeptide were generated as described hereinabove in the method section. Clones reactive to mAbs 3–11 or mAb 2–40 (for each library) were not detected following 6 cycles of library biopanning (368 clones screened) raising the possibility that epitopes that are recognized by these antibodies are of a conformational nature.

Example 17

Competitive Inhibition of Antibodies Bound to PrP by Peptide NMKH (SEQ ID NO:26)

Figures 26, 27:
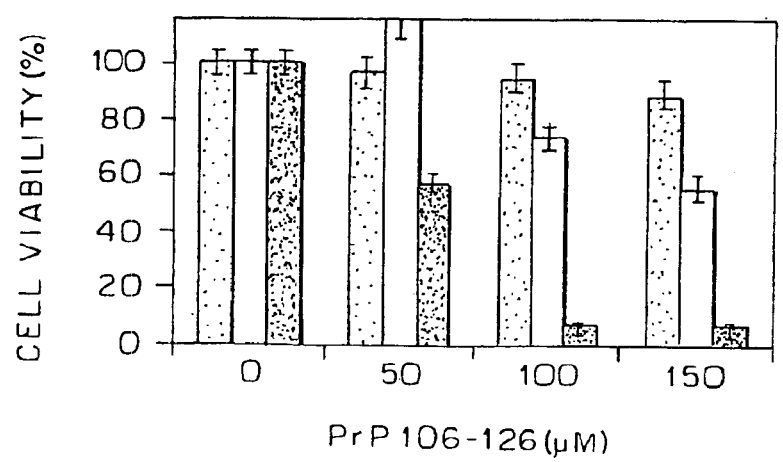
FIG. 26 illustrates the amino acids sequence corresponding to the human prion protein 106–126(SEQ ID NO:25) and to the mouse homologue (SEQ ID NO:29).
FIG. 27 demonstrates the neurotoxicity effect of the PrP peptide as measured by MTT assay. PC12 cells were seeded in 96 well plates in a DMEM medium supplemented with 2 mM insulin, 2 μM L-glutamine and 100 units penicillin/ streptomycin. Cell viability was assessed by the MTT assay following incubation with PrP 106–126, (at different concentrations). PrP 106–126 was either preincubated for 4 days at 37° C. and then added to the cells for 3' days (grey bars), or was preincubated for 4 days at 37° C. and then added to the cells for 5 days (white bars) or was preincubated for 7 days at 37° C. and was then added to the cells for 5 days (black bars).

The above described anti-PrP 106–126 antibodies were preincubated with a peptide of an amino acid sequence NMKH (SEQ ID NO:26) at equimolar ratio before reacting with the PrP 106–126 polypeptide in order to determine the ability of NMKH (SEQ ID NO:26) to compete with the human PrP 106–126 for antibody binding. As shown in FIG. 26, this sequence is highly conserved between mice and human sequences (and others) with the exception of two different amino acids, M109 instead of L and M 112 instead of V. These two differences probably contribute to antigenic differences between the mouse and human sequences, since the antibodies which were derived from mice immunized with the human sequence corresponding to PrP 106–126 did not cross react with the mouse sequence corresponding to peptide PrP 106–126.

Competition (as analyzed by ELISA) between the NMKH (SEQ ID NO:26) and whole peptide was not detected, supporting the suggestion that the epitope may depend upon three dimensional conformation and not primary structure. In addition, co-reacting mAb 3F4 (recognizing the sequence NMKH (SEQ ID NO:26)) and mAb 3–11 with PrP 106–126 did not produce an additive response, suggesting that their epitopes may be adjacent or overlapping (Solomon et al, 1991).

Example 18

PrP Aggregation and Immunocomplex Formation

Incubation of PrP 106–126 at 37° C. at different concentrations led to a dose dependent fibrillar aggregation as measured by the Thioflavin T binding fluorescence assay (FIG. 28). A PrP 106–126 concentration of 0.3 mg/ml was selected for further studies.

Example 19

Cytotoxicity Assay of PrP 106–126 Using PC12 Cells

Since the major target organ for $PrP^{Sc}$ is the nervous system, in vitro neuronal model systems were used to analyze PrP toxicity. A clonal cell line that exhibits neuronal properties has been established from rat central nervous system tumors (Schubert et al, 1974). The rat pheochromocytoma PC12 cells—a neuron-like cloned tumor cell line (Greene et al, 1976)—has been shown to enable in vitro replication of $PrP^{Sc}$ (Rubenstein et al, 1984). As such, this cell line was utilized by the present study as a model for detecting molecules with the ability to prevent toxicity induced by PrP fibrils.

Using this model system, it was uncovered that PrP 106–126 is toxic to PC12 cells in a dose dependant manner, which toxicity is related to the conformational state of the peptide and to the exposure time of the cells to aggregated peptide. Cell viability considerably decreased (as detected by MTT assay), when cells were incubated with PrP 106–126 for 5 days in comparison to a 3 day exposure. Furthermore, preincubation of PrP 106–126 at 37° C. prior to its addition to the cells increased its toxicity probably by increasing the amount of amyloid fibrils. Preincubation of the peptide for 7 days resulted in a significantly higher toxicity that was concentration dependent (FIG. 27). Under the described conditions, cell viability was reduced to 10% at a concentration of 100 $\mu$M of PrP 106–126 as was measured by MTT assay.

Example 20

Prevention of PrP 106–126 Neurotoxicity

The cytoprotective effect of mAb 3–11 and 2–40 is shown in FIG. 29. mAbs 3–11 and 2–40 inhibited cell death that was induced by 100 $\mu$M PrP 106–126. The viability of cells treated with a mixture of either antibody and the peptide was 85–89%, as compared to a 40% survival rate in cells treated with the peptide alone. (The antibodies without the peptide had no affect on cell viability.) The antibodies' protective effect was apparently related to the specific epitope on the PrP molecule, since such protection was not demonstrated with mAb 3F4 (44% viability).

Example 21

Anti-Aggregating Properties of Monoclonal Antibodies as Measured by ThT Assay

The amyloid fibril formation of PrP 106–126 was detected by a thioflavin-T (ThT) binding assay. Both mAbs 3-11 and 2–40 prevent PrP 106–126 fibrillar aggregation and disaggregate the aggregated form of this peptide. A significant decrease in amyloid fibril formation (about 80% prevention) was observed when PrP 106–126 was incubated at 37° C. in the presence of mAbs 3–11 and 2–40. When these antibodies were added to already formed aggregates of PrP 106-126, more than 50% of the fibrils were disaggregated. In contrast, mAb 3F4 had lower efficacy both in inhibiting amyloid fibril formation and in inducing their disaggregation (FIG. 30). Both the inhibition of amyloid fibril formation and the induction of disaggregation were dependent on the antibody's concentration and the epitope location (FIGS. 30–31).

The protective effect of mAbs 3–11 and 2–40 of the present invention and of mAb 3F4 was calculated as shown in Equation 1 below.

$$\%\text{Protective effect} = 100 - \frac{\text{Emission 482 nm (PrP 106 – 126 incubated with Ab)}}{\text{Emission 482 nm (PrP 106 – 126 incubated alone)}} \times 100 \quad \text{(Equation 1)}$$

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications cited herein are incorporated by reference in their entirety.

REFERENCES

Anavi S. M. Sc. thesis from the department of Molecular Microbiology and Biotechnology of the Tel-Aviv University, Israel (1998)

Banks et al, "Bidirectional passage of peptides across the blood-brain barrier", *Prog Brain Res* 91:139–148 (1992)

Berdichevsky et al, "Phage display of a cellulose binding domain from *Clostridium* thermoce llum and its application as a tool for antibody engineering", *J Immunol Methods* 228(1–2):151–162 (1999)

Bessen et al, "Distinct PrP properties suggest the molecular basis of strain variation in transmissible mink encephalopathy", *J Virol* 68:7859–7868 (1994)

Blond et al, "Partly native epitopes are already present on early intermediates in the folding of tryptophan synthase", *Proc Natl Acad Sci USA* 84:1147–1151 (1987)

Borrebaeck AK, *Antibody Engineering—A Practical Guide*, W. H. Freeman and Co. (1992)

Brown et al, "Mouse cortical cells lacking cellular PrP survive in culture with a neurotoxic PrP fragment", *Neuroreport* 5:2057–2060 (1994)

Brown et al, "Different requirements for the neurotoxicity of fragments of PrP and β-amyloid", *Eur J Neurosci* 9:1162–1169 (1997)

Burke et al, "The influence of adjuvant on the therapeutic efficacy of a recombinant genital herpes vaccine", *J Inf Dis* 170:1110–1119 (1994)

Carlson et al, "Antibody assisted protein refolding", *Biotechnology* 10(1):86–89 (1992)

Caughey et al, "Secondary structure analysis of the scrapie-associated protein PrP 27–30 in water by infrared spectroscopy", *Biochemistry* 30(31):7672–7680 (1991)

Chartier-Harlin et al, "Early-onset Alzheimer's disease caused by mutations at codon 717 of the beta-amyloid precursor protein gene", *Nature* 353:844–846 (1991)

Chou et al, "Distribution of antihistamines into the CSF following intranasal delivery ", *Biopharm Drug Dispos* 18(4):335–346 (1997)

De Gioia et al, "Conformational polymorphism of the amyloidogenic and neurotoxic peptide homologous to residues 106–126 of the prion protein", *J Biol Chem* 269(11):7859–7862 (1994)

Delmastro et al, "Immunogenicity of filamentous phage displaying peptide mimotopes after oral administration", *Vaccine* 15(11):1276–1285 (1997)

Donne et al, "Structure of the recombinant full-length hamster prion protein PrP(29–231): the N terminus is highly flexible", *Proc Natl Acad Sci USA* 94(25):13452–13457 (1997)

Draghia et al, "Gene delivery into the central nervous system by nasal instillation in rat", *Gene Ther* 2(6):418–423 (1995)

Fingl et al, 1975, in *The Pharmacological Basis of Therapeutics*, Ch. 1 p.1

Forloni et al, "Neurotoxicity of a prion protein fragment", *Nature* 362(6420):543–546 (1993)

Frauenfelder et al, "Temperature-dependent X-ray diffraction as a probe of protein structural dynamics", *Nature* 280(5723):558–563 (1979)

Frenkel et al, "N-terminal EFRH sequence of Alzheimer's β-amyloid peptide represents the epitope of its anti-aggregating antibodies", *J Neuroimmunology* 88(1–2):85–90(1998)

Gajdusek DC, "Unconventional viruses and the origin and disappearance of kuru", *Science* 197:943–960 (1977)

Goate et al, Segregation of a missense mutation in the amyloid precursor protein gene with familial Alzheimer's disease", Nature 349:704–706 (1991)

Greene et al, "Establishment of a noradrenergic clonal line of rat adrenal pheochromocytoma cells which respond to nerve growth factor", *Proc Natl Acad Sci USA* 73(7):2424–2428 (1976)

Hanan and Solomon, Amyloid: Int. J. Exp. Clin. Invest. 3:130–133 (1996)

Hansen et al, "Re-examination and further development of a precise and rapid dye method for measuring cell growth/cell kill", *J Immunol Methods* 119(2):203–210 (1989)

Hardy J, Amyloid, the presenilins and Alzheimer's disease", *Trends Neurosci* 20(4):154–159 (1997)

Harlow et al, *Antibodies: A Laboratory Manual*, Cold Spring Harbor Laboratory, Cold Spring Harbor, N.Y., Chapter 8 (1988)

Horiuchi et al, "Specific binding of normal prion protein to the scrapie form via a localized domain initiates its conversion to the protease-resistant state", *EMBO J.* 18(12):3193–3203 (1999)

Huston et al, "Protein engineering of single-chain Fv analogs and fusion proteins" in Methods in Enzymology (JJ Langone, ed.; Academic Press, New York, N.Y.) 203:46–88 (1991)

Johnson et al, "Construction of single-chain Fvb derivatives of monoclonal antibodies and their production in *Escherichia coli*", *Methods in Enzymol* 203:88–99 (1991)

Johnstone et al, *Immunochemistry in Practice*, Blackwell Scientific Publications, Oxford (1982)

Kabat et al, *Sequences of Proteins of immunological Interest,* 5th Ed., National Institutes of Health (1991)

Kanyo et al, "Antibody binding defines a structure for an epitope that participates in the PrPC-->PrPSc conformational change", J Mol Biol 293(4):855–863 (1999)

Karplus et al, "Molecular dynamics simulations in biology", *Nature* 347(6294):631–639 (1990)

Kirpriyanov et al, "Two amino acid mutations in an anti-human CD3 single chain Fv antibody fragment that affect the yield on bacterial secretion but not the affinity", *Protein Eng* 10(4):445–53 1997

Kohler et al, "Continuous cultures of fused cells secreting antibody of predefined specificity", *Nature* 256(5517):495–497 (1975)

Laemmli UK, "Cleavage of structural proteins during the assembly of the head of bacteriophage T4", *Nature* 227 (259):263–270 (1970)

Larocca et al, "Targeting bacteriophage to mammalian cell surface receptors for gene delivery", Hum Gene Ther 9(16):2393–2399 (1998)

Lefebrve et al, "Improvement of the gene splicing overlap (SOE) method", *Biotechniques* 19(2):186–188 (1995)

Levine H III "Thioflavine T interaction with synthetic Alzheimer's disease beta-amyloid peptides: detection of amyloid aggregation in solution", *Protein Sci* 2(3):404–410 (1993)

Mathison et al, "Nasal route for direct delivery of solutes to the central nervous system: fact or fiction?", *J Drug Target* 5(6), 415–441 (1998)

Medori et al, "Fatal familial insomnia, a prion disease with a mutation at codon 178 of the prion protein gene" *N Engl J Med* 326(7): 444–449 (1992)

Mernaugh et al, "An overview of phage-displayed recombinant antibodies" in *Molecular Methods in Plant Pathology* (Singh et al, eds.), CRC Press Inc., Boca Raton, Fla. (1995) pp. 359–365

Morag et al, "Expression, purification, and characterization of the cellulose-binding domain of the scaffoldin subunit from the cellulosome of *Clostridium thermocellum*", *Appl Environ Microbiol* 61(5):1980–1986 (1995)

Morris GE (Ed), *Epitope Mapping Protocols in Methods in Molecular Biology*, Vol. 66, Humana Press Inc., Totowo, N.J., (1996)

Mullan et al, "A pathogenic mutation for probable Alzheimer's disease in the APP gene at the N-terminus of beta-amyloid", *Nature Genet* 1(5):345–347 (1992)

Murrell et al, "A mutation in the amyloid precursor protein associated with hereditary Alzheimer's disease", Science 254(5028):97–99 (1991)

Naiki et al, "Fluorometric determination of amyloid fibrils in vitro using the fluorescent dye, thioflavin T1", *Anal Biochem* 177(2):244–249 (1989)

Pan et al, "Conversion of alpha-helices into beta-sheets features in the formation of the scrapie prion proteins", Proc Natl Acad Sci USA 90(23):10962–10966 (1993)

Poul et al, "Targeted gene delivery to mammalian cells by filamentous bacteriophage", *J Mol Biol* 288(2):203–211 (1999)

Rubenstein et al, "In vitro replication of scrapie agent in a neuronal model: infection of PC12 cells", *J Gen Virol* 65(Pt 12):2191–2198 (1984)

Schenk et al, "Immunization with amyloid-beta attenuates Alzheimer-disease-like pathology in the PDAPP mouse", *Nature* 400(6740):173–177 (1999)

Schubert et al, "Clonal cell lines from the rat central nervous system", *Nature* 249(454):224–227

Selvaggini et al, "Molecular characteristics of a protease-resistant, amyloidogenic and neurotoxic peptide homologous to residues 106–126 of the prion protein", *Biochem Biophys Res Commun* 194(3):1380–1386 (1993)

Seubert et al, "Isolation and quantification of soluble Alzheimer'S beta-peptide from biological fluids", *Nature* 359 (6393):325–327 (1992)

Silen et al, "The alpha-lytic protease pro-region does not require a physical linkage to activate the protease domain in vivo", *Nature* 341(6241):462–464 (1989)

Sladowski et al, "An improved MTT assay", *J Immunol Methods* 157(1–2):203–207 (1993)

Solomonet al, "Thermostabilization of carboxypeptidase A by interaction with its monoclonal antibodies", *Biotechnol Appl Biochem* 14(2):202–211 (1991)

Solomon, et al "Microalbuminuria immunoassay based on antibodies covalently conjugated to Eupergit C-coated beads", *Diabetes Care* 15(11):1451–1454 (1992)

Solomon et al, "Eupergit C-coated membranes as solid support for a sensitive immunoassay of human albumin", *J Immunol Methods"*, 157(1–2):209–215 (1993)

Solomon et al, "Chaperone-like effect of monoclonal antibodies on refolding of heat-denatured carboxypeptidase A", ", *J Mol Recognit.* 8(1–2):72–76 (1995)

Solomon et al, "Monoclonal antibodies inhibit in vitro fibrillar aggregation of the Alzheimer beta-amyloid peptide", *Proc Natl Acad Sci USA* 93(1):452–455 (1996)

Solomon et al, "Disaggregation of Alzheimer beta-amyloid by site-directed mAb", *Proc Natl Acad Sci USA* 94(8): 4109–4112. (1997)

Studier et al, "Use of T7 RNA polymerase to direct expression of cloned genes", *Methods Enzymol* 185:60–89 (1990)

Tagliavini et al, "Synthetic peptides homologous to prion protein residues 106–147 form amyloid-like fibrils in vitro", *Proc Natl Acad Sci USA* 90(20):9678–9682 (1993)

Telling, et al, "Evidence for the conformation of the pathologic isoform of the prion protein enciphering and propagating prion diversity", *Science* 274(5295):2079–2082 (1996)

Tigges et al, "Human herpes simplex virus (HSV)-specific CD8+CTL clones recognize HSV-2-infected fibroblasts after treatment with IFN-gamma or when virion host shutoff functions are disabled", J Immunol 156(10) :3901–3910 (1996)

Wilesmith et al, "Bovine spongiform encephalopathy", *Curr Top Microbiol Immunol* 172:21–38 (1991)

Willis et al, "Immunological properties of foreign peptides in multiple display on a filamentous bacteriophage", *Gene* 128(1):79–83 (1993)

Young et al, "Selective amylin antagonist suppresses rise in plasma lactate after intravenous glucose in the rat. Evidence for a metabolic role of endogenous amylin", FEBS Lett, 343 (3);237–241 (1994)

---

What is claimed is:

1. A pharmaceutical composition in unit dosage form, comprising a pharmaceutically acceptable carrier, and, as an active ingredient, a bacteriophage displaying a polypeptide, wherein said polypeptide comprises at least one epitope of beta-amyloid (Aβ), and wherein said at least one epitope elicits Aβ-binding antibodies against said epitope when administered to a subject, and wherein said antibodies inhibit aggregation of said beta-amyloid.

2. The pharmaceutical composition of claim 1, wherein said bacteriophage is selected from the group consisting of a double stranded DNA virus, a single stranded DNA virus, a positive strand RNA virus and a negative strand RNA virus.

3. The pharmaceutical composition of claim 1, wherein said bacteriophage is capable of propagation in bacterial flora in said subject.

4. The pharmaceutical composition of claim 1, wherein said bacteriophage is capable of propagation in *Escherichia coli*.

5. The pharmaceutical composition of claim 1, wherein said bacteriophage is selected such that less than 30 days following an introduction of a triple dose of $10^{10}$ units thereof to the subject, a titer of said antibodies is above 1:50,000, as is determined by ELISA.

6. A pharmaceutical composition in accordance with claim 1, wherein said polypeptide is Aβ.

7. A pharmaceutical composition in accordance with claim 1, wherein said epitope is EFRH (SEQ ID NO: 1), DAEFRH (residues 1–6 of SEQ ID NO: 3), DAEFRHD (residues 1–7 of SEQ ID NO: 3), or DAEFRHDSG (residues 1–9 of SEQ ID NO: 3).

8. A pharmaceutical composition in accordance with claim 1, wherein said epitope comprises EFRH (SEQ ID NO: 1).

9. A method of treating Alzheimer's disease, comprising introducing a pharmaceutical composition in accordance with claim 1 into a body of a recipient in need thereof so as to inhibit aggregation of beta-amyloid and treat Alzheimer's disease.

10. The method of claim 9, wherein said bacteriophage is selected from the group consisting of a double stranded DNA virus, a single stranded DNA virus, a positive strand RNA virus and a negative strand RNA virus.

11. The method of claim 9, wherein said bacteriophage is capable of propagation in bacterial flora in said recipient.

12. The method of claim 9, wherein said bacteriophage is capable of propagation in *Escherichia coli*.

13. The method of claim 9, wherein the Alzheimer's disease is early onset Alzheimer's disease.

14. The method of claim 9, wherein the Alzheimer's disease is late onset Alzheimer's disease.

15. The method of claim 9, wherein the Alzheimer's disease is presymptomatic Alzheimer's disease.

16. The method of claim 9, wherein said bacteriophage is introduced into the body of the recipient so as to inhibit aggregation of beta-amyloid by applying said bacteriophage to an olfactory system of the recipient.

17. A method in accordance with claim 9, wherein said polypeptide is Aβ.

18. A method in accordance with claim 9, wherein said epitope is EFRH (SEQ ID NO: 1), DAEFRH (residues 1–6 of SEQ ID NO: 3), DAEFRHD (residues 1–7 of SEQ ID NO: 3), or DAEFRHDSG (residues 1–9 of SEQ ID NO: 3).

19. A method in accordance with claim 9, wherein said epitope comprises EFRH (SEQ ID NO: 1).

* * * * *